United States Patent [19]

Hayes et al.

[11] Patent Number: 4,877,745

[45] Date of Patent: Oct. 31, 1989

[54] APPARATUS AND PROCESS FOR REAGENT FLUID DISPENSING AND PRINTING

[75] Inventors: Donald J. Hayes, Plano; David B. Wallace, Dallas, both of Tex.; Donald J. Verlee, Libertyville, Ill.; Kenneth R. Houseman, Racine, Wis.

[73] Assignee: Abbott Laboratories, Abbott Park, Ill.

[21] Appl. No.: 325,037

[22] Filed: Mar. 14, 1989

Related U.S. Application Data

[63] Continuation of Ser. No. 931,476, Nov. 17, 1986, abandoned.

[51] Int. Cl.[4] .................. G01D 9/00; G01D 15/16; G01N 1/10; G01N 21/75
[52] U.S. Cl. .................................... 436/166; 346/1.1; 346/140 R; 422/55; 422/56; 422/58; 422/61; 436/180
[58] Field of Search .............. 346/1.1, 140 R; 422/55, 422/56, 58, 61; 436/166, 180

[56] References Cited

U.S. PATENT DOCUMENTS

| | | | |
|---|---|---|---|
| 2,249,867 | 7/1941 | Snelling | 73/335 |
| 2,512,743 | 6/1950 | Hansell | 91/18 |
| 2,850,359 | 9/1958 | Worthington et al. | 23/230 |
| 2,951,894 | 9/1960 | Hirsch | 346/140 X |
| 3,127,281 | 3/1964 | Meyer | 117/4 |
| 3,150,592 | 9/1964 | Stec | 103/1 |
| 3,177,800 | 4/1965 | Welsh | 346/75 X |
| 3,215,078 | 11/1965 | Stec | 103/1 |
| 3,270,672 | 9/1966 | Haines et al. | 103/1 |
| 3,371,233 | 2/1968 | Cook | 310/8.1 |
| 3,373,437 | 3/1968 | Sweet et al. | 346/75 |

(List continued on next page.)

FOREIGN PATENT DOCUMENTS 0260965  3/1988 European Pat. Off.

OTHER PUBLICATIONS

*Circular Slot Burner–Droplet Generator System for High-Temperature Reaction and Vapor Transport Studios,* Analytical (Chem., vol. 51, No. 11, 9/1979).
*Vaporization and Atomization of Large Particles in an Acetylene/Air Flame,* Holcombe et al, Analytical Chem., vol. 50, No. 14, 12/1978.
*Application of Ink Jet Technology to a Word Processing Output Printer,* Buehner et al, Jan. 1977.
*Scale Model of an Ink Jet,* Curry et al, Jan. 1977.
*Satellite Droplet Formation in a Liquid Jet,* Pimbley et al, Jan. 1977.
*Effect of Parameter Variations on Drop Placement in an Electrostatic Ink Jet Printer,* Twardek, Jan. 1977.
*Drop Charging and Deflection in an Electrostatic Ink Jet Printer,* Fillmore et al, Jan. 1977.

(List continued on next page.)

*Primary Examiner*—Michael Lusignan
*Attorney, Agent, or Firm*—Thomas D. Brainard; Rodney A. Daniel; Edward H. Gorman, Jr.

[57] ABSTRACT

This invention relates to a system for printing and dispensing chemical reagents in precisely controlled volumes onto a medium at a precisely controlled location. A jetting tube, comprising an orifice at one end and a fluid receiving aperture at the other end, is concentrically mounted within a cylindrical piezo-electric transducer. The fluid receiving aperture is connected to a reservoir containing a selected reagent by means of a filter. The reservoir may be pressurized by a regulated air supply. An electrical signal of short duration is applied to the transducer. The pulse causes the transducer and the volume defined by the jetting tube to expand, thereby drawing in a small quantity of reagent fluid. The cessation of the pulse causes the transducer and the volume of the jetting tube to de-expand, thereby causing at least a substantially uniformly sized droplet of reagent fluid to be propelled through the orifice. The droplet may be directed to impact a printing medium or collected in a dispensing recepticle.

18 Claims, 10 Drawing Sheets

U.S. PATENT DOCUMENTS

| | | | |
|---|---|---|---|
| 3,427,480 | 2/1969 | Robinson | 310/8.1 |
| 3,452,360 | 6/1969 | Williamson | 346/140 |
| 3,507,269 | 4/1970 | Berry | 252/408 X |
| 3,512,173 | 5/1970 | Damouth | 346/75 |
| 3,549,328 | 12/1970 | Kilburn | 252/408 X |
| 3,666,421 | 5/1972 | Price | 424/12 X |
| 3,683,212 | 8/1972 | Zoltan | 346/75 X |
| 3,711,252 | 1/1973 | Roy | 252/408 X |
| 3,832,579 | 8/1974 | Arndt | 346/75 X |
| 3,838,012 | 9/1974 | Higgens et al. | 195/127 |
| 3,859,169 | 1/1975 | O'Driscoll et al. | 424/94 X |
| 3,902,083 | 8/1975 | Zoltan | 310/8.1 |
| 3,946,398 | 3/1976 | Kyser et al. | 346/75 X |
| 3,964,871 | 6/1976 | Hochstrasser | 195/127 X |
| 3,975,162 | 8/1976 | Renn | 424/12 X |
| 3,994,423 | 11/1976 | Burg | 222/420 |
| 3,996,006 | 12/1976 | Pagano | 422/50 |
| 4,046,513 | 9/1977 | Johnson | 427/2 X |
| 4,087,332 | 5/1978 | Hansen | 195/127 |
| 4,216,245 | 8/1980 | Johnson | 427/2 |
| 4,234,103 | 11/1980 | Strobl, Jr. et al. | 222/83.5 |
| 4,308,546 | 12/1981 | Halasz | 346/140 R |
| 4,341,310 | 7/1982 | Sangiovanni et al. | 222/420 X |
| 4,366,490 | 12/1982 | DeBonte et al. | 346/140 R |
| 4,418,356 | 11/1983 | Reece | 346/140 R |
| 4,426,031 | 1/1984 | Halasz | 228/121 |
| 4,447,375 | 5/1984 | Schimmelpfunnig | 264/40.5 |
| 4,492,322 | 1/1985 | Hieftje et al. | 222/420 |
| 4,503,012 | 3/1985 | Starr | 436/180 |
| 4,504,845 | 3/1985 | Kattaer et al. | 346/140 R |
| 4,514,743 | 4/1985 | Roschlein et al. | 346/140 R |
| 4,539,575 | 9/1985 | Nilsson | 346/1.1 X |
| 4,548,825 | 10/1985 | Voss et al. | 118/25 X |
| 4,550,325 | 10/1985 | Viola | 346/140 PD |
| 4,646,104 | 2/1987 | Braun | 346/1.1 |
| 4,672,398 | 6/1987 | Kawabara et al. | 346/140 PD |
| 4,681,741 | 7/1987 | Hanaway | 422/100 |

OTHER PUBLICATIONS

*Boundary Layer Around a Liquid Jet*, Lee, Jan. 1977.
*Controlling Print Height in an Ink Jet Printer*, Carmichael, Jan. 1977.
*Study of Fluid Flow Through Scaled-Up Ink Jet Nozzles*, Levanoni, Jan. 1977.
*Development and Characterization of Ink for an Electrostatic Ink Jet Printer*, Ashley et al., Jan. 1977.
*Materials Selection for an Ink Jet Printer*, Beach et al, Jan. 1977.

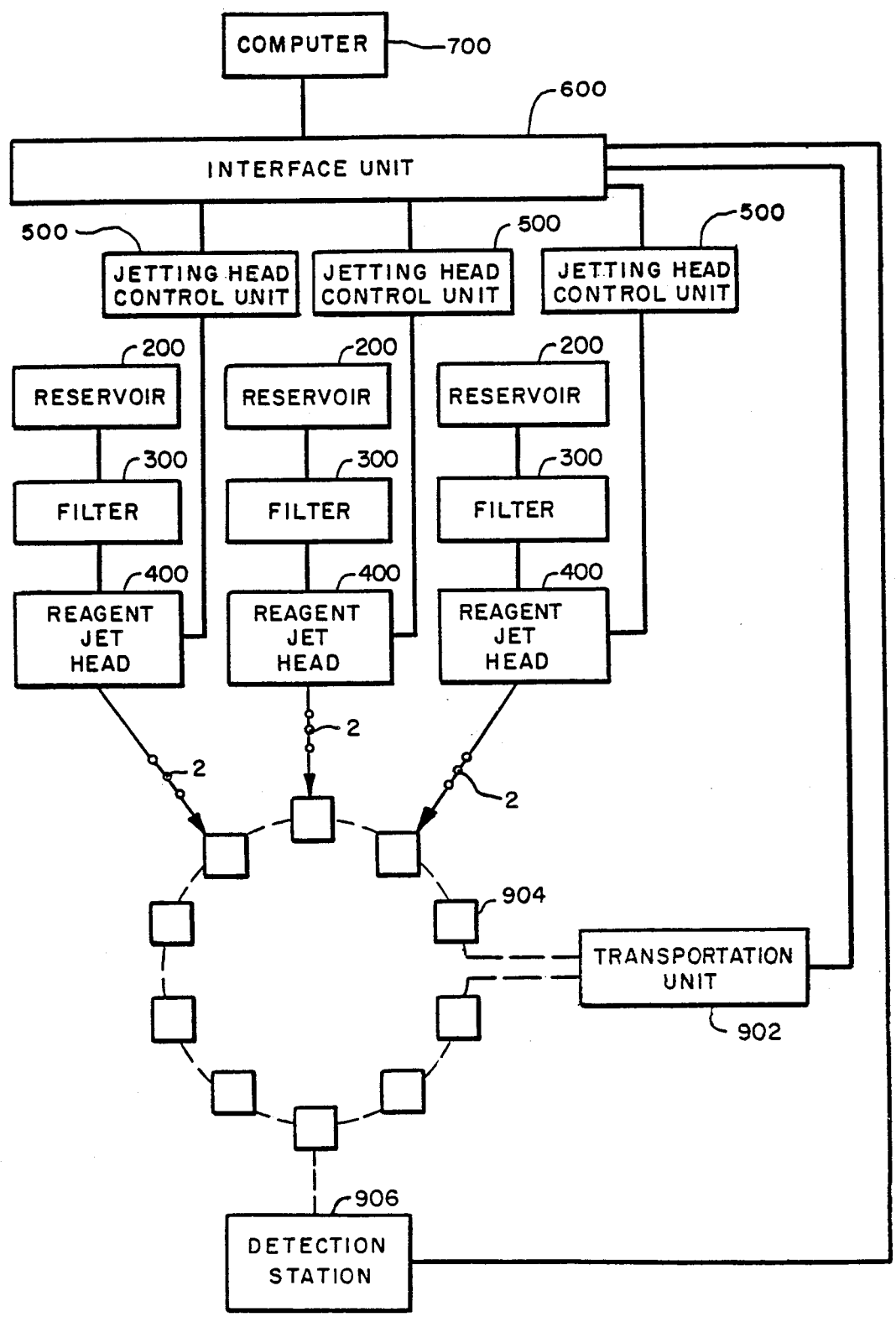

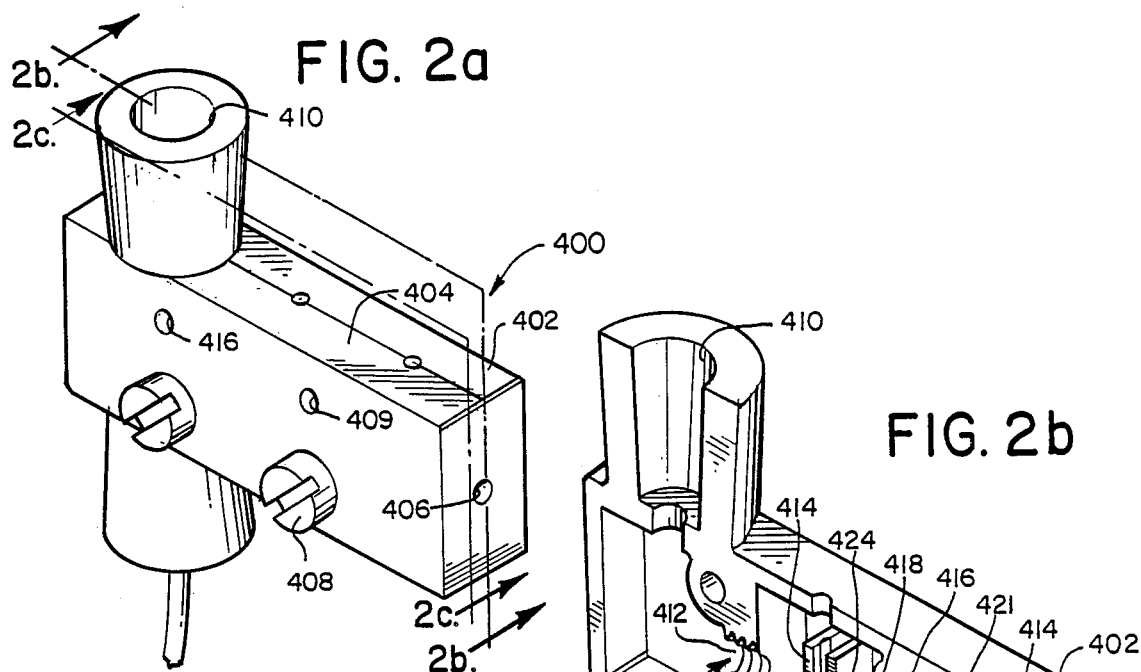
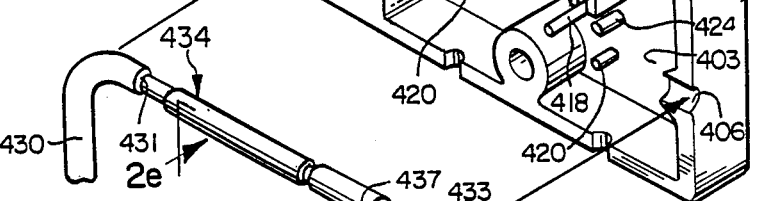
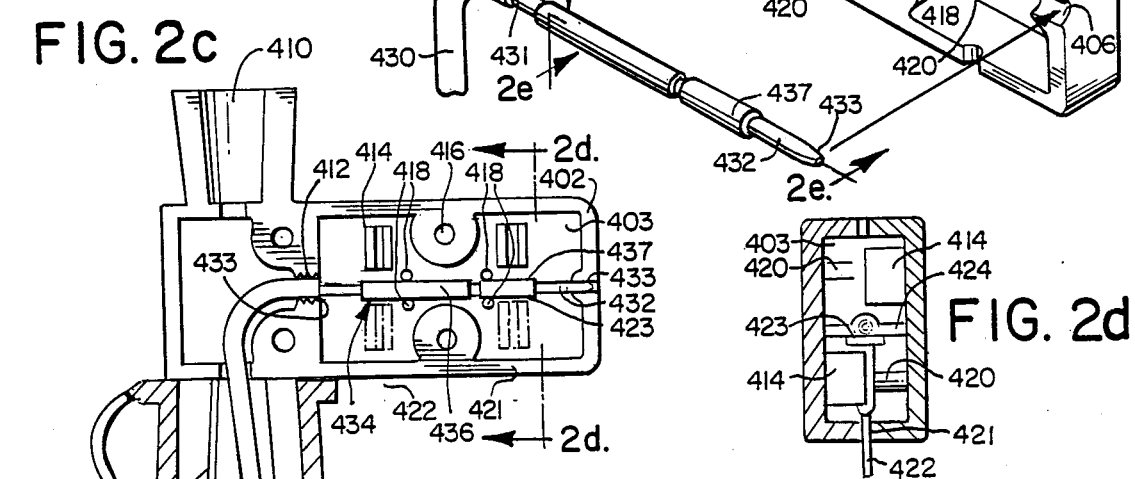
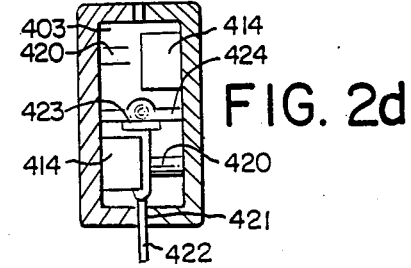
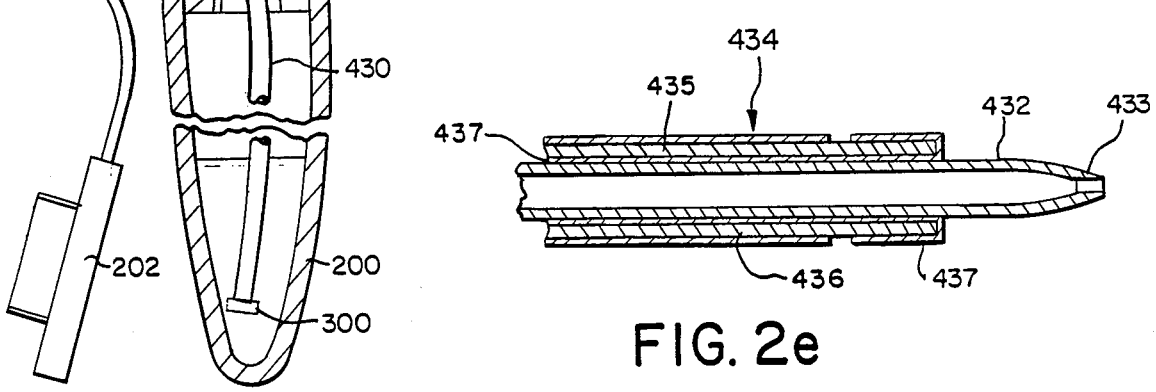

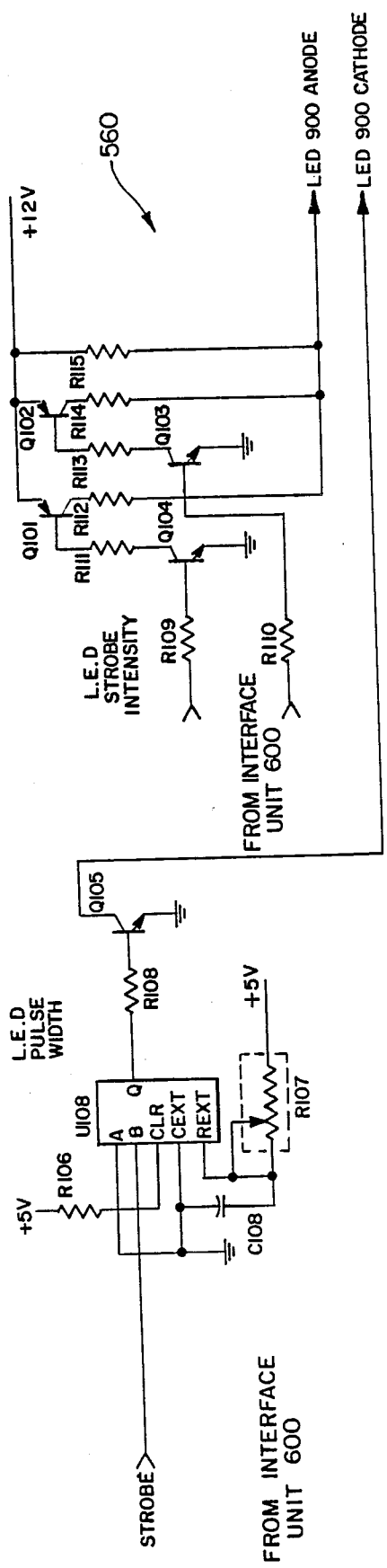
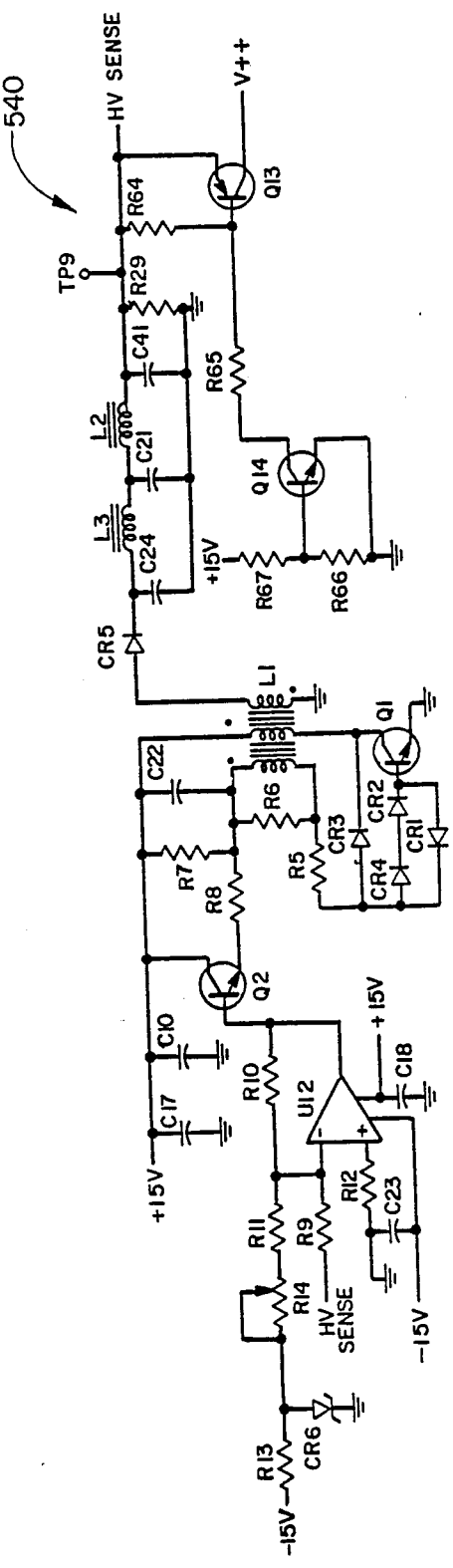
FIG. 5a
FIG. 5b

FIG. 5e
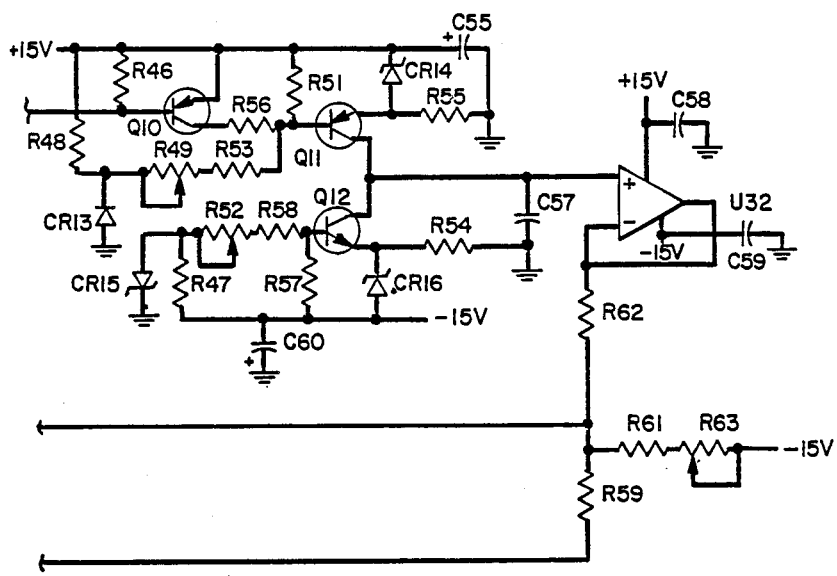
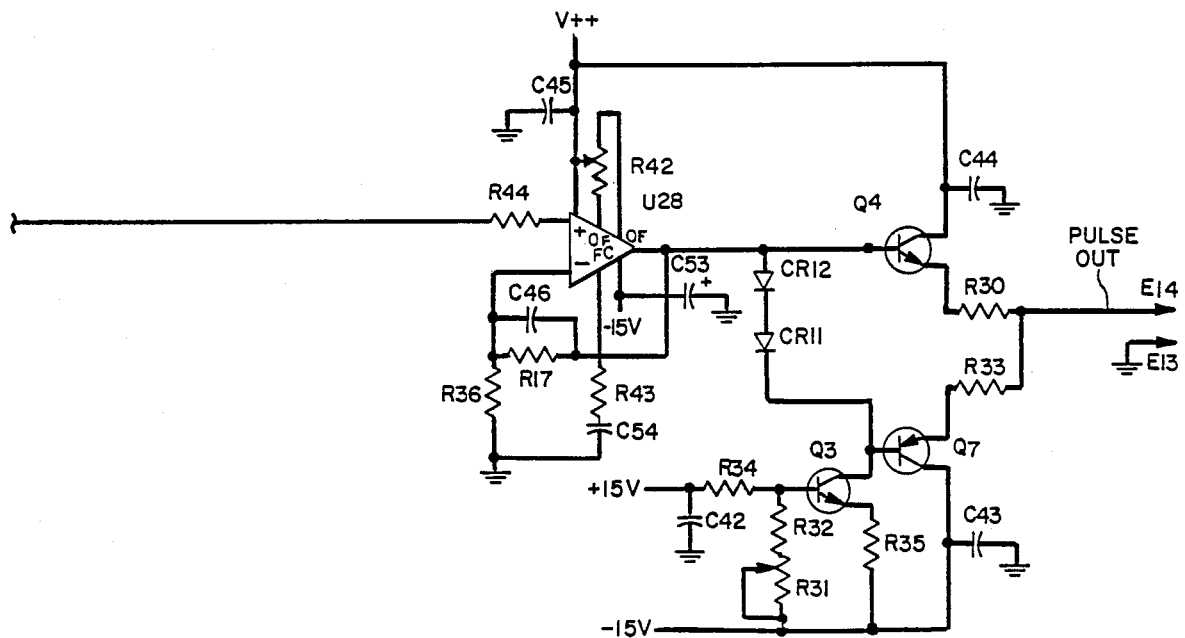

APPARATUS AND PROCESS FOR REAGENT FLUID DISPENSING AND PRINTING

This application is a continuation of application Ser. No. 06/931,476, filed Nov. 17, 1986, now abandoned.

BACKGROUND OF THE INVENTION

The present invention relates to an apparatus and process for dispensing and printing reagent fluids, wherein a transducer is used to propel small quantities of the fluid towards a positioned target.

Diagnostic assays often require systems for metering, dispensing and printing reagent fluids. In the case of metering and dispensing, such systems comprise both manual and automatic means. For purposes of practicality, the present background discussion will focus on the methods of metering and dispensing 100 micro-liter volumes or less.

The manual systems of metering and dispensing include the glass capillary pipet; the micro-pipet; the precision syringe; and weighing instruments. The glass capillary pipet is formed from a precision bore glass capillary tube. The pipet typically comprises a fire blown bulb and a tubular portion fire drawn to a fine point. Fluid is precisely metered by aspirating liquid through the tube into the bulb to a predetermined level indicated by an etched mark. The fluid may then be dispensed by blowing air through the tube.

The micro-pipet typically comprises a cylinder and a spring loaded piston. The travel of the piston is precisely determined by a threaded stop. The distance the piston travels within the cylinder and the diameter of the cylinder define a precise volume. The fluid is aspirated into and dispensed from the micro-pipet in precise quantities by movement of the piston within the cylinder.

The precision syringe generally comprises a precisely manufactured plunger and cylinder with accurately positioned metering marks. The fluid is introduced into and dispensed from the syringe by movement of the plunger between the marks.

Weighing techniques for dispensing fluids often simply involve weighing a quantity of fluid. The density of the fluid may then be used to determine the fluid volume.

Exemplary automatic metering and dispensing systems include the precision syringe pump; the peristaltic pump; and the high performance liquid chromatography (HPLC) metering valve. The precision syringe pump generally comprises a precision ground piston located within a precision bore cylinder. The piston is moved within the cylinder in precise increments by a stepping motor.

The peristaltic pump comprises an elastmeric tube which is sequentially pinched by a series of rollers. Often the tube is placed inside a semicircular channel and the rollers mounted on the outer edge of a disc driven by a stepping motor. The movement of the rollers against the tubing produces peristaltic movement of the fluid.

The HPLC metering valve comprises a defined length of precision inner diameter tubing. The fluid is introduced into the defined volume of the tubing with the valve in a first position and then dispensed from the tubing when the valve is placed in a second position.

All of the above metering and dispensing systems have the disadvantage that the volumes dispensed are relatively large. Furthermore, these systems are also relatively slow, inefficient and comprise precision fitted components which are particularly susceptible to wear.

The printing of reagent fluids is frequently required in the manufacture of chemical assay test strips. Selected reagents are printed in a desired configuration on strips of filter paper. The strips may then be used as a disposable diagnostic tool to determine the presence or absence of a variety of chemical components.

Generally, to perform a chemical assay with a test strip, the strip is exposed to a fluid or a series of fluids to be tested, such as blood, serum or urine. In some instances, the strip is rinsed and processed with additional reagents prior to being interpreted. The precise interpretation depends on the type of chemical reactions involved, but may be as simple as visually inspecting the test strip for a particular color change.

The manufacture of test strips generally involves either a printing process or a blotting process. The blotting process is the simplest manufacturing method and permits most reagents to be applied without modification. A disadvantage of this process is that it is difficult to blot the fluids onto the test strip with precision.

The printing process will often involve any of three well known methods silk screening; gravure; and transfer printing. The silk screening of reagents generally involves producing a screen by photographic methods in the desired configuration for each reagent to be printed. The screen is exposed under light to a preselected pattern and then developed. The areas of the screen which are not exposed to light, when developed, become porous. However, the areas of the screen which have been exposed to light remain relatively nonporous. The screen is then secured in a frame and the test strip placed below. The desired reagent fluid, specially prepared to have a high viscosity, is spread over the top side of the screen. The reagent passes through the porous areas of the screen and onto the test strip. The test strip is then subjected to a drying process, specific to each reagent. Once the test strip is dry, it may be printed again using a different screen, pattern and reagent.

The gravure method of printing reagents comprises coating a metal surface with a light sensitive polymer. The polymer is exposed to light in the desired predetermined pattern. When developed, the polymer creates hydrophilic and hydrophobic regions. The reagent is specially prepared such that when applied to the metal it will adhere only to the hydrophilic regions. After the specially prepared reagent is applied, the test strip is pressed against the metal and the reagent is transferred from the metal to the test strip.

The transfer printing method comprises transferring the reagents from a die to the test strip in the desired pattern. The die is made with the appropriate pattern on its surface and then coated with the desired, specially prepared reagent. A rubber stamp mechanism is pressed against the die to transfer the reagent in the desired pattern from the die to the rubber stamp. The rubber stamp is then pressed against the test strip to transfer the reagent, in the same pattern, to the test strip.

Each of the above-mentioned reagent printing techniques has significant disadvantages. The most common disadvantage is the requirement that the reagents must be specially prepared. Additionally, if a variety of reagents are to be printed onto a single test strip, the strip must be carefully aligned prior to each printing. This alignment procedure increases the cost and decreases the throughput of the printing process. Moreover, a special die or screen must be produced for each pattern to be printed. A further disadvantage arises in that the above printing methods are unable to place reproduceable minute quantities of reagent on the test strip.

It is an object of the present invention to provide a printing and dispensing method and apparatus which avoids these disadvantages.

SUMMARY OF THE PRESENT INVENTION

The present invention is directed to a reagent dispensing and printing apparatus and method, wherein the apparatus comprises a transducer operative to eject a substantially uniform quantity of reagent in a precise predetermined direction.

According to one preferred embodiment of the present invention used in dispensing reagent fluids, a jetting tube is concentrically located within a piezoelectric transducer. The jetting tube comprises an orifice at one end and a reagent receiving aperture at the other end. The receiving end of the jetting tube is connected to a filter which is in turn connected to a reservoir containing a selected reagent. A jetting control unit supplies an electrical pulse of short duration to the transducer in response to a command issued by a computer. The electrical pulse causes the volume defined by the jetting tube to expand by an amount sufficient to intake a small quantity of reagent fluid from the reservoir. At the end of the pulse duration, the transducer de-expands propelling a small quantity of the reagent fluid through the orifice and into a fluid recepticle. If desired, additional droplets may be deposited in the recepticle or the recepticle aligned with an additional jetting tube for receiving an additional reagent fluid.

An additional preferred embodiment of the present invention may be used for printing reagent fluids onto a print medium. In this embodiment, the jetting tube is aligned with the printing medium such that the propelled droplet impacts a precise position on the medium. The jetting tube or print medium may then be repositioned and another droplet expelled from the jetting tube. The process may be repeated until a desired configuration of the reagent fluid is printed on the medium.

One advantage of the present invention is that precise minute quantities of reagent fluid may be dispensed or printed in a reproducible manner. Additionally, the method and apparatus may be used to emit droplets of fluids having a wide range of reagent fluid viscosities and surface tensions. The reagents do not in general have to be specially adapted for use with the present invention.

The invention itself, together with further objects and attendant advantages, will best be understood by reference to the following detailed description, taken in conjunction with the accompanying drawings.

BRIEF DESCRIPTION OF THE DRAWINGS

FIG. 1 is a schematic representation of a first preferred embodiment of the present invention showing the use of multiple jetting heads to meter and dispense reagent fluids.

FIG. 2a is a perspective view of a first preferred embodiment of the jetting head of the present invention.

FIG. 2b is a cut-away perspective view of the preferred embodiment of FIG. 2a taken along lines 2b-2b with the contact pins removed.

FIG. 2c is a sectional representation of the preferred embodiment of FIG. 2a taken along lines 2c—2c.

FIG. 2d is a sectional representation of the preferred embodiment of FIG. 2c taken along lines 2d—2d.

FIG. 2e is a sectional representation of the jetting tube and transducer of the preferred embodiment of FIG. 2b taken along lines 2e—2e.

FIG. 5a is a schematic representation of a portion of the jetting head control unit showing the LED strobe circuit.

FIG. 5b is a schematic representation of a portion of the jetting head control unit showing the high voltage power supply circuit.

FIG. 5e is a schematic representation of a portion of the jetting head control unit showing an additional portion of the pulse generator.

FIG. 6b is an exploded view of the preferred embodiment of FIG. 6a.

DETAILED DESCRIPTION OF THE PRESENTLY PREFERRED EMBODIMENTS

Figure 3:
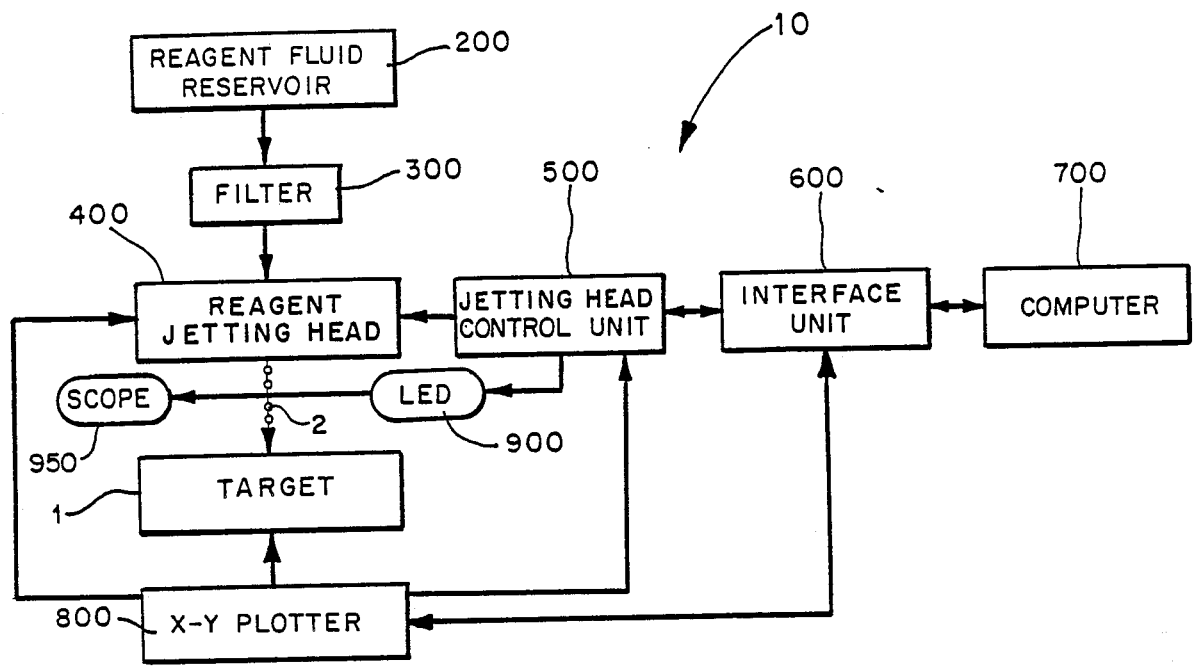
FIG. 3 is a schematic representation of a second preferred embodiment operating in the drop on demand mode as a reagent printing system.

Turning now to the drawings, FIG. 1 shows a schematic representation of a first preferred embodiment of a reagent dispensing system generally represented as reference numeral 30. The dispensing system 30 comprises a plurality of reagent fluid reservoirs 200, a plurality of filters 300, a plurality of reagent jetting heads 400, a plurality of jetting head control units 500, an interface unit 600, a computer 700, transportation unit 902, a plurality of fluid mixing cells 904 and a detection station 906.

The reservoir 200 holds a selected quantity of reagent fluid for dispensing. The reservoir 200 is maintained at atmospheric pressure by suitable means such as an atmospheric vent. The reagent fluid is transferred from the reservoir 200 through the filter 300 to the reagent jetting head 400. The filter 300 is placed between the reservoir 200 and the jetting head 400 to ensure that any particulate foreign matter in the reagent fluid is trapped before entering the jetting head 400.

The plurality of jetting heads 400 and the detection station 906 define a processing path. Each jetting head 400, which is described in detail below, ejects uniformly sized droplets 2 of reagent fluid. The droplets 2 are propelled, with controlled velocity and direction, towards a selected mixing cell 904 positioned along the processing path by the transportation unit 902. The mixing cells 904 are comprised of nonreactive material and function as minute holding tanks for the dispensed reagent fluid.

The plurality of jetting heads 400, shown in FIG. 1, are positioned sequentially along the processing path. Alternately, some or all of the plurality of jetting heads 400 may be positioned with respect to the transportation unit 902 such that the heads 400 direct the droplets 2 into a selected mixing cell 904 simultaneously.

The jetting heads 400 and the transportation unit 902 are controlled by the computer 700. The computer 700 issues commands to an interface unit 600 which is electrically connected to the transportation unit 902 and to the jetting head control unit 500. The interface unit 600 is of conventional design and is used to control the transfer of information between the computer 700 and the jetting control unit 500. The interface unit 600 is also used to control the transfer of information between the computer 700 and the transportation unit 902.

Figure 4:
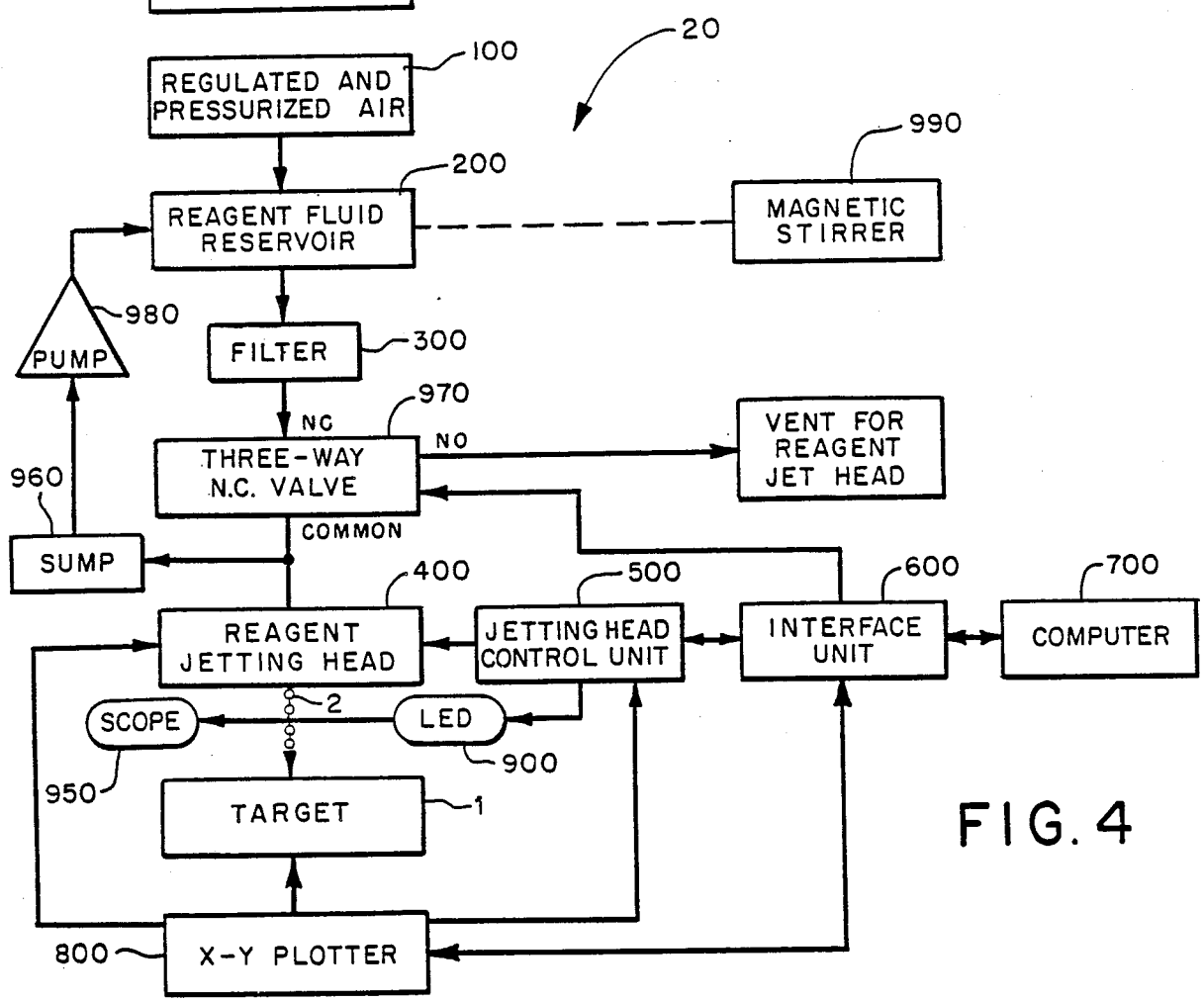
FIG. 4 is a schematic representation of a third preferred embodiment operating in the continuous mode as a reagent printing system.

A first embodiment of the reagent jetting head is shown in FIGS. 2a-2e and generally represented by numeral 400. The jetting head 400 comprises a two piece symmetrical housing 402, 404. The housing 402, 404, when assembled, is adapted to form an orifice aperture 406, an air vent and reagent supply channel 410 and a transducer chamber 403, shown in FIG. 4b. Four screws 408, adapted to respective housing screw apertures 416, hold the housing 402, 404 in an assembled configuration.

The jetting head 400 further comprises a jetting tube 432, a piezo-electric transducer 434 and a reagent fluid supply tube 430. The jetting tube 432 defines a tapered orifice 433 at one end and a fluid receiving aperture 431 at the other end for expelling and receiving fluid, respectively. The piezo-electric transducer 434 is cylindrically shaped and secured concentrically about the mid-region of the jetting tube 432 with epoxy or other suitable means.

The piezo-electric transducer 434, shown in FIG. 2e, defines a first and second end and comprises a section of cylindrically shaped piezo-electric material 435. An inner nickel electrode 437 covers the inner surface of the cylinder 435. The electrode 437 wraps around the first end of the cylinder 435 a sufficient distance to enable electrical connection external to the cylinder 435.

A second nickel electrode 436 covers the majority of the outer surface of the cylinder 435. The second electrode is electrically isolated from the first electrode 437 by an air gap at the face of the second end of the cylinder 435 and by an air gap on the outer surface of the cylinder 435 near the first end. When an electrical pulse is applied to the first and second electrodes 437, 436 a voltage potential is developed radially across the transducer material 435. The voltage potential causes the radial dimensions of the transducer 435 to change, which causes the volume defined by the transducer 434 to also change.

The jetting tube 432 is positioned in the transducer chamber 403 such that the receiving end 431 extends beyond the rearward end of the transducer 434. The receiving end 431 of the jetting tube 432 is inserted into one end of a reagent supply tube 430. The supply tube 430 is sealingly held to the jetting tube 432 by concentric teeth 412 formed by the housing sections 402, 404. The teeth 412 not only seal the supply tube 430 to the jetting tube 432, but, also, seal the supply tube 430 to the housing 402, 404.

The second end of the supply type 430 passes through the channel 410 and into a reagent reservoir 200. The reservoir 200 contains the reagent fluid to be dispensed by the jetting head 400. As the reagent fluid is dispensed, air is supplied to the reservoir 200 through the channel 410 to prevent the creation of a vacuum in the reservoir 200. The reservoir 200 is releasably attached to the housing 402, 404 and held in place by frictional forces. A reservoir cap 202 is flexibly attached to the reservoir 200 and adapted such that the cap 202 may be used to secure the opening in the reservoir 200 when the reservoir 200 is disengaged from the housing 402, 404.

The position of the jetting tube 432 defines the horizontal plane of the jetting head 400. The jetting tube 432 and the transducer 434 are held in a predefined vertical relationship with respect to the housing 402, 404 by means of two upper vertical alignment pins 418 and two lower vertical alignment pins 418. The two upper vertical alignment pins 418 extend horizontally from the housing section 402 into the transducer chamber 403. Similarly, the two lower vertical alignment pins 418 extend horizontally from the housing section 404 into the transducer chamber 403. Each vertical alignment pin 418 is formed integrally with the respective housing sections 402, 404.

The jetting tube 432 and the transducer 434 are held in a predefined horizontal relationship with respect to the housing 402, 404 by means of four horizontal alignment pins 424. Two of the horizontal alignment pins 424 extend horizontally from the housing section 402 approximately midway into the transducer chamber 403. Similarly, two of the horizontal alignment pins 424 extend horizontally from the housing section 404 approximately midway into the transducing chamber 403. Each horizontal alignment pin 424 is formed integrally with the respective housing section 402, 404. The alignment pins 418, 424, sealing teeth 412 and orifice aperture 406 are aligned and adapted to hold the jetting tube 432 and transducer 434 such that the orifice 433 of the jetting tube 432 extends into the orifice aperture 406.

An electrical transducer activation pulse is supplied to the piezo-electric transducer 434 from the jetting head control unit 500 by means of two contact pins 422. A quantity of fluid will be dispensed from the jetting tube for each applied activation pulse. The activation pulse can be produced by a variety of conventional circuits or commercially available units. Therefore a detailed description of such a circuit will not be provided. However, a circuit for producing a series of activation pulses is provided in the description of the printing embodiment below. Due to the differing constraints involved in dispensing and printing, the circuit in the printing embodiment is not required to produce only a single pulse. However, one skilled in the art could, if desired, modify the circuit to produce a single pulse on demand for use in the dispensing embodiment.

Each contact pin 422 defines an enlarged head 423 which is adapted to contact the respective first and second electrodes 437, 436 located on the outer surface of the transducer 434. Two contact pin holders 414, integral with the housing 402, 404, are positioned to hold the respective contact pins 422 under the pin heads 423 such that each pin head 423 electrically engages the appropriate electrode 437, 436 of the transducer 434. Two contact pin engaging posts 420 extend from the housing 402, 404 opposite the contact pin holders 414 to engage and hold the contact pins 422 against the contact pin holders 414. The ends of the contact pins 422 opposite the pin heads 423 extend through the housing 402, 404 by means of contact pin apertures 421. Since the housing sections 402, 404 are formed symmetrically to one another, the contact pins 422 may be optionally attached above the transducer 434.

In operation, the reservoir 200 containing reagent fluid is fastened to the jetting head 400 such that the fluid supply tube 430 extends into the reagent fluid. The filter 300 may be fitted to the free end of the supply tube 430 or positioned inside the reservoir 200. Air is supplied through the channel 410 around the supply tube 430 to prevent the reservoir 200 from falling below atmospheric pressure. The air is prevented from entering around the supply tube 430 and into the transducer chamber 403 by the seal created between the sealing teeth 412 and the supply tube 430. The jetting tube 432 may be primed by slightly pressurizing the reservoir 200 to cause the reagent fluid to travel through the supply tube 430 and into the jetting tube 432. Once primed, the fluid is prevented from substantially withdrawing from the jetting tube 432 by the surface tension of the reagent fluid at the orifice 433.

The transducer activation pulse is conducted to the contact pins 422 of the jetting head 400. The contact pins 422 communicate the high voltage pulse to the electrodes 437, 436 of the transducer 434 with polarity such that the concentrically mounted transducer 434 expands. The rate of expansion is controlled by the rise time of the high voltage pulse which is preset to generate a rapid expansion. The expansion of the transducer 434 causes the jetting tube 432, which is epoxied to the transducer 434, to also expand. The expansion of the tube 432 generates an acoustic expansion wave interior to the tube 432 which travels axially towards the orifice 433 and towards the fluid receiving aperture 431. When the expansion wave reaches the orifice 433, the reagent fluid is partially drawn inwardly. However, the surface tension of the fluid acts to inhibit substantial inward fluid movement.

When the expansion wave reaches the end 431 of the tube 432, the expansion wave is reflected and becomes a compression wave which travels towards the center of the piezo-electric tube 434. The high voltage pulse width is adapted such that when the reflected compression wave is beneath the piezo-electric tube 434, the high voltage pulse falls, resulting in a de-expansion of the transducer 434 and the jetting tube 432. This action adds to the existing acoustic compression wave in the interior of the jetting tube 432. The enhanced compression wave travels toward the orifice causing reagent fluid to be dispensed from the tube 432. The fluid is propelled from the orifice 433 as a small droplet 2 and deposited in the selected mixing cell 904 positioned by the transportation unit 902. One droplet 2 is dispensed for each transducer activation pulse. This mode of dispensing is referred to as the drop on demand mode.

In some instances, the droplet 2 may be accompanied by at least one smaller satellite droplet. However, even if satellite droplets are present, the volume and velocity of the reagent droplets 2 are highly reproduceable. This reproducibility allows for precise dispensing of uniform, controllably sized droplets 2 of reagent fluid into the mixing cell 904.

The droplets 2 of reagents impact the mixing cell 904 with sufficient force and volume to cause fluidic mixing of the reagents. Once the desired amounts of the selected reagents are deposited in the selected mixing cell 904, the mixing cell 904 is transported to the detection station 906 where the mixed reagents may be extracted for use or analyzed for assay results.

The dispensing system 30 provides numerous advantages based upon the ability of the reagent jetting head 400 to rapidly and reproduceably eject uniform quantities of a wide range of reagents. The ability of the dispensing system 30 to dispense minute amounts of reagents reduces the processing time of certain chemical assays. Furthermore, some chemical assays require a wide range of dilution ratios. Many conventional dispensing systems are unable to dispense the reagents in volumes small enough to make the desired assay practical. The dispensing system of the present invention overcomes this disadvantage.

In addition to dispensing reagent fluids, certain embodiments may be used for precision printing of reagents onto a printing medium such as filter paper to produce an assay test strip. A printing system 10 using the present invention is represented in FIG. 3. Structure similar in form and function to structure described above will be designated by like reference numerals. The printing system 10 comprises a reagent fluid reservoir 200, a filter 300, a reagent jetting head 400, a jetting head control unit 500, an interface 600, a computer 700, and an x-y plotter 800.

The x-y plotter 800 is a commercially available pen plotter, mechanically modified in a conventional manner such that the pen is replaced with the jetting head 400. The general operation and structure of the plotter 800 will not be described in detail. The plotter 800 accepts commands from the computer 700 thru a standard RS-232 serial interface contained within the interface unit 600. The plotter 800 processes the commands and produces control signals to drive an x-axis motor (not shown) and a y-axis motor (not shown). The x-axis motor is used to position the jetting head 400 and the y-axis motor is used to position the printing target 1.

The plotter 800 produces a pen down signal PENDN. This signal is applied to the control unit 500 and indicates that the plotter 800 is ready to begin a printing operation.

The control unit 500 also receives control signals from the interface unit 600. These signals include signals HIGHER*, LOWER* to control the magnitude of the pulse applied to the transducer 434; a reset signal RST to reset the control unit 500; and a series of print signals PRT*. The generation of these signals will not be described in detail since there production is performed by the conventional interface unit 600.

The jetting head 400 and fluid supply system 200, 300 are initialized and operate substantially as described above. The jetting head control unit 500, shown in FIGS. 5a–5e comprises a print control circuit 510, a pulse generator 530, a high voltage supply 540, and a strobe pulse generator 560. The control unit 500 also comprises a power supply. However, since the power supply is of conventional design it will not be shown or described in detail.

The print control circuit 510 receives the pen down signal PENDN from the plotter 800 and comprises a transistor Q100, a one-shot circuit U100, two NANDgates U101, U102, a line decoder multiplexer U107 and four inverters U103-U106. The pen down signal PENDN is applied to the base of the transistor Q100 by resistors R100, R101 and diode D100. The emitter of transistor Q100 is tied to ground and the collector is connected to the −5 volt supply by resistor R102.

The one-shot U100 comprises inputs A, B and an output Q. The B input of the one-shot U100 is connected to the collector of the transistor Q100 and the A input is tied to ground. The time period of the pulse produced by the one-shot U100 is determined by a resistor R104, a variable resistor R105 and a capacitor C100. The output Q of the one-shot U100 is combined with the collector output of the transistor Q100 by the NAND-gate U101 and then inverted by the NAND-gate U102. The circuit is operative to produce an adjustable delay in the application of the pen down signal PENDN to the control unit 500.

The line decoder U107 is circuited to function as a 3 input AND-gate. The output of the NAND-gate U102 is applied to the first input of the decoder U107; the print signal line PRT* comprising a series of pulses from the interface unit 600 is applied to the second input; and a jetting head ON/OFF signal from switch S1 is applied to the third input. The inverter U106 inverts the output of the line decoder U107 to generate the print control signal PRT* and the inverters U103-U105 invert the control signals LOWER*, HIGHER*, and RST signals, respectively.

The high voltage supply 540, shown in FIG. 5b, provides +175 volts DC to produce a maximum pulse of 150 volts peak to peak at the reagent jetting head 400. The high voltage supply 540 comprises differential amplifier U12 and transistors Q1, Q2, Q13, Q14. A stable reference voltage of −2.5 volts DC is produced at the junction of a resistor R13, connected to the −15 volt supply, and a diode CR6, connected to ground. The reference voltage is combined with a resistor R14 to produce an adjustable, stable voltage reference for the amplifier U12. The reference voltage is applied to the inverting input of the amplifier U12 through a resistor R11. The noninverting input of the amplifier U12 is connected to ground by a resistor R12. The amplifier U12, in combination with a feedback resistor R10, produces an output signal proportional to the difference of the voltage reference signal and the ground potential.

The output of the amplifier U12 is applied to the base of the transistor Q2 whose collector is connected to the +15 volt supply. The signal produced at the emitter of the transistor Q2 is applied to the base of the transistor Q1 through resistors R8, R6, R5, a transformer L1 and diodes CR4, CR2, CR1. The emitter of the transistor Q1 is connected to ground and the collector is connected to the +15 voltage supply through the transformer L1. A diode CR3 connects the collector of the transistor Q1 to the junction of the resistor R5 and the diode CR. The transistor Q1 is biased for proper operation by resistors R7, R6, R5. The resistor R7 and a capacitor C22 connect the junction of the resistor R8, R6 to the +15 voltage supply.

The transistor Q1 and the transformer L1 form a "flyback" blocking oscillator. Any increase in current supplied by the transistor Q1 produces an increase in energy transferred through the secondary winding of the transformer L1 and diode CR5. Therefore, an increase in current supplied by the transistor Q1 results in an increase in power available to the high voltage output. The diodes CR1–CR4 form a "Baker clamp" which prevents transistor Q1 from saturating. The clamp thereby avoids transistor storage time.

The diode CR5 is connected to a multiple pi filter formed by the inductors L3, L2, capacitors C24, C21, C41 and resistor R29. The multiple pi filter attenuates ripple and switching spikes in the signal supplied to the transistor Q13 which produces the high voltage output V. A resistor R64 connects the base of the transistor Q13 to the emitter and to the resistor U29. The base is also connected to the collector of the transistor Q14 by a resistor R65. The base of the transistor Q14 is connected to the +15 volt supply by a resistor R67 and to ground by a resistor R66. The emitter of the transistor Q13 provides a signal HV SENSE which is fed back to the inverting input of the amplifier U12 through a resistor R9. The high voltage output V++ is produced at the collector of the transistor Q13. The proper biasing of the transistor Q13 is provided by resistor R64 and the biasing circuit comprising the transistor Q14, resistors R67, R66, R65.

Figure 5C:
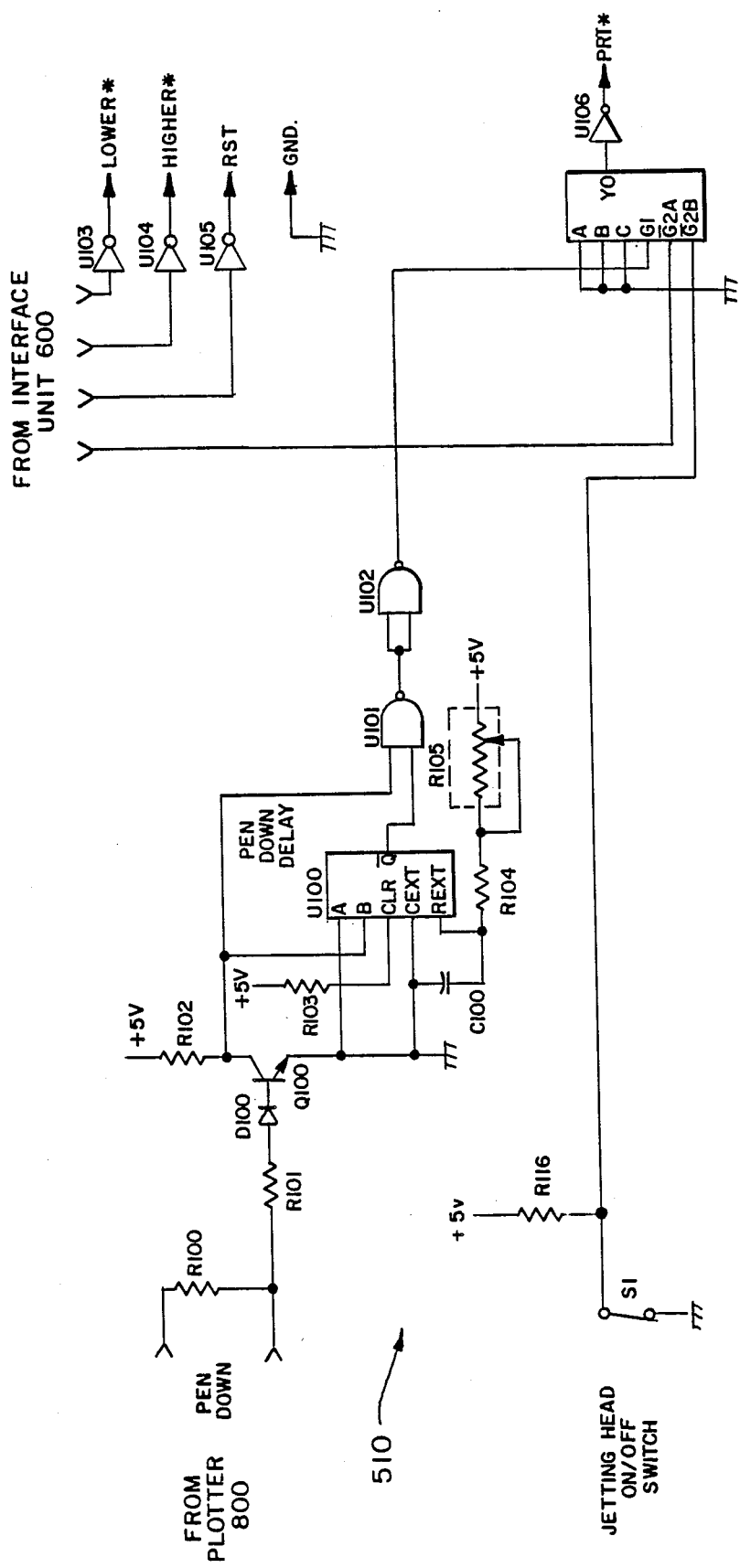
FIG. 5c is a schematic representation of a portion of the jetting head control unit showing the print control circuit.
Figure 5D:
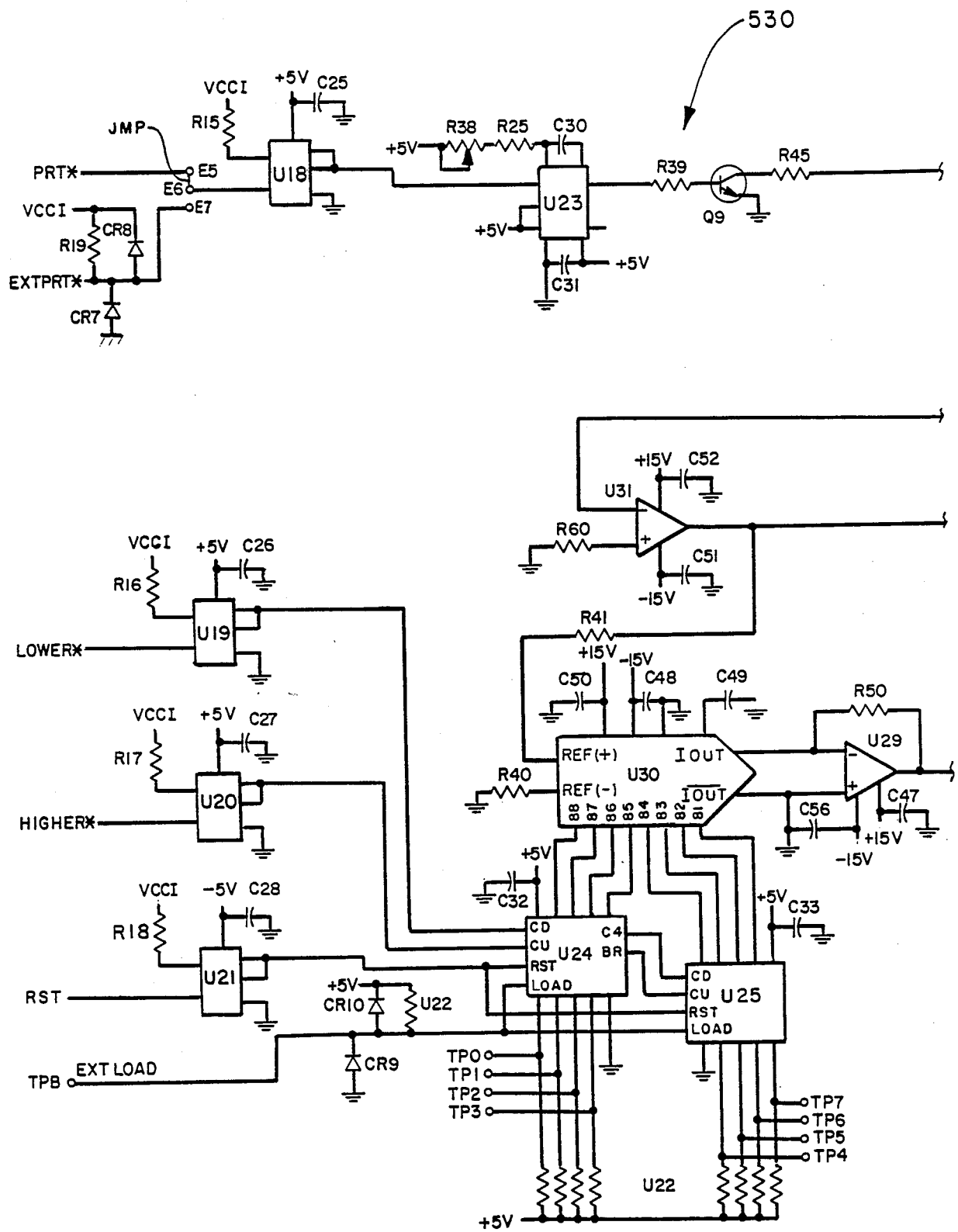
FIG. 5d is a schematic representation of a portion of the jetting head control unit showing a portion of the print pulse generator.

The pulse generator 530, shown in FIGS. 5d, 5e, comprises an opto-isolator U18, a one-shot U23, a digital to analog (D/A) converter U30 and two binary counters U24, U25. The pulse generator 530 accepts control signals PRT*, LOWER*, HIGHER*, RST and produces the activation pulse which is applied to the transducer 434. In normal operation, the PRT* control signal is supplied to the opto-isolator U18 by a jumper JMP between contact points E5, E6. The opto-isolator U18 is of conventional design and comprises a light emitting diode (LED) circuit and a photo-element circuit. A resistor R15 operates as the load resistor for the LED circuit of the isolator and a capacitor C25 suppresses transient noise on the voltage supply to the isolator U18. The output of the isolator U18 is applied to one input of the one-shot U23 whose time constant is adjustably determined by resistors R38, R25 and a capacitor C30. The pulse from the non-inverting output of the one-shot U23 is fed to the base of a transistor Q9. A resistor R39 sets the approximate base current of the transistor Q9 which is used as a level shifter for converting the CMOS signal level to the +15 volt DC signal level.

The control of the rise and fall rates of the pulse generator 530 is accomplished by directing a pair of current source transistors Q11, Q12 to charge and discharge a capacitor C57. The transistor Q11 is operative as a source of current and the transistor Q12 is operative as a sink for current. A transistor Q10 controls the level of the current by applying an appropriate bias current through a resistor R56 to the base of the transistor Q11. The biasing of the transistors Q11, Q12 is critical to the proper rise and fall rates. Therefore precision voltage references CR13, CR15 are used to provide respective bias reference voltages. A temperature compensation network is formed from zener diodes CR14, CR16 and resistors R55, R54 to maintain stable operation of the transistors Q11, Q12, respectively. The variable resistors R49, R52 may be used to adjust the fall time and rise time, respectively, of the output pulse applied to the reagent jetting head 400. A plurality of resistors R45, R46, R47, R48, R49, R51, R52, R53, R56, R57, R58 are used to properly bias the transistors Q10, Q11, Q12 and capacitors C55, C60 are circuited to maintain stability of the circuit.

The impedance of the output stage of the rise and fall circuitry Q10, Q11, Q12 is very high. With such a high impedance, circuit elements attached to the capacitor C57 could affect the linearity of the rise and fall time constants. Therefore, an FET input operational amplifier U32 is used as an impedance interface. The amplifier U32 is configured in the noninverting mode and circuited with capacitors C58, C59 for stability.

The output of the amplifier U32 is applied to an inverting amplifier U31 by means of a resistor R62. The amplifier U31 inverts and conditions the pulse control signal with the aid of resistors R59, R60. Resistors R61, R63, connected to the −15 voltage supply, provide a means for adjusting the DC level offset of the amplifier U31 output signal. Capacitors C51, C52 are connected to enhance the performance and stability of the circuit.

The output of the amplifier U31 is applied by means of a resistor R41 to the positive voltage reference signal input REF(+) of the D/A converter U30. The negative voltage reference signal input REF(−) is tied to ground by a resistor R40. The D/A converter U30 produces output signals IOUT, IOUT* which are proportional to the difference between the positive and negative voltage reference signal inputs REF(+), REF(−). Capacitors C48, C49, C50 are connected to the D/A converter U30 to enhance stability.

The D/A converter outputs IOUT, IOUT* are also proportional to an 8-bit binary value applied to inputs B1–B8. The binary value is supplied by the counters U24, U25 which are controlled by the function signals LOWER*, HIGHER* and RST. The LOWER* signal and the HIGHER* signals are applied to the count up and count down inputs CU, CD of the counter U24 by means of opto-isolators U19, U20. The carry and borrow outputs CY, BR of the counter U24 are connected with the count up and count down inputs CU, CD of the counter U25. The reset inputs RST of both counters U24, U25 receive the RST signal by means of an opto-isolator U21. Resistors R16, R17, R18 are used as load resistors for the LED circuits of the isolators U19, U20, U21 and capacitors C26, C27, C28 are used to enhance the stability of the isolator circuits.

The counters U24, U25 may optionally be preloaded to the selected 8-bit binary value through input lines TP0–TP7. The input lines TP0–TP7 are normally biased to the logical high signal state by resistive network U22. The selected binary value is loaded into the counters U24, U25 by pulling the respective inputs TP0–TP7 low and applying an external, active low, load signal EXT LOAD to pin TP8. The load signal pin TP8 is connected to the load inputs LOAD of the counters U24, U25 and conditioned by a clipping circuit comprised of diodes CR9, CR10 and a pull-up resistor of the resistor network U22.

The noninverted and the inverted outputs IOUT, IOUT* are connected to the inverting and noninverting inputs of a differential amplifier U29. The output of the amplifier U29 is fed back to the inverting input by a resistor R50. The amplifier U29 converts the current output of the D/A converter U30 to a voltage output. Capacitors C56, C47 are provided to enhance circuit stability.

The output of the amplifier U29 is applied to the noninverting input of the amplifier U28. The output of the amplifier U28 is fed back to the inverting input by means of a capacitor C46 and a resistor R37. The inverting input is also connected to ground by a resistor R36. To enhance the frequency response of the amplifier U28, a resistor R43 and a capacitor C54 are connected between the frequency compensation input FC and ground. An adjustable DC offset is provided by connecting the output offset inputs OF, OF with a variable resistor R42. The wiper of the resistor R42 is connected to the high voltage power supply output V++.

The output of the amplifier U28 is also connected to the base of a transistor Q4 and through diodes CR11, CR12 to the base of a transistor Q7. The transistor Q4, Q7, Q3 and resistors R30–R35 form an output circuit capable of driving high capacitive loads at high slew rates and wide bandwidth. The variable resistor R31 may be used to set the maximum current through the bias network R30, R33 by measuring the voltage drop across resistor R35.

The strobe generator 560 produces a strobe pulse and comprises transistors Q101–Q105 and a one-shot circuit U108. The strobe intensity is determined by the circuit comprising the transistors Q101–Q104 and resistors R109–R115. The circuit is connected to the anode of the LED 900 and receives two inputs from the interface unit 600 to produce four levels of light intensity in the LED 900.

The activation and duration of activation of the LED 900 is determined by the one-shot U108 and the transistor Q105. The one-shot U108 comprises inputs A, B and an output Q. The strobe signal STROBE is applied to the B input from the interface unit 600. The duration of the one-shot U108 output pulse is controlled by the adjustable RC network R107, C108. The output Q is applied to the base of the transistor Q105 by resistor R108. The collector of the transistor Q105 is connected to the cathode of the LED 900 to draw current through the LED 900.

The computer 700, control unit 500 and plotter 800 must be initialized. The initialization of the computer 700 and the plotter 800 will not be discussed since these units are of conventional design and operation.

To initialize the jetting head control unit 500, the computer 700 directs the interface unit 600 to issue a reset command. The reset signal RST is conducted to the control unit 500 whereupon the counters U24, U25 are cleared. The computer 700 then retrieves from its memory, or by conventional operator input, the desired digital setting for the D/A converter. This setting may also be calculated from data and may be tailored to specific sizes of jetting heads 400 or reagent fluids. The computer 700 then issues a series of commands, through the interface unit 600, to increment or decrement the counters U24, U25 to correspond to the desired binary setting. If the command directs that the counters are to be raised, then the HIGHER* signal is applied through the opto-isolator U20 to the count up CU input of the counter U24. Similarly, if the command directs that the counters are to be lowered then the LOWER* signal is applied through the opto-isolator U19 to the count down CD input of the counter U24. Since the carry and borrow outputs CY, BR of the counter U24 are connected to the count up and count down inputs CU, CD, respectively, of the counter U25, the digital setting applied to the D/A converter U30 may range from 0 to 255. Alternately, the counters U24, U25 could be initialized to a desired setting by loading the binary value on the lines TP0–TP7 and strobing the EXT LOAD line.

Once the control unit 500 and the plotter 800 are initialized, the printing cycle may begin. The computer 700 issues a command to the interface unit 600 to produce the series of PRT* signal pulses. The computer 700 then commands the plotter 800 to print, for example, a line along a selected path. The plotter 800 positions the jetting head 400 and target 1 and issues the pen down signal PENDN. The signal is delayed by the print control circuit 510 to ensure that the target 1 is properly positioned. At the expiration of the delay, the signal is ANDed with the closed enable switch S1 and the series of print pulses PRT*. The result of the AND operation is the application of the PRT* pulses to the pulse generator circuit 530.

The PRT* signal is applied through the jumper JMP to the opto-isolator U18 and then to the one-shot U23. The one-shot U23 produces a pulse signal which is then converted from CMOS signal levels to the 15 volt DC signal level by the transistor Q9. The rise and fall circuitry comprising Q10, Q11, Q12 converts the square wave pulse into a pulse having the rise and fall characteristics preset by the resistors R49, R52. The conditioned pulse is then amplified by the amplifier U32 and applied to the amplifier U31.

The amplifier U31 converts the polarity of the conditioned pulse to that acceptable by the D/A converter U30 and supplies an adjustable DC offset. The DC offset is used to counteract possible distortion attributable to the amplifier U31. The distortion arises in that, for the amplifier U31 to be adequately responsive, a small degree of current must flow through the resistor R41. This current creates an offset condition at the output of the amplifier U29 which is then scaled by the D/A converter U30 in correspondence with the binary data. The resistor R63 allows a small amount of current to be applied to the amplifier U31 to control the offset voltage attributable to the current flowing through the resistor R41.

The D/A converter U30 scales the difference between the inputs REF(+), REF(−) using the binary data supplied to input lines B1–B8 to produce a current output pulse IOUT and a current inverted output pulse IOUT*. The two outputs IOUT, IOUT* are fed to the amplifier U29 which convert the current outputs into a single voltage output. The scaled, conditioned pulse is then applied to the output circuit comprising the amplifier U28 and the transistors Q3, Q4, Q5, Q6, Q7. The circuit produces a high voltage pulse with the aforementioned rise and fall characteristics to drive the piezo-electric transducer 434.

The high voltage pulse is applied to the transducer 434 and causes a droplet 2 of fluid to be propelled onto the target 1. Since the pen down signal PENDN is still applied, additional droplets 2 are produced from the jetting head 400. The plotter 800 moves the jetting head 400 and target 1 along the desired path during the emission of the droplets 2 to produce the desired printed line. When the printing is complete, the plotter 800 removes the pen down signal PENDN and the droplet emission stops. Of course it should be understood that dots, circles and the like could be produced by appropriate positioning of the target 1 and jetting head 400.

The size and uniformity of the droplets 2, as well as the presence of any satellite droplets, may be observed with the aid of the scope 950 and the LED 900. The scope 950 and the LED 900 are positioned such that the droplets 2 pass between the scope 950 and the LED 900 and within the focal range of the scope 950. The strobe pulse when applied to the LED 900 causes the LED 900 to momentarily flash. The timing of the activation and the width of the pulse may be adjusted such that the flash occurs when the fluid, expelled in response to the high voltage pulse, is between the scope 950 and the LED 900. The dispensed quantity of fluid may then be observed in flight or at or near the movement of separation from the orifice 433. Corrections based on the observation may then be made to the system 10.

Since each droplet 2 is small in volume, the droplet 2 may be rapidly absorbed by the target 1, thereby allowing rapid and precise placement of a variety of reagents on the target 1 with reduced drying time and reduced potential of fluidic mixing. In addition, the ability to place small droplets 2 in a precise manner enables the target 1 to be printed in a high density matrix with a variety of reagents as isolated matrix elements.

In some printing applications, particularly when printing fluids of low viscosity and surface tension, it may be desirable to force the fluid through the jetting tube 432 under pressure and allow the vibrations produced by the transducer 434 to break the emitted fluid stream into precise droplets 2. Under this mode of printing, the emission of droplets 2 can not be stopped by cessation of the transducer activation pulse. It is therefore necessary to prevent fluid emission by other means. One preferred means of momentarily stopping emission of the droplets is shown schematically in FIG. 4. In this arrangement, structure similar to structure represented in FIG. 3, in form and function, is represented by like reference numerals.

The arrangement, generally represented by the numeral 20, includes a closed reagent recirculation system comprising a normally closed three way valve 970, a sump 960 and a recirculation pump 980. In the continuous mode, the reagent fluid is forced out the orifice 433 by hydraulic pressure and broken into a series of substantially uniform droplets 2 by movement of the transducer 434. A regulated, filtered air supply 100 is used to pressurize the reagent fluid reservoir 200. The reagent fluid within the reservoir 200 may optionally be agitated by a magnetic stirrer unit 990. This is especially useful for reagent fluids comprising suspended particles.

The three-way valve 970 comprises a common channel, a normally open channel and a normally closed channel. The fluid is forced through the filter 300 and applied to the normally closed channel of the valve 970. When the normally closed channel is closed, the normally open channel of the valve 970 functions as a vent for the reagent jetting head 400. The common channel is connected to the reagent supply tube 430 of the jetting head 400. The reagent supply tube 430 is also connected to the sump 960.

In operation, the normally closed channel is opened by an appropriate signal supplied by the computer 700 which also closes the normally open channel. When the normally closed channel is opened, fluid is permitted to pass to the sump 960 and to the jetting head 400. The sump 960 collects the reagent fluid not transferred to the jetting head 400. The sump 960 supplies the collected fluid to the inlet side of the recirculating pump 980 which returns the fluid to the reservoir 200. The returned fluid is then mixed with the contents of the reservoir 200 and is available for recirculation.

When operating in the continuous mode, rather than interrupt the continuous stream of print pulses to the jetting head 400, the printing may be momentarily stopped by closing the normally closed channel of the valve 970. The closing of the normally closed channel stops the flow of reagent fluid to the jetting head 400 and allows the jetting head 400 to vent to atmospheric pressure. With the fluid supply blocked, the jetting head 400 is unable to expel further droplets 2. Thus, if positioning of the target 1 by the plotter 800 requires a longer time interval than the time between droplet 2 emission, the computer 700 may close the normally closed channel of the valve 970. The plotter 800 may then position the target 1 or position a new target 1 as desired.

When printing, the active ingredient of the reagent is tailored to achieve a desired concentration per unit area on the target 1. However, to a certain extent the final concentration per unit area can be adjusted by varying the density of the droplets 2 printed on the target 1. The preferred embodiment is particularly well suited to this application due to its ability to print precise, discrete gels of reagent.

Figure 6A:
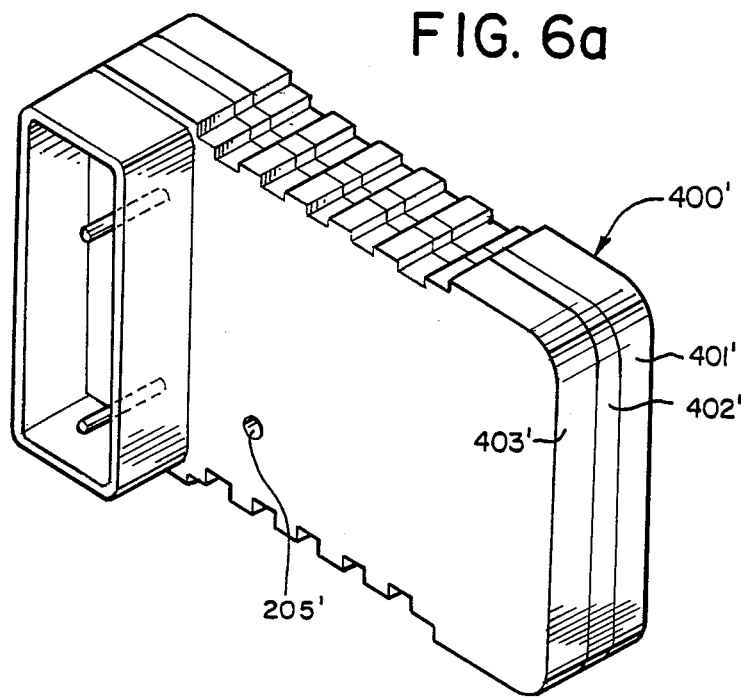
FIG. 6a is a perspective view of a second preferred embodiment of the jetting head of the present invention.
Figure 6B:
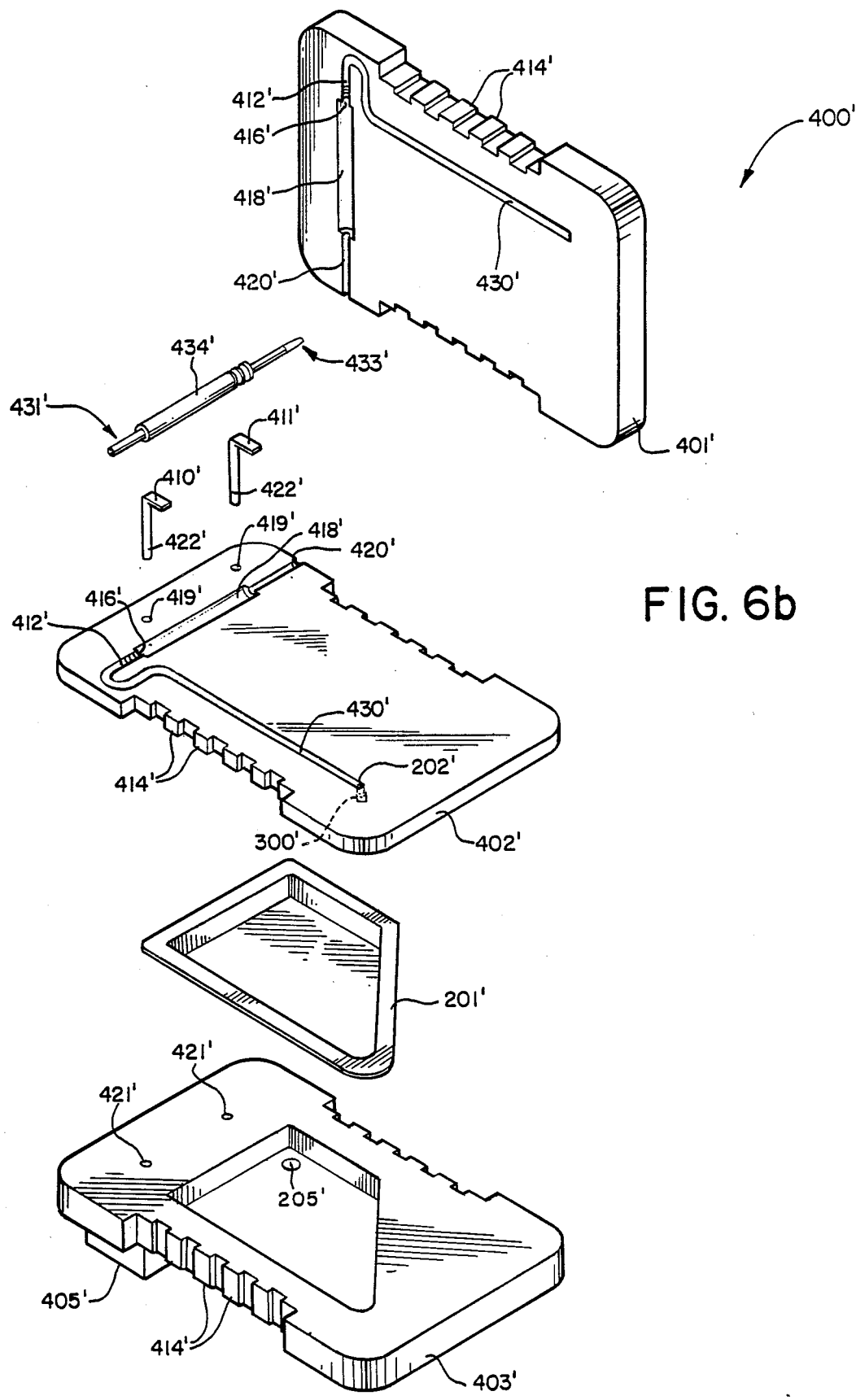

A second preferred embodiment of the jetting head is illustrated in FIGS. 6a-6b and is generally represented as 400'. The jetting head 400' comprises a housing formed into three sections 401', 402', 403'. The housing section 403' comprises a recessed region which forms the reagent fluid reservoir 200' when the housing section 403' is positioned against housing section 402'.

The jetting head 400' further comprises a piezo-electric transducer 434' and a reagent jetting tube 432' similar to those of the first embodiment. The jetting head 400' and the transducer 434' are most clearly shown in FIG. 6b. The jetting tube 432' defines an orifice 433' at one end and a reagent fluid receiving aperture 431' at the other end. The transducer 434' is mounted to the jetting tube 432' concentrically about the mid-region of the tube 432' with epoxy.

The transducer 434' and the jetting tube 432' are positioned in channels 420', 418', 416' located in the housing sections 402', 401'. The channel 416' comprises a plurality of sealing teeth 412' operative to engage and seal against the fluid receiving end 431' of the jetting tube 432'. The channel 416' is connected to the reagent fluid supply channel 430'. The supply channel 430' is connected with the fluid reservoir 200' by means of an aperture 431' through the housing section 402', shown in FIG. 6b.

The reservoir 200' comprises a flexible reservoir lining 201' adapted to contain the reagent fluid. The lining 201' comprises one aperture which is connected to the housing 402' to allow the fluid to pass from the lining 201'. A vent 205', located in the housing 403', allows the space between the reservoir 200' and the lining 201' to be vented or pressurized. A filter 300' is positioned within the aperture 202' to trap unwanted particulate foreign matter.

Electrical pulses are supplied to the transducer 434' by means of two contact pins 422'. The pins 422' are inserted through respective apertures 419' of the housing section 402' and respective apertures 421' of the housing section 403'. Two thin electrically conductive strips 410', 411', shown in FIG. 6b, are used to connect the transducer 434' with the contact pins 422'. A protective shield 405' extends from the housing section 403' to partially isolate the protruding portions of the contact pins 422'.

The function and operation of the jetting head 400' is similar to that of the jetting head 400 and therefore will not be discussed in detail. The collapsible inner lining 201' of the reservoir 200 allows the jetting tube 432' to be primed by pressurizing the reservoir 200' through the vent 205'. Once primed, the jetting head 400' may be used as described above in reference to the jetting head 400.

The jetting head 400' provides a advantage in that the entire fluidic system is contained in one housing. Such containment allows for fast and efficient replacement of the jetting heads without fluid contamination problems. This embodiment is especially advantageous for systems designed to dispense a variety of reagent fluids contained within individual, removable jetting heads.

Figure 7:
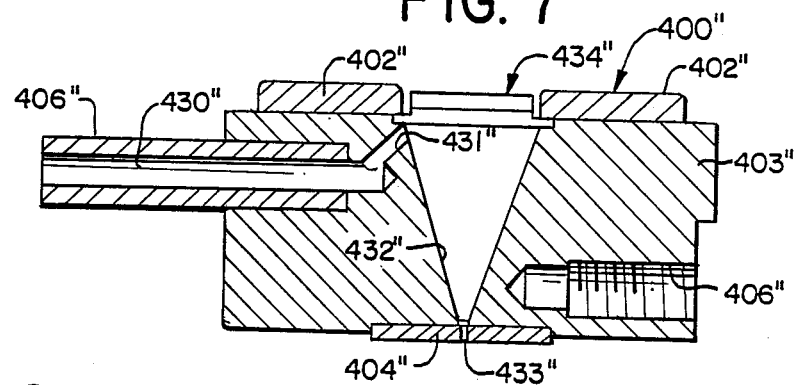
FIG. 7 is a sectional representation of a third preferred embodiment of the jetting head of the present invention.

A third preferred embodiment of the jetting head is shown in FIG. 7 and generally represented as 400". The jetting head 400" comprises a housing 403", a reagent fluid supply tube 406", a piezoelectric transducer 434" and an orifice plate 404". The housing 403" defines a conically shaped fluid chamber 432". An orifice plate 404", defining an orifice 433", is fastened to the housing 403" such that the orifice 433" is located at or near the apex of the conical fluid chamber 432".

The fluid feed tube 406" is attached to the housing 403" and defines a supply channel 430". The supply channel 430" is in fluid communication with the fluid chamber 432" by means of a connecting channel 431". The base of the fluid chamber 432" is formed by the disc-shaped transducer 434". The transducer 434" is held in position by a hold down plate 402" attached to the housing 403". The electrical connections to the transducer 434" are of conventional design and are therefore not shown. The housing 403" further comprises a threaded aperture 406" for mounting the jetting head 400".

The jetting head 400" operates in a manner similar to the jetting heads described above. However, in this jetting head the transducer 434" is normally disk shaped. When the electrical pulse is applied, the transducer 434" bends slightly, thereby altering the volume of the conically shaped jetting chamber 432". The change in volume of the chamber 432" causes the expulsion of fluid through the orifice 433" and the intake of fluid through the supply channel 430" as described in reference to the jetting head 400.

Figure 8:
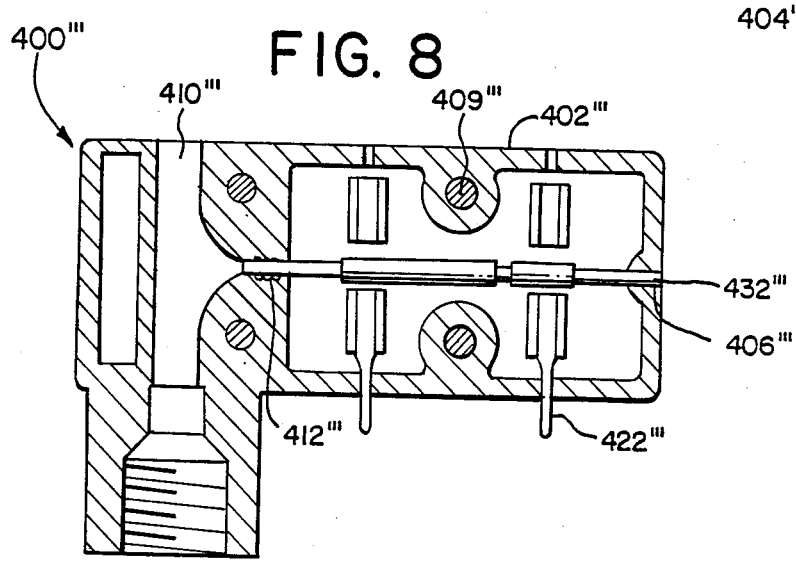
FIG. 8 is a sectional view of a symmetrical portion of a fourth preferred embodiment of the jetting head of the present invention.

A fourth preferred embodiment of the jetting head is shown in FIG. 8 and is generally represented as 400'''. The jetting head 400''' is very similar in form and function to the jetting head 400 and will not be described in detail. The jetting head 400''' comprises two symmetrical housing sections. The sections may be connected together by means of apertures 409''' and screws, not shown. When assembled, the housing sections 404''', 402''' form a T-shaped supply channel 410'''.

In operation, the jetting head 400''' functions in a manner similar to the jetting head 400. The jetting head 400''' is especially suited for use in the continuous mode, but may also be used in the drop on demand mode. In the continuous mode, the fluid is circulated continuously through the supply channel 430''' allowing the jetting tube 432''' to withdraw as much fluid as required.

By way of illustration and with no limitations intended the following information is given to further illustrate the above described embodiments. The computer 700 is an IBM Corporation Personal Computer with 640 kbytes of RAM memory. The interface unit 600 is a Burr Brown interface unit model number PC 20001. The plotter 800 is manufactured by Houston Instrument as model number DMP-40. Communication between the plotter 800 and the interface unit 600 is performed through a standard asynchronous serial communication port.

The electrical pulse applied to the jetting head 400 to activate the transducer 434 comprises a rise time of approximately 5 usecs, a fall time of approximately 5 usecs and a pulse width of approximately 35 usecs. When the transducer 434 is operated in the drop on demand mode, the voltage potential of the pulse is 60 volts plus or minus 10 volts and the pulse frequency can be up to 4 khz. When the transducer 434 is operated in the continuous mode, the voltage potential of the pulse is 30 volts plus or minus 10 volts and the pulse frequency can be up to 10 khz.

The jetting tube 432 is manufactured from a pyrex glass tube and measures 0.027 inches outside diameter and 0.020 inches inside diameter. The tube is drawn to a closed taper in an electric furnace. The tapered end is then cut and ground to a desired orifice opening of 0.002 to 0.004 inches in diameter is cut to a final length of 0.945 inches in the case of the dispenser embodiment and ultrasonically cleaned in acetone. After being cleaned and dried the large end of the tube is fire polished. If desired, the orifice end of the tube may receive a coating, such as a hydrophobic polymer, to enhance droplet separation from the tube.

The supply tube 430 is formed from 0.023 inch inside diameter and 38 inch outside diameter polyethylene tubing produced by Intramedic Corp. as model number #14 170 11B. During assembly, one end of the tubing is stretched over a warm tapered mandrel. The stretched end of the supply tube 430 is then inserted over the large fire polished end of the jetting tube 432. The assembly is then cleaned and baked in a circulating air oven at 50° C. for 10 minutes.

The transducer 434 was purchased from Vernitron of Cleveland, Ohio as model number PZT-5H. The electrodes 437, 436 are comprised of nickel and are separated from each other on the outer surface of the transducer by approximately 0.030 inches. The jetting tube 432 is inserted into the cylindrical piezoelectric tube 434 and secured with epoxy manufactured by Epoxy Technology of Bellerica, Massachusetts as model number 301. The epoxy is applied at the junction of the tube 432 and transducer 434 with a syringe. The epoxy flows along the tube 432 inside the transducer 434 by capillary action. The assembly is then baked in a circulating air oven at 65° C. for one hour to cure the epoxy.

The contact pins 422 are secured to one of the housing sections 402, 404 with a drop of epoxy. The transducer jetting tube 434, 432 is placed in the housing such that the orifice end 433 of the tube 432 protrudes approximately 0.030 inches from the housing 402, 404. A drop of silver epoxy is placed between each contact pin 422 and the transducer 434 to ensure a secure electrical connection. Epoxy is also applied to the junction of the housing 402, 404 and supply tube 430. The other section of the housing 402, 404 is then screwed into place.

The periphery of the housing 402, 404 is sealed with a capillary sealer such as cyclohexanone. Epoxy is then added around each contact pin 422 and around the orifice end 433. The assembly is then baked in a circulating air oven at 65° C. for one hour.

The filter 300 is formed from a polyester mesh with 20 um pores and positioned in a polypropylene housing. The air pressure supplied to the reservoir 200 during continuous printing operations is regulated at approximately 10 to 30 psi.

Figure 9:
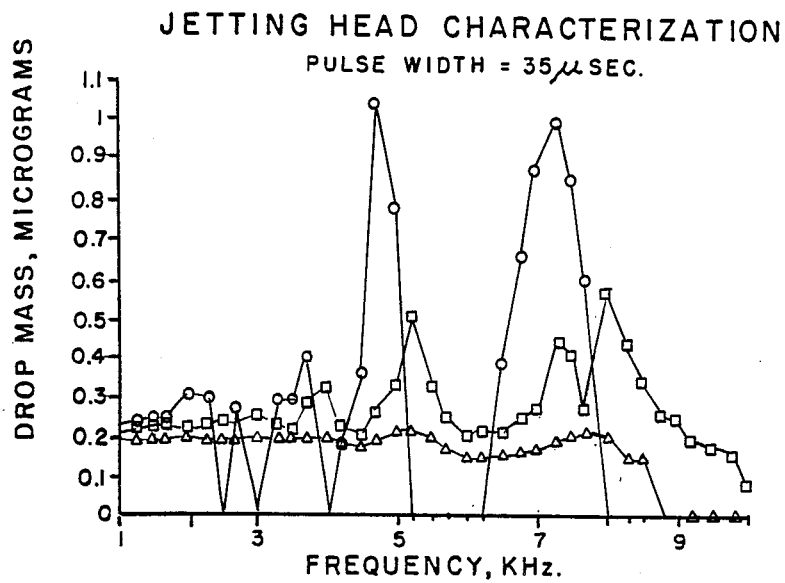
FIG. 9 is a graph of the drop mass of the emitted droplets as a function of emission frequency for several fluid viscosities.
Figure 10:
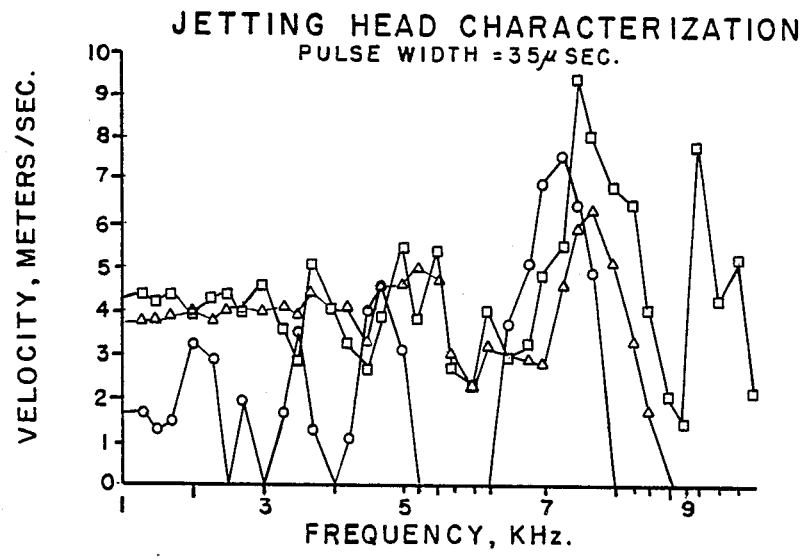
FIG. 10 is a graph of the velocity of the emitted droplets as a function of frequency for several fluid viscosities.
Figure 11:
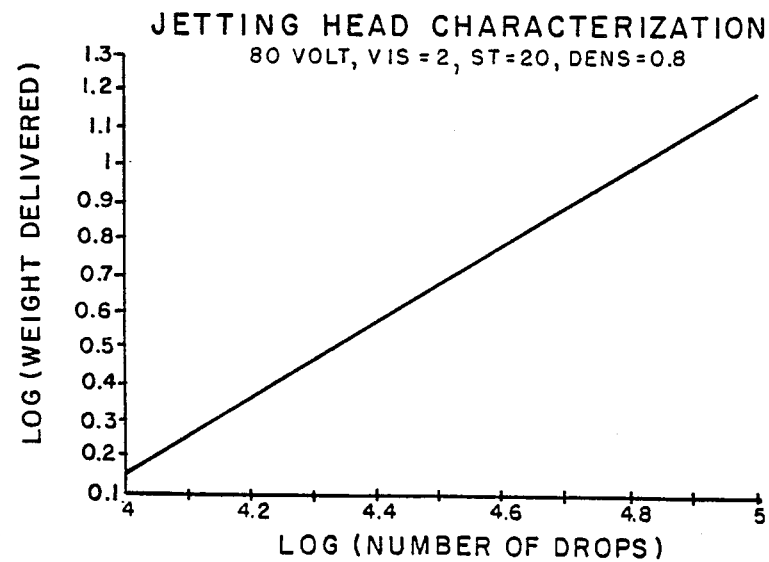
FIG. 11 is a graph of the total weight of fluid emitted as a function of the number of emitted droplets for a given fluid.

The reagents used have the following characteristics:
Printing (drop on demand mode):
 Fluid viscosity range: 1–30 centipoise
 Fluid surface tension: 20–70 dyne/cm
Printing (continuous mode):
 Fluid viscosity range: up to 50 centipoise
 Fluid surface tension: not measured
Dispensing (drop on demand mode):
 Fluid viscosity range: 2–30 centipoise
 Fluid surface tension: 20–70 dyne/cm A measure of the performance and selected operating characteristics for a typical jetting head are presented in FIGS. 9–11. FIG. 9 is a graph of the mass of a droplet as a function of droplet emission frequency for three fluids. The viscosity of the fluids were 1, 5 and 24 centipoise and the transducer excitation pulse width was 35 microseconds. As shown in FIG. 9, the higher fluid viscosity results in a more stable operating performance of the jetting head. FIG. 10 is a graph of droplet velocity as a function of droplet emission frequency for fluid viscosities of 1, 5 and 24 centipoise. The log of the total fluid weight as a function of the log of the number of droplets emitted is shown in FIG. 11. The fluid used had a viscosity of 2 centipoise, a surface tension of 20 dyne/cm, and a density of 0.8 gram/cc. The transducer excitation pulse was 80 volts and the excitation frequency was approximately 711 Hz.

Some blood typing reagents and some allergen reagents have very low viscosities and surface tensions. Although in some cases viscosity modifiers, such as glycerol, dextran, glucose, and the like, may be added to increase the viscosity, a few reagents are adversely affected by such modifiers.

Developing stable and reproduceable demand mode jetting is difficult with very low viscosities. Although droplet emission can be established at some fundamental frequencies, the droplets dispensed may have small satellite droplets which reduce the accuracy for metering and dispensing applications. However, even with the satellite drops, sufficient reagent is adequately delivered for most print applications without a substantial decrease in print quality.

Glycerin may be used as a viscosity modifier to improve jetting reliability and to prevent obstruction of the orifice arising from evaporation of the reagent fluid components. Glycerin has been found especially beneficial for those reagents containing particulate material. The evaporation of the fluid component results in a concentration of glycerin located at the orifice. The plug of glycerin substantially prevents further evaporation of the reagent fluid. During the next activation cycle of the transducer, the plug of glycerin is expelled from the orifice.

When operating in the dispensing mode the volume of the droplets can be varied to substantially uniformly contain from 100 pico-liters to 1 micro-liter. The droplets can be produced at a rate of approximately 1 khz to 8 khz. When operating in the printing mode the size of the pel made by each droplet measures approximately 0.001–0.012 inches in diameter.

A copy of the program used in the computer 700 for a printing operation is attached hereto as Appendix A. The values, manufacturer and manufacturing part number of the circuit components of the jetting control unit 500 are substantially as follows:

| Ref. Numeral of Component | Description and Value | Manufacturer and Part No. |
|---|---|---|
| R39,45–48,57, | | |

-continued

| Ref. Numeral of Component | Description and Value | Manufacturer and Part No. |
|---|---|---|
| 58 | RES. 10KOHM¼WATT5%C.F. | |
| R66 | RES.150OHM¼WATT5%C.F. | |
| R3 | RES.15KOHM¼WATT5%C.F. | |
| R34 | RES.16KOHM¼WATT5%C.F. | |
| R50 | RES.2.4KOHM¼WATT1%M.F. | DALE RLO79242G |
| R13,23,36,40,41 | RES.2.4KOHM¼WATT5%C.F. | |
| R56 | RES.20KOHM¼WATT5%C.F. | |
| R8 | RES.220OHM¼WATT5%C.F. | |
| R6 | RES.27OHM1WATT5%C.C. | |
| R7,12,25 | RES.2KOHM¼WATT5%C.F. | |
| R67 | RES3.6KOHM¼WATT5%C.F. | |
| R51,53 | RES.3.9KOHM¼WATT5%C.F. | |
| R29 | RES.300KOHM¼WATT5%C.F. | |
| R61 | RES.30KOHM¼WATT1%M.F. | DALE RL079303G |
| R15-18,26-28,54,55,64 | RES.4.7KOHM¼WATT5%C.F. | |
| R62 | RES.45.3KOHM¼WATT1%M.F. | DALE RN55D4532F |
| R30,33 | RES.47OHM¼WATT5%C.F. | |
| R21 | RES.470OHM¼WATT5%C.F | |
| R19 | RES.47KOHM¼WATT5%C.F. | |
| R35 | RES.510OHM¼WATT5%C.F. | |
| R43 | RES.6.2KOHM¼WATT5%C.F. | |
| R60 | RES.7.5KOHM¼WATT5%C.F. | |
| R37 | RES.75KOHM¼WATT5%C.F. | |
| R9 | RES.76KOHM¼WATT1%M.F. | DALE RN60D7682F |
| R11 | RES.820OHM¼WATT5%C.F. | |
| U2,11,14,16,22 | RES.DIP NETWRK.47KOHM | CT9 761-1R47K |
| C21,41,45 | CAP.AXIAL1MF@250VDC | MALLORY #TC56 |
| C24 | CAP.AXIAL220MF@250VDC | MALLORY LP2219250C7P3 |
| C10 | CAP.AXIAL ALUM ELEC. 4700 0MF@25VDC | MALLORY TCG472UO25NIC |
| C1,2,3,55,60 | CAP.RADIAL DIPPED TANT. 10MF@25VDC | KEMET T35OE106M025AS |
| C53 | CAP.RADIAL DIPPED TANT. 1MF@35VDC | KEMET T35OA105K035AS |
| C36 | CAP.RADIAL DIPPED TANT. 47MF@10VDC | KEMET T350H566M010AS |
| C54 | CAP.RADIAL SILV MICA 100PF300VDC | KAHGAN SD5101J301 |
| C57 | CAP.RADIAL SILV MICA 20PF300VDC | KAHGAN SP12200J301 |
| C49 | CAP. RADIAL SILV. MICA 39PF300VDC | KAHGAN SP12390J301 |
| C39 | CAP.RADIAL X7R MLC .015MF@50VDC | KEMET C315C102K1R5CA |
| C6 | CAP.RADIAL X7R MLC .022MF@50VDC | KEMET C315C223K5R5CA |
| C30,35,37 | CAP.RADIAL Z5U MLC .015MF@50VDC | KEMET C315C153K5R5CA |
| C4,7 | CAP.RADIAL 25U MLC .01MF@50VDC | KEMET C315C103K5R5CA |
| C4,5,6,9,11-19,22,23,25-28 C31-34,37,42,43 47,48,50-52 C56,58,59 | CAP.RADIAL 25U MLC .22MF@50VDC | KEMET C322C224M5U5CA |
| C46 | CAP.VARI.2-12PF. | JOHANSEN #9626 |
| CR7,8,9,10,11,12,17 | DIODE SIL. | ITT.FAIRCHLD.1N4148 |
| CR1,2,3,4 | DIODE SIL.FAST | GENL.INST.EGP10D |
| CR5 | DIODE SIL.FASTHIVOLT | GENL.INST.UF4007 |
| CR6,13,15 | DIODE SIL.REF.2,500VDC | NATL.SEMI-LM3852-2.5 |
| CR14,16 | DIODE SIL.ZENER3.8V.25WATT | MOTOROLA 1N4622A |
| U6,13,15,17 | SWITCH 8 POSITION DIP | CTS 206-8 |
| Q2,9,12 | TRANSTOR.COMMON NPN | MOTOROLA 2N2222A |
| Q8,10,11 | TRANSTOR.COMMON PNP | MOTOROLA 2N2907A |
| Q4 | TRANSTOR.HIVOLTHIFREQ.NPN | MOTOROLA MPSU10 |
| Q7 | TRANSTOR.HIVOLTHIFREQ.PNP | MOTOROLA MPSU60 |
| Q1 | TRANSTOR.HIVOLTHIINPN | TI,MOTOROLATIP48 |
| Q3,14 | TRANSTOR.HIVOLTNPN2N3439 | MOTOROLA 2N3439 |
| Q13 | TRANSTOR.HIVOLTPNP | MOTOROLA MJE5731 |
| U5,27 | IC 1-SHOT 74HC221 | NATL.SEMI MM74HC221N |
| U23,26 | IC 1-SHOT 74LS221 | NATL.SEMI DM74LS221N |
| U7-10 | IC COMPARATOR 74HC688 | NATL.SEMI MM74HC688N |
| U30 | IC CONVERTER DAC0800 | NATL.SEMI DAC0800LCN |
| U24,25 | IC COUNTER 74HC193 | NATL.SEMI MM74HC193N |
| U28 | IC HI SLEW HI VOLT OP AMP | BURR-BROWN 3584JM |
| U1 | IC HYBRID DC/DC CONVERTER | BURR-BROWN MODEL 724 |

-continued

| Ref. Numeral of Component | Description and Value | Manufacturer and Part No. |
|---|---|---|
| U4 | IC OC DRIVER SN7406 | NATL.SEMI DM7406N |
| U3 | IC OCTAL LATCH 74HC374 | NATL. MM74HC374N |
| U12,29,31,32 | IC OP AMP LF256 | NATL.SEMI LF256H |
| U18,19,20,21 | IC OPTO ISOLATOR | HEWLTT-PCKRD HCPL2300 |
| R24,42,63 | POT100KOHM¼WATT10% | BOURNS 3622-1-104 |
| R38,49,52 | POT10KOHM¼WATT10% | BOURNS 3622W-1-103 |
| R20 | POT25KOHM¼WATT10% | BOURNS 3622W-1-253 |
| R14,31 | POT2KOHM¼WATT10% | BOURNS 3622W-1-202 |
| VRI | REGULATOR 5VDC | NATL.LM340T-5.0 |
| R10 | RES.1MEGOHM¼WATT5%C.F. | |
| R2,4 | RES.1.2KOHM¼WATT5%C.F. | |
| R32 | RES.1.6KOHM¼WATT5%C.F. | |
| R44 | RES.1.8KOHM¼WATT5%C.F. | |
| R1 | RES.10MEGOHM¼WATT5%C.F. | |
| R5,R22 | RES.10OHM¼WATT5%C.F. | |
| R65 | RES.100KOHM¼WATT5%C.F. | |
| R59 | RES.10KOHM¼WATT1%M.F. | DALE RN55D1002F |
| R100 | RES.270OHM | |
| R101,108 | RES.470OHM | |
| R102,103 106,109,110 | RES.1KOHM | |
| R104 | RES.4700OHM | |
| R105 | POT.100KOHM | |
| R107 | POT.10KOHM | |
| R111,113 | RES.220OHM | |
| R112 | RES.22OHM | |
| R114,115 | RES. 47OHM | |
| C100 | CAP.10MF035 VPC | |
| C108 | CA.10000 PF | |
| D100 | DIODE | 1N4148 |
| Q100,105 | TRANSTOR | 2N2222 |
| Q101,102 | TRANSTOR | 2N3906 |
| Q103,104 | TRANSTOR | 2N3904 |
| U100,U108 | IC I-SHOT | 74LS123 |
| U103,104 105,106 | IC INVERTOR | 74LS04 |
| U108 | IC LINE DECODER | 74LS138 |

Of course, it should be understood that a wide range of changes and modifications can be made to the preferred embodiments described above. For example, the transducer could be of a type other than piezo-electric such as magnetic-strictive, electrostrictive, and electro-mechanical. Also, although in some of the foregoing embodiments a droplet may be directed to a location on a medium by positioning the jetting tube and/or the medium, the droplet could also be directed to a location on the medium by deflecting the droplet using known droplet deflecting techniques. It is therefore intended that the foregoing detailed description be regarded as illustrative rather than limiting, and that it be understood that it is the following claims, including all equivalents, which are intended to define the scope of this invention.

APPENDIX A

Reagent Jet Printer
Reagent Calibration

Offset  Data  Source Line                                                                 IBM Personal Computer BASIC Compiler V2.00

```
0030  0006   REM $TITLE:'Reagent Jet Printer' $SUBTITLE:'Reagent Calibration' $LINESIZE: 132
0030  0006   'MODULE    - "REACAL"
0030  0006   '
0030  0006   'AUTHOR    - N. A. Enevold
0030  0006   '
0030  0006   'COPYRIGHT (C) 1985 ABBOTT LABORATORIES
0030  0006   'REVISION - 2.0 07-01-86 NAE MicroFab modifications
0030  0006   '         - 1.0 02-11-86 NAE Creation of initial code
0030  0006   '
0030  0006   'SYSTEM    - This code can only be compiled by the BASCOM
0030  0006   '           COMPILER, it will not run under the INTERPRETER!!
0030  0006   '
0030  0006   'DESCRIPTION:
0030  0006   '       The reagent calibrate module presents a menu with 12 items arranged
0030  0006   '       in 3 columns of 4 rows. The arrow keys allow movement around the
0030  0006   '       table, the + and - keys increment or decrement values in the first
0030  0006   '       column, and the enter key executes commands in the third column.
```

```
0030  0006   '         The second column is an array of ASCII strings representing reagent name,
0030  0006   '         concentration, density, and viscosity.  The values entered in column one
0030  0006   '         are drop frequency, pulse width, strobe delay, and nozzle number.
0030  0006   '         The commands in the third column are start/stop, load, save, and exit.
0030  0006   '
0030  0006   'DATA DICTIONARY
0030  0006   '         MENU%             Pointer to which menu item is active (0-11)
0030  0006   '         MENU$(17,1)       Array for strings used to display the menu
0030  0006   '         MENU(17,4)        Array for numbers in the menu display
0030  0006   '         DIFF%             Differential to move MENU% at arrow key input
0030  0006   '         TYPE%             Pointer set during main scan to direct action
0030  0006   '         KEYBUF$           Storage for string input from menu display
0030  0006   '         A$                Destination for single keystroke inputs
0030  0006   '         FILE$             String where filename is built for reagent data file
0030  0006   '         REANAME$          String where reagent name is stored
0030  0006   '  -      R%                Row to display special graphics character in menu
0030  0006   '         C%                Column to display special graphics character in menu
0030  0006   '         N%                Special graphics character is read into here
0030  0006   '         OLD.AMP.VALUE%    Integer value for setting pulse amplitude
0030  0006   '         DIG.VAL%          Value set to digital port 0 to inc/dec amplitude
0030  0006   '
0030  0006   SUB REAGENT.CALIBRATE STATIC
0047  0006
0047  0006        DIM MENU$(17,1),MENU(17,4)
004B  01FE
004B  01FE        GOSUB INITIALIZE:          'read init. values and set screen
004E  01FE
004E  01FE        WHILE TYPE% <> 1
0059  0200
0059  0200          TYPE% = 0
0060  0200          A$ = ""
006A  0204
006A  0204          WHILE A$ = ""
0079  0204            A$ = INKEY$
0083  0204            IF ACTIVE% = 1 AND DOWNTIME < TIMER THEN GOSUB PEN.DOWN
00AD  020A          WEND
00B0  020A
00B0  020A          IF A$ = CHR$(13) THEN TYPE% = 1:              'execute <cr>
00CA  020A          IF A$ = "+" THEN TYPE% = 2:                   'increment variable
00E0  020A          IF A$ = "-" THEN TYPE% = 3:                   'decrement variable
00F6  020A          IF A$ = CHR$(0) + CHR$(72) THEN TYPE% = 4:    'up arrow key
011B  020A          IF A$ = CHR$(0) + CHR$(80) THEN TYPE% = 5:    'down arrow key
0140  020A          IF A$ = CHR$(0) + CHR$(75) THEN TYPE% = 6:    'left arrow key
0165  020A          IF A$ = CHR$(0) + CHR$(77) THEN TYPE% = 7:    'right arrow key
018A  020A          IF A$ > CHR$(47) AND A$ < CHR$(123) THEN TYPE% = 8:' ascii 0 - z
01C2  020A
01C2  020A          ON TYPE% GOSUB T1, T2, T3, T4, T5, T6, T7, T8
01DB  020A
01DB  020A        WEND
01DF  020A        TYPE% = 0
01E6  020A
01E6  020A        EXIT SUB
01EA  020A   REM $PAGE
01EA  020A   '*********** SUBROUTINES FOR THIS MODULE ***********
01EA  020A
01EA  020A   T1:          '<cr> execute command
01EF  020A        IF MENU% < 12 THEN TYPE% = 0:RETURN:   'exit to print menu, no action
0205  020C        ON MENU% - 11 GOSUB T1A, T1B, T1C, T1D
021A  020C        IF MENU% < 15 THEN TYPE% = 0
022C  020C        RETURN
0230  020C
0230  020C   T1A:         'start/stop drop flow
0235  020C        IF MENU$(12,0) = "START" THEN GOSUB START.INK
025A  020C        IF MENU$(12,0) = "STOP " THEN GOSUB STOP.INK
027F  020C        MENU$(12,0) = TEMP$
029A  0210        COLOR 0,7:GOSUB DISPMENU
02AC  0210        RETURN
02B0  0210
02B0  0210   START.INK:
```

```
02B5    0210            TEMP$ = "STOP "
02BF    0210            CALL DOT.ON:            'in module PCI
02CB    0210            LOCATE 17,71:COLOR 27,0:PRINT "PRINTING";
02F1    0210            ACTIVE% = 1
02FB    0210            RETURN
02FC    0210
02FC    0210    STOP.INK:
0301    0210            TEMP$ = "START"
030B    0210            CALL DOT.OFF:           'in module PCI
0317    0210            LOCATE 17,71:COLOR 15,0:PRINT "        ";
033D    0210            ACTIVE% = 0
0344    0210            RETURN
0348    0210
0348    0210    T1B:            'load reagent profile
034D    0210            IF MENU$(6,1) = "" THEN LOCATE 25,1:PRINT "Reagent Name is not specified";:GOSUB ANYKEY:RETURN
0391    0210
0391    0210            GOSUB SEARCH
0397    0210
0397    0210            IF I% < (REANUM% + 1) THEN GOTO FOUND
03AB    0214            LOCATE 25,10-LEN(MENU$(6,1))/2:PRINT MENU$(6,1);" not Found";
0404    0214            GOSUB ANYKEY:   'wait for a keyhit
040A    0214            RETURN
040E    0214
040E    0214    FOUND:
0413    0214            FILE$ = RIGHT$(STR$(I%),LEN(STR$(I%))-1) + "REA.RJP"
0437    0218            OPEN FILE$ FOR INPUT AS #1:     'set pattern data file for read
0448    0218            INPUT #1,MENU(0,0):     'read frequency
046B    0218            INPUT #1,MENU(1,0):     'read amplitude
048B    0218            INPUT #1,MENU(2,0):     'read strobe delay
04AE    0218            INPUT #1,MENU(3,0):     'read pulse width
04D1    0218            INPUT #1,MENU(4,0):     'read rise time
04F4    0218            INPUT #1,MENU(5,0):     'read fall time
0519    0218
0519    0218            INPUT #1,MENU$(7,1):    'read concentration
053D    0218            INPUT #1,MENU$(8,1):    'read density
0561    0218            INPUT #1,MENU$(9,1):    'read viscosity
0585    0218            INPUT #1,MENU$(10,1):   'read surface tension
05A9    0218
05A9    0218            CLOSE #1:       'done with data file
05B0    0218
05B0    0218            OPEN "READEF.RJP" FOR OUTPUT AS #1
05C2    0218            PRINT #1,FILE$:                 'save filename in default file
05D2    0218            PRINT #1,MENU$(6,1):    'save the directory name as well
05F4    0218            CLOSE #1
05FB    0218            GOSUB DISP.PARMS:       'show all parameters
0601    0218            RETURN
0605    0218
0605    0218    T1C:            'save reagent profile
060A    0218            IF MENU$(6,1) = "" THEN LOCATE 25,1:PRINT "Reagent Name is not specified";:GOSUB ANYKEY:RETURN
064E    0218            OPEN "READIR.RJP" FOR INPUT AS #1
065F    0218            INPUT #1,REANUM%
0671    0218            CLOSE #1
0678    0218            IF REANUM% < 80 THEN GOTO SAVE.REA
0687    0218            LOCATE 25,1:PRINT "Directory is Full (80 reagents max.)"
06A1    0218            GOSUB ANYKEY:RETURN
06AB    0218    SAVE.REA:
06B0    0218            GOSUB SEARCH
06B6    0218            IF I% > REANUM% THEN GOTO SAVEREA1
06C7    0218            REANUM% = I%
06CE    0218            COLOR 15,0
06DA    0218            LOCATE 25,1:PRINT MENU$(6,1);" already exists. Replace it with new values? ";
070C    0218            A$ = ""
0716    0218            WHILE A$ = ""
0725    0218                    A$ = INKEY$
072F    0218            WEND
0732    0218            LOCATE 25,1:PRINT SPACE$(79);
074F    0218            IF A$ = "Y" OR A$ = "y" THEN GOTO REPLACE
0778    0218            RETURN
077C    0218
```

```
077C   0218   SAVEREA1:
0781   0218        KILL "READIR.OLD":         'delete old backup directory
0786   0218        NAME "READIR.RJP" AS "READIR.OLD":    'save old directory
0792   0218        OPEN "READIR.OLD" FOR INPUT AS #1
07A3   0218        OPEN "READIR.RJP" FOR OUTPUT AS #2:   'set up new dir
07B5   0218
07B5   0218        INPUT #1,REANUM%:     'read number of dir entries
07C7   0218        REANUM% = REANUM% + 1: 'increase by 1
07D0   0218        WRITE #2,REANUM%:     'save in new directory
07E1   0218
07E1   0218        FOR I=1 TO REANUM% - 1
07FA   021C           LINE INPUT #1,A$:  'read entry from old dir
0807   021C           PRINT #2,A$:       'write entry in new directory
0817   021C        NEXT I
0832   0220
0832   0220        CLOSE #1
0839   0220
0839   0220        PRINT #2,MENU$(6,1):  'write new entry to new directory
085B   0220        CLOSE #2:      'done with directory
0862   0220
0862   0220   REPLACE:
0867   0220        FILE$ = RIGHT$(STR$(REANUM%),LEN(STR$(REANUM%))-1) + "REA.RJP"
088B   0220
088B   0220        OPEN FILE$ FOR OUTPUT AS #1:    'create new pattern data file
089D   0220        WRITE #1,MENU(0,0):   'store frequency
08BB   0220        WRITE #1,MENU(1,0):   'store amplitude
08DC   0220        WRITE #1,MENU(2,0):   'store strobe delay
08FD   0220        WRITE #1,MENU(3,0):   'store pulse width
091E   0220        WRITE #1,MENU(4,0):   'store rise time
093F   0220        WRITE #1,MENU(5,0):   'store fall time
0962   0220
0962   0220        WRITE #1,MENU$(7,1):  'store concentration
0984   0220        WRITE #1,MENU$(8,1):  'store density
09A6   0220        WRITE #1,MENU$(9,1):  'store viscosity
09C8   0220        WRITE #1,MENU$(10,1): 'store surface tension
09EA   0220
09EA   0220        CLOSE #1:      'done with data file
09F1   0220
09F1   0220        OPEN "READEF.RJP" FOR OUTPUT AS #1
0A03   0220        PRINT #1,FILE$:               'save filename in default file
0A13   0220        PRINT #1,MENU$(6,1):  'save the directory name as well
0A35   0220        CLOSE #1
0A3C   0220        RETURN
0A40   0220
0A40   0220   SEARCH:
0A45   0220        OPEN "READIR.RJP" FOR INPUT AS #1
0A56   0220        INPUT #1,REANUM%:     'read number of patterns in dir
0A68   0220        I% = 1:               'set entry pointer
0A6F   0220
0A6F   0220   SLOOP:
0A74   0220        LINE INPUT #1,A$:     'read next pattern name from dir
0A81   0220        IF A$ = MENU$(6,1) THEN GOTO SEARCH.DONE:   'compare name with dir entry
0AA5   0220        I% = I% + 1
0AAE   0220        IF I% < (REANUM% + 1) THEN GOTO SLOOP:'check for done
0AC1   0220   SEARCH.DONE:
0AC6   0220        CLOSE #1
0ACD   0220        RETURN
0AD1   0220
0AD1   0220   T1D:          'return with no change to exit reagent calibrate
0AD6   0220        PRINT #3,"UH";
0AE6   0220        CLOSE #3:'     close com channel
0AED   0220        RETURN
0AF1   0220
0AF1   0220   T2:            'process "+" key
0AF6   0220        IF MENU% > 5 THEN RETURN
0B05   0220        NEWTIME = TIMER
0B0F   0224        DELTATIME = NEWTIME - OLDTIME
0B1F   022C        OLDTIME = NEWTIME
0B29   022C        IF DELTATIME > 0.15 THEN MULT% = 1 ELSE MULT% = MULT% + 1
```

```
0B4B  022E           IF MULT% > 100 THEN MULT% = 100
0B5D  022E           MENU(MENU%,0) = MENU(MENU%,0) + MENU(MENU%,3) * MULT%:   'add increment
0B9F  022E           IF MENU(MENU%,0) > MENU(MENU%,1) THEN MENU(MENU%,0) = MENU(MENU%,1):   'check max value
0C06  022E           COLOR 15,1:GOSUB DISPMENU:RETURN:                    'show new value
0C1D  022E
0C1D  022E    T3:           'process "-" key
0C22  022E           IF MENU% > 5 THEN RETURN
0C31  022E           NEWTIME = TIMER
0C3B  022E           DELTATIME = NEWTIME - OLDTIME
0C4B  022E           OLDTIME = NEWTIME
0C55  022E           IF DELTATIME > 0.15 THEN MULT% = 1 ELSE MULT% = MULT% + 1
0C77  022E           IF MULT% > 100 THEN MULT% = 100
0C89  022E           MENU(MENU%,0) = MENU(MENU%,0) - MENU(MENU%,3) * MULT%:   'sub increment
0CCB  022E           IF MENU(MENU%,0) < MENU(MENU%,2) THEN MENU(MENU%,0) = MENU(MENU%,2):   'check min value
0D32  022E           COLOR 15,1:GOSUB DISPMENU:RETURN:                    'show new value
0D49  022E
0D49  022E    T4:           'process up arrow key
0D4E  022E           IF MENU% MOD 6 = 0 THEN RETURN:              'in top row already
0D63  022E           DIFF% = -1:GOSUB NEWMENU:RETURN:             'move pointer up one
0D74  0230
0D74  0230    T5:           'process down arrow key
0D79  0230           IF MENU% MOD 6 = 5 THEN RETURN:              'in bottom row already
0D8F  0230           DIFF% = 1:GOSUB NEWMENU:RETURN:              'move pointer down one
0DA0  0230
0DA0  0230    T6:           'process left arrow key
0DA5  0230           IF INT(MENU% / 6) = 0 THEN RETURN            'in left column already
0DC5  0230           DIFF% = -6:GOSUB NEWMENU:RETURN:             'move pointer one left
0DD6  0230
0DD6  0230    T7:           'process right arrow key
0DDB  0230           IF INT(MENU% / 6) = 2 THEN RETURN            'in right column already
0DFE  0230           DIFF% = 6:GOSUB NEWMENU:RETURN:              'move pointer one right
0E0F  0230
0E0F  0230    T8:           'input keys into KEYBUF$ until <cr> is entered
0E14  0230           IF MENU% > 10 THEN RETURN
0E23  0230           LOCATE 25,30:COLOR 31,0:PRINT "ENTER NEW VALUE";:COLOR 15,0
0E55  0230           KEYBUF$ = A$
0E5F  0234           WHILE A$ <> CHR$(13)
0E72  0234                   LOCATE 25,47:PRINT SPACE$(15);
0E8F  0234                   LOCATE 25,47:PRINT KEYBUF$;
0EA9  0234                   A$ = ""
0EB3  0234                   WHILE A$ = ""
0EC2  0234                           A$ = INKEY$
0ECC  0234                           IF ACTIVE% = 1 AND DOWNTIME < TIMER THEN GOSUB PEN.DOWN
0EF6  0234                   WEND
0EF9  0234                   IF A$ = CHR$(8) AND LEN(KEYBUF$) > 0 THEN KEYBUF$ = LEFT$(KEYBUF$,LEN(KEYBUF$)-1)
0F3B  0234                   IF A$ > CHR$(31) AND LEN(KEYBUF$) < 15 THEN KEYBUF$ = KEYBUF$ + A$
0F75  0234           WEND
0F79  0234
0F79  0234           IF MENU% > 5 THEN GOTO STORESTRING
0F88  0234
0F88  0234           TEMP = VAL(KEYBUF$)      'temp has value of keys input
0F98  0238
0F98  0238           'round off temp according to step size in menu array
0F98  0238           TEMP = INT(TEMP / (MENU(MENU%,3)) + .5) * MENU(MENU%,3)
0FD1  0238
0FD1  0238           'test TEMP for maximum and minimum values in menu array
0FD1  0238           IF TEMP > MENU(MENU%,1) THEN TEMP = MENU(MENU%,1)
1010  0238           IF TEMP < MENU(MENU%,2) THEN TEMP = MENU(MENU%,2)
104F  0238
104F  0238           'insert new value into menu array and update screen
104F  0238           MENU(MENU%,0) = TEMP
106B  0238           LOCATE 25,30:PRINT SPACE$(40);
1088  0238           COLOR 0,7:GOSUB DISPMENU
109A  0238           RETURN
109E  0238
109E  0238    STORESTRING:
10A3  0238           MENU$(MENU%,1) = KEYBUF$
10BF  0238           LOCATE 25,30:PRINT SPACE$(40);
10DC  0238           COLOR 0,7:GOSUB DISPMENU
```

```
10EE   0238           RETURN
10F2   0238
10F2   0238   PEN.DOWN:
10F7   0238           DOWNTIME = TIMER + 1
1107   0238           PRINT #3,"D";
1117   0238           RETURN
111B   0238
111B   0238   ANYKEY:
1120   0238           LOCATE 25,64:PRINT "Strike any key..";
113A   0238           A$ = ""
1144   0238           WHILE A$ = ""
1153   0238                   A$ = INKEY$
115D   0238           WEND
1160   0238           LOCATE 25,1:COLOR 15,0:PRINT SPACE$(79);:COLOR 15,1
1196   0238           RETURN
119A   0238
119A   0238   NEWMENU: 'write old item in yellow, point to and highlight new item
119F   0238           COLOR 14,0:GOSUB DISPMENU
11B1   0238           MENU% = MENU% + DIFF%
11BD   0238           IF MENU% = 11 THEN MENU% = 10
11CF   0238           IF MENU% > 15 THEN MENU% = 15
11E1   0238           COLOR 0,7:GOSUB DISPMENU:RETURN
11F7   0238
11F7   0238   INITIALIZE:
11FC   0238           'change to second screen and display messages
11FC   0238           SCREEN 0,0,1,1:COLOR 7,0:CLS:LOCATE 10,28:PRINT "Initializing Menu Display";
1240   0238           LOCATE 12,33:PRINT "Please Wait..."
125A   0238
125A   0238           'initialize variables
125A   0238
125A   0238           ACTIVE% = 0:'   not printing
1261   0238
1261   0238           'initialize plotter com channel
1261   0238
1261   0238           OPEN "COM1:2400,N,8,2" AS #3
1273   0238           PRINT #3,";:UEC5,EFV1,H";
1283   0238
1283   0238           'initialize digital port
1283   0238           SCR% = 4
128A   023A           CALL DIGITAL.OUT(SCR%)
129A   023A           SCR% = 0
12A1   023A           CALL DIGITAL.OUT(SCR%):             'pulse reset line to set amplitude to 0V.
12B1   023A           SCR% = 4
12B8   023A           CALL DIGITAL.OUT(SCR%)
12C8   023A
12C8   023A           'set hardware pulse width
12C8   023A           CALL SET.DOT.WIDTH(5)    'in module PCI
12DE   023C
12DE   023C           'initialize menu arrays
12DE   023C           RESTORE ARRDATA
12E5   023C           FOR I%=0 TO 17
12EB   023C                   READ MENU$(I%,0),MENU$(I%,1):
131B   023C                   READ MENU(I%,1),MENU(I%,2),MENU(I%,3),MENU(I%,4)
137C   023C           NEXT I%
138F   023C
138F   023C           'set default reagent values
138F   023C
138F   023C           MENU(0,0) = 2000:           'frequency
13AB   023C           MENU(1,0) = 0:              'amplitude
13C4   023C           MENU(2,0) = 1:              'strobe delay
13E0   023C           MENU(3,0) = 090:            'pulse width
13FC   023C           MENU(4,0) = 470:            'rise time
1418   023C           MENU(5,0) = 070:            'fall time
1436   023C
1436   023C           MENU(6,0) = 0:              'name
1452   023C           MENU(7,0) = 0:              'concentration
146E   023C           MENU(8,0) = 0:              'density
148A   023C           MENU(9,0) = 0:              'viscosity
14A6   023C           MENU(10,0) = 0:                     'surface tension
```

```
14C2   023C
14C2   023C          OLD.AMP.VALUE% = 0              'initial value of 0 volts
14C9   023E
14C9   023E          'change active displayed screen to first screen to draw and display parameters
14C9   023E
14C9   023E          SCREEN 0,0,0,1:CLS
14E6   023E
14E6   023E          COLOR 13:LOCATE 1,32:PRINT "REAGENT CALIBRATE";
1507   023E          COLOR 9
150E   023E          FOR I=2 TO 79
1518   023E              LOCATE 3,I:PRINT "D";:LOCATE 5,I:PRINT "M";:LOCATE 19,I:PRINT "D";
156F   023E          NEXT I
158A   023E          FOR I=4 TO 18
1594   023E              LOCATE I,1:PRINT "3";:LOCATE I,28:PRINT ";";:LOCATE I,69:PRINT ";";:LOCATE I,80:PRINT "3";
1608   023E          NEXT I
1626   023E          RESTORE TABLE
162D   023E          FOR I=1 TO 12
1637   023E              READ R%,C%,N%:LOCATE R%,C%:PRINT CHR$(N%);
166A   0244          NEXT I
1685   0244
1685   0244          'print three headings and instructions
1685   0244          COLOR 10,0
1691   0244          LOCATE 4,7:PRINT "DROP PARAMETERS";
16AB   0244          LOCATE 4,39:PRINT "REAGENT PARAMETERS"
16C5   0244          LOCATE 4,71:PRINT "COMMANDS";
16DF   0244
16DF   0244          COLOR 7:LOCATE 21,20:PRINT "Use ";:COLOR 15:PRINT CHR$(27);CHR$(32);CHR$(26);
1729   0244          PRINT CHR$(32);CHR$(24);CHR$(32);CHR$(25);:COLOR 7:PRINT " to position highlighted cursor";
176B   0244          LOCATE 22,18:PRINT "Use ";:COLOR 15:PRINT "+";:COLOR 7:PRINT " or ";:COLOR 15:PRINT "-";
17BE   0244          COLOR 7:PRINT" to scroll current value up or down";
17D2   0244          LOCATE 23,26:PRINT "Use ";:COLOR 15:PRINT "DY";:COLOR 7:PRINT" to activate selection";
1814   0244
1814   0244   DISP.PARMS:
1819   0244          'display 18 menu choices in yellow
1819   0244
1819   0244          COLOR 14,0
1825   0244          FOR MENU% = 0 TO 17
182B   0244              GOSUB DISPMENU
1831   0244          NEXT MENU%
1841   0244
1841   0244          'set for reagent name and highlight it
1841   0244          MENU% = 6:COLOR 0,7
1854   0244          GOSUB DISPMENU
185A   0244
185A   0244          SCREEN 0,0,0,0
186F   0244          RETURN
1873   0244   REM $PAGE
1873   0244   DISPMENU:
1878   0244          LOCATE (MENU% MOD 6)*2+7,(INT(MENU%/6)*28+2)+15*INT(MENU%/12)
18D4   0244          PRINT MENU$(MENU%,0)
18F2   0244          IF MENU% > 5 THEN GOTO SHOWSTRING:'   no value to display
1901   0244          LOCATE (MENU% MOD 6)*2+7,MENU(MENU%,4)
1933   0244          PRINT USING MENU$(MENU%,1);MENU(MENU%,0);
1966   0244          IF MENU% > 2 THEN RETURN
1975   0244          ON MENU%+1 GOSUB SET.FREQ, SET.AMP, SET.DELAY
1986   0244          RETURN
198A   0244   SHOWSTRING:
198F   0244          IF MENU% > 10 THEN RETURN
199E   0244          LOCATE (MENU% MOD 6)*2+7,48
19BA   0244          PRINT "          "
19C7   0244          LOCATE (MENU% MOD 6)*2+7,48
19E3   0244          PRINT MENU$(MENU%,1)
1A02   0244          RETURN
1A06   0244
1A06   0244   SET.FREQ:
1A08   0244          TEMP = MENU(0,0)
1A24   0244          CALL SET.DOT.RATE(TEMP):       'in module PCI
1A34   0244          LED% = 3-INT((TEMP+500)/1000)
1A57   0246          IF LED% < 0 THEN LED% = 0
1A69   0246          SCR% = 4 + (LED% * 32):        'set LED intensity
1A89   0246          CALL DIGITAL.OUT(SCR%):        'in module PCI
```

```
1A99   0246           RETURN
1A9D   0246
1A9D   0246   SET.AMP:
1AA2   0246           SCR% = CINT(MENU(MENU%,0) * 255 / 150):      'convert volts to binary number
1ACB   0246           IF SCR% = OLD.AMP.VALUE% THEN RETURN
1ADC   0246           TEMP% = SCR% - OLD.AMP.VALUE%:              'calculate delta
1AE8   0248           OLD.AMP.VALUE% = SCR%:                      'update old value to current value
1AEF   0248           DIG.VAL% = 6
1AF6   024A           IF TEMP% < 0 THEN DIG.VAL% = 5
1B08   024A           TEMP% = ABS(TEMP%)
1B15   024A           FOR I% = 1 TO TEMP%
1B22   024C                  SCR% = DIG.VAL% + (32*LED%)
1B3F   024C                  CALL DIGITAL.OUT(SCR%):             'pulse higher or lower
1B4F   024C                  SCR% = 4 + (32 * LED%)
1B6F   024C                  CALL DIGITAL.OUT(SCR%):             'set port to normal
1B7F   024C           NEXT I%
1B91   024C           RETURN
1B95   024C
1B95   024C   SET.DELAY:
1B9A   024C           TEMP = MENU(2,0)
1BB6   024C           CALL SET.STROBE.DELAY(TEMP):      'in module PCI
1BC6   024C           RETURN
1BCA   024C
1BCA   024C   REM $PAGE
1BCA   024C   '************ DATA USED BY THIS MODULE ************
1BCA   024C
1BCA   024C   ARRDATA:
1BCF   024C           DATA "Frequency            Hz","##,###",10000,1,1,16
1BD1   024C           DATA "Amplitude            V ","###",150,0,1,19
1BD3   024C           DATA "Strobe Delay         uS","##,###.#",15999.5,.5,.5,16
1BD5   024C           DATA "Pulse Width          ","###",999,0,1,19
1BD7   024C           DATA "Rise Time            ","###",999,0,1,19
1BD9   024C           DATA "Fall Time            ","###",999,0,1,19
1BDB   024C           DATA "Name","",0,0,0,0
1BDD   024C           DATA "Concentration","",0,0,0,0
1BDF   024C           DATA "Density","",0,0,0,0
1BE1   024C           DATA "Viscosity","",0,0,0,0
1BE3   024C           DATA "Surface Tension","",0,0,0,0
1BE5   024C           DATA "","",0,0,0,0
1BE7   024C           DATA "START","",0,0,0,0
1BE9   024C           DATA "LOAD","",0,0,0,0
1BEB   024C           DATA "SAVE","",0,0,0,0
1BED   024C           DATA "EXIT","",0,0,0,0
1BEF   024C           DATA "","",0,0,0,0
1BF1   024C           DATA "","",0,0,0,0
1BF3   024C
1BF3   024C   TABLE:
1BFB   024C           DATA 3,1,218
1BFA   024C           DATA 3,28,210
1BFC   024C           DATA 3,69,210
1BFE   024C           DATA 3,80,191
1C00   024C           DATA 5,1,198
1C02   024C           DATA 5,28,206
1C04   024C           DATA 5,69,206
1C06   024C           DATA 5,80,181
1C08   024C           DATA 19,1,192
1C0A   024C           DATA 19,28,208
1C0C   024C           DATA 19,69,208
1C0E   024C           DATA 19,80,217
1C10   024C
1C10   024C   END SUB
1C17   024C
1C17   024C
23E8   024C 50426 Bytes Available
43960 Bytes Free 0 Warning Error(s)
  0 Severe  Error(s)
```

Reagent Jet Printer
Pattern Entry/Modification

| Offset | Data | Source Line | IBM Personal Computer BASIC Compiler V2.00 |
|---|---|---|---|
| 0030 | 0006 | REM $TITLE:'Reagent Jet Printer' $SUBTITLE:'Pattern Entry/Modification' | |
| 0030 | 0006 | 'MODULE   - "PATENT" Pattern creation, modification, and filing | |
| 0030 | 0006 | ' | |
| 0030 | 0006 | ' | |
| 0030 | 0006 | 'AUTHOR   - N. A. Enevold | |
| 0030 | 0006 | ' | |
| 0030 | 0006 | 'COPYRIGHT (C) 1985 ABBOTT LABORATORIES | |
| 0030 | 0006 | ' | |
| 0030 | 0006 | 'REVISION - 1.2 03-10-86 NAE Remove Mouse inputs | |
| 0030 | 0006 | '            1.1 02-20-86 NAE Add 80 pattern limit to save | |
| 0030 | 0006 | '            1.0 01-13-86 NAE Creation of initial code | |
| 0030 | 0006 | ' | |
| 0030 | 0006 | 'SYSTEM   - This code can only be compiled by the BASCOM | |
| 0030 | 0006 | '            COMPILER, it will not run under the INTERPRETER!! | |
| 0030 | 0006 | ' | |
| 0030 | 0006 | 'DESCRIPTION: | |
| 0030 | 0006 | '     This module allows the user to LOAD, SAVE, DIRectory, DRAW and | |
| 0030 | 0006 | '     enter repeat count and other parameters for a pattern to be printed. | |
| 0030 | 0006 | '     The low-resolution graphics mode is selected and a menu is displayed | |
| 0030 | 0006 | '     across the bottom of the screen. Using arrow keys | |
| 0030 | 0006 | '     point to the action to be taken and then invoke that action with the | |
| 0030 | 0006 | '     Enter key. In the DRAW mode, another menu is | |
| 0030 | 0006 | '     displayed which allows the user to select from LINE, RECTangle, | |
| 0030 | 0006 | '     Solid RECTangle, or CIRCLe pattern elements. | |
| 0030 | 0006 | ' | |
| 0030 | 0006 | 'DATA DICTIONARY | |
| 0030 | 0006 | '     SCNDAT%(50,5)   51 Row (Elements) by 6 Column array for storing pattern elements | |
| 0030 | 0006 | '     CURSOR%(9)      Storage for cursor graphics icon | |
| 0030 | 0006 | '     MENU$(6)        Up to 7 menu names can be saved here | |
| 0030 | 0006 | '     ELNUM%          Count of number of elements in a pattern | |
| 0030 | 0006 | '     X% Y%           Current location of graphics cursor | |
| 0030 | 0006 | '     GRID            Value of one dot space on the screen (default is 0.005") | |
| 0030 | 0006 | '     ROW% COL%       Location to print instructions | |
| 0030 | 0006 | '     A$              Storage for single key-strokes or input strings | |
| 0030 | 0006 | '     MENUNUM         Which menu is being displayed (1 or 2) | |
| 0030 | 0006 | '     ITEM            Pointer to which menu item is highlighted (0 - 6) | |
| 0030 | 0006 | '     REPEAT%         Number of times pattern is to be repeated when printed | |
| 0030 | 0006 | '     XOFF YOFF       X and Y axis distance between the printing of repeated patterns | |

```
0030  0006   '      ROWSP COLSP      Row and Column spacing for printing m
              ultiple sets of patterns
0030  0006   '      PATNUM%              Number of patterns stored in
              the pattern directory PATDIR.RJP
0030  0006   '      DROW%  DCOL%    Row and Column location to display di
              rectory entrys
0030  0006   '      NAME$           Pattern name to be LOADed or SAVEd to
               directory
0030  0006   '      I%  J%          Counters used to LOAD or SAVE the ele
              ment data from/to pattern data file
0030  0006   '      FILE$           Name of pattern data file
0030  0006   '      TEMP%           Which type of element is being drawn.
               1 = Line   2 = Rectangle
0030  0006   '
              3 = Solid Rectangle  4 = Circle
0030  0006   '      FLAG%           Same as TEMP% above
0030  0006   '      STARTMSG$ ENDMSG$ Message display for startpoint and en
              dpoint of element entry
0030  0006   '      X1% Y1%             Starting cursor position for
              element being drawn
0030  0006   '      DX% DY%             Delta X and Y values used to
              re-position cursor after arrow key
0030  0006   '      MAXITEM             The highest number item in th
              e current menu display
0030  0006   '      XS  XE          Starting and ending X position of the
              menu highlighting blue box
0030  0006   '      RADIUS%             The calculated radius of a ci
              rcle to be displayed
0030  0006   REM $PAGE
0030  0006   SUB PATENTRY STATIC
0047  0006
0047  0006           WIDTH 40:SCREEN 1:CLS
005F  0006           DIM SCNDAT%(50,5),CURSOR%(9),MENU$(6)
0060  029A           ELNUM% = 0:X%=0:Y%=0:GRID = 0.005
007F  02A4
007F  02A4           LINE (0,0)-(6,6),,B
00A1  02A4           LINE (0,3)-(6,3),,B
00C5  02A4           LINE (3,0)-(3,6),,B
00E9  02A4           PRESET (3,3)
00F5  02A4           GET (0,0)-(6,6),CURSOR%
0116  02A4           CLS
011D  02A4
011D  02A4           LINE (0,0)-(319,190),,B
0140  02A4
0140  02A4           RESTORE INSTRUC
0147  02A4           FOR I=1 TO 4
0151  02A4               READ ROW%,COL%,A$
0164  02AC              LOCATE ROW%,COL%:PRINT A$;
0180  02AC           NEXT I
019B  02B0
019B  02B0   FIRST:
01A0  02B0           MENUNUM = 1
01AA  02B4           GOSUB SUBMENU
01B0  02B4
01B0  02B4           ON ITEM + 1 GOTO PATDIR, PATLOAD, PATSAVE, PATDRAW, REP
              EAT, PATEXT
```

```
01CD    02B8            GOTO FIRST
01D0    02B8
01D0    02B8    REPEAT:
01D5    02B8            GOSUB ITEMBOXERASE:     'erase blue box around DIR
01DB    02B8            LOCATE 25,1:PRINT SPACE$(39);   'erase menu line
01FB    02B8            LOCATE 25,1:INPUT;"Enter Repeat Count ",REPEAT%
0218    02BA            LOCATE 25,1:PRINT SPACE$(39);   'erase menu line
0235    02BA            LOCATE 25,1:INPUT;"Enter X Axis Offset ",XOFF
0255    02BE            LOCATE 25,1:PRINT SPACE$(39);   'erase menu line
0272    02BE            LOCATE 25,1:INPUT;"Enter Y Axis Offset ",YOFF
0292    02C2            GOTO FIRST
0296    02C2    PATEXT:
029B    02C2            WIDTH 80:SCREEN 0:CLS
02B2    02C2            EXIT SUB
02B6    02C2    REM $PAGE
02B6    02C2    PATDIR:                 'list directory of patterns
02BB    02C2            GOSUB ITEMBOXERASE:     'erase blue box around DIR
02C1    02C2            LOCATE 25,1:PRINT SPACE$(39);   'erase menu line
02DE    02C2            OPEN "PATDIR.RJP" FOR INPUT AS #1:      'open directory
                file
02EF    02C2            INPUT #1, PATNUM%:      'read number of patterns in dir
                ectory
0301    02C4            LINE (1,1)-(318,189),0,BF:      'erase graphics tablet
0326    02C4            I = 0:                  'set counter
0330    02C4
0330    02C4    DISLOOP:
0335    02C4            I = I + 1:              'set for next value
0344    02C4            IF I > PATNUM% THEN GOTO DIREXIT:       'test for done
035B    02C4            IF INT((I-1)/44) <> (I-1)/44 THEN GOTO SHOWNEXT
0384    02C4            IF INT((I-1)/44) < 1 THEN GOTO SHOWNEXT
03A9    02C4
03A9    02C4            LOCATE 25,1:PRINT "More to Display. Continue ? (Y or N)
                ";
03C3    02C4            GOSUB CORLOOP:  'wait for Y or N response
03C9    02C4            IF A$ = "N" THEN GOTO DIREXIT:  'if N then don't contin
                ue
03DC    02C4
03DC    02C4            LINE (1,1)-(318,189),0,BF:      'erase graphics tablet
0401    02C4
0401    02C4    SHOWNEXT:
0406    02C4            DROW% = ((I - 1) MOD 22) + 2:   'calculate row for disp
                lay
0422    02C6            DCOL% = 4:                      'set column to 4
0429    02C8            IF ((I - 1) MOD 44) > 21 THEN DCOL% = 23:'reset column
                if necessary
044C    02C8
044C    02C8            LINE INPUT #1, A$:      'read next name from directory
0459    02C8            LOCATE DROW%,DCOL%:PRINT A$;    'PRINT NAME
0475    02C8            GOTO DISLOOP
0479    02C8
0479    02C8    DIREXIT:
047E    02C8            CLOSE #1:       'terminate access to PATDIR.RJP
0485    02C8            GOTO FIRST
0489    02C8
0489    02C8    REM $PAGE
0489    02C8    PATLOAD:
048E    02C9            GOSUB ITEMBOXERASE:     'erase blue box around DIR
```

```
0494   02C8            OPEN "PATDIR.RJP" FOR INPUT AS #1
04A5   02C8            INPUT #1,PATNUM%:        'read number of patterns in dir
04B7   02C8            GOSUB GETNAME:           'prompt for and input pattern n
                ame
04BD   02C8            LINE (1,1)-(318,189),0,BF:       'erase graphics tablet
04E2   02C8
04E2   02C8            GOSUB SEARCH
04E8   02C8
04E8   02C8            IF I% < (PATNUM% + 1) THEN GOTO FOUND
04FC   02CA            LOCATE 10,16-(LEN(NAME$)/2):PRINT NAME$;" not Found";
0531   02CE            LOCATE 12,14:PRINT "Strike Any Key"
054B   02CE            GOSUB ANYKEY:    'wait for a keyhit
0551   02CE            GOTO FIRST
0555   02CE
0555   02CE   FOUND:
055A   02CE            FILE$ = RIGHT$(STR$(I%),LEN(STR$(I%))-1) + "PAT.RJP"
057E   02D2            OPEN FILE$ FOR INPUT AS #1:      'set pattern data file
                for read
058F   02D2            INPUT #1,ELNUM%:         'read number of elements in pat
                tern
05A1   02D2            INPUT #1,GRID:           'read grid size
05B3   02D2            INPUT #1,REPEAT%:        'read repeat count
05C5   02D2            INPUT #1,XOFF:           'read x axis offset for repeat
05D7   02D2            INPUT #1,YOFF:           'read y axis offset for repeat
05E9   02D2
05E9   02D2            FOR I% = 0 TO ELNUM% - 1
05F7   02D4               FOR J% = 0 TO 5
05FD   02D4                  INPUT #1,SCNDAT%(I%,J%):'read file into screen
                array
0621   02D6               NEXT J%
0631   02D6            NEXT I%
0643   02D6            CLOSE #1:        'done with data file
064A   02D6
064A   02D6            OPEN "PATDEF.RJP" FOR OUTPUT AS #1
065C   02D6            PRINT #1,FILE$:                  'save filename in defau
                lt file
066C   02D6            PRINT #1,NAME$:                  'save the directory nam
                e as well
067C   02D6            CLOSE #1
0683   02D6
0683   02D6            GOTO REDRAW
0687   02D6
0687   02D6   SEARCH:
068C   02D6            I% = 1:                          'set entry pointer
0693   02D6   SLOOP:
0698   02D6            LINE INPUT #1,A$:        'read next pattern name from di
                r
06A5   02D6            IF A$ = NAME$ THEN GOTO SEARCH.END:      'compare name w
                ith dir entry
06B8   02D6            I% = I% + 1
06C1   02D6            IF I% < (PATNUM% + 1) THEN GOTO SLOOP:'check for done
06D4   02D6   SEARCH.END:
06D9   02D6            CLOSE #1:        'not found so close file and display me
                ssage
06E0   02D6            RETURN
06E4   02D6
06E4   02D6   REM $PAGE
```

```
06E4  02D6  PATSAVE:
06E9  02D6         GOSUB ITEMBOXERASE:       'erase blue box around DIR
06EF  02D6         IF ELNUM% = 0 THEN GOTO FIRST:  'no elements in pattern
06FE  02D6         OPEN "PATDIR.RJP" FOR INPUT AS #1
070F  02D6         INPUT #1,PATNUM%
0721  02D6         IF PATNUM% < 80 THEN GOTO SAVE.PAT:    'directory full
             at 80 patterns
0730  02D6         CLOSE #1
0737  02D6         LOCATE 25,1:PRINT SPACE$(39);:         'erase bottom l
             ine
0754  02D6         LOCATE 25,1:PRINT "Directory is full (80 patterns max)"
             ;
076E  02D6         GOSUB ANYKEY:GOTO FIRST
0778  02D6  SAVE.PAT:
077D  02D6         GOSUB GETNAME:   'prompt for and get pattern name
0783  02D6         GOSUB SEARCH
0789  02D6         IF I% > PATNUM% THEN GOTO ADD.NEW.PATTERN
079A  02D6         LINE (1,1)-(318,189),0,BF:     'erase graphics tablet
07BF  02D6         LOCATE 10,13-(LEN(NAME$)/2):PRINT NAME$;" already exist
             s.";
07F4  02D6         LOCATE 12,15:PRINT "Replace it?"
080E  02D6         PATNUM% = I%
0815  02D6         A$ = ""
081F  02D6         WHILE A$ = ""
082E  02D6             A$ = INKEY$
0838  02D6         WEND
083B  02D6         IF A$ = "Y" OR A$ = "y" THEN GOTO SAVE.PATTERN
0864  02D6         GOTO FIRST
0868  02D6
0868  02D6  ADD.NEW.PATTERN:
086D  02D6         KILL "PATDIR.OLD":       'delete old backup directory
0874  02D6         NAME "PATDIR.RJP" AS "PATDIR.OLD":     'save old direc
             tory
087E  02D6         OPEN "PATDIR.OLD" FOR INPUT AS #1
088F  02D6         OPEN "PATDIR.RJP" FOR OUTPUT AS #2:   'set up new dir
08A1  02D6         INPUT #1,PATNUM%:        'read number of dir entries
08B3  02D6         PATNUM% = PATNUM% + 1:   'increase by 1
08BC  02D6         WRITE #2,PATNUM%:        'save in new directory
08CD  02D6         FOR I=1 TO PATNUM% - 1
08E6  02DA             LINE INPUT #1,A$:    'read entry from old dir
08F3  02DA             PRINT #2,A$:         'write entry in new directory
0903  02DA         NEXT I
091E  02DA         PRINT #2,NAME$:          'write new entry to new directo
             ry
092E  02DA         CLOSE #1:CLOSE #2:       'done with directory
093C  02DA  SAVE.PATTERN:
0941  02DA         FILE$ = RIGHT$(STR$(PATNUM%),LEN(STR$(PATNUM%))-1) + "P
             AT.RJP"
0965  02DA         OPEN FILE$ FOR OUTPUT AS #1:   'create new pattern dat
             a file
0977  02DA         WRITE #1,ELNUM%:         'store number of elements
0988  02DA         WRITE #1,GRID:           'store grid dimension
0998  02DA         WRITE #1,REPEAT%:        'store repeat count
09A9  02DA         WRITE #1,XOFF:           'store x axis offset for repeat
09B9  02DA         WRITE #1,YOFF:           'store y axis offset for repeat
09C9  02DA         FOR I% = 0 TO ELNUM% - 1
09D7  02DC             FOR J% = 0 TO 5
```

```
09DD    02DC                WRITE #1,SCNDAT%(I%,J%):         'write screen a
                    rray to file
0A00    02DC                NEXT J%
0A10    02DC                NEXT I%
0A22    02DC                CLOSE #1:       'done with data file
0A29    02DC                OPEN "PATDEF.RJP" FOR OUTPUT AS #1
0A3B    02DC                PRINT #1,FILE$:                  'save filename in defau
                    lt file
0A4B    02DC                PRINT #1,NAME$:                  'save the directory nam
                    e as well
0A5B    02DC                CLOSE #1
0A62    02DC                GOTO FIRST
0A66    02DC    REM $PAGE
0A66    02DC    PATDRAW:
0A6B    02DC                GOSUB ITEMBOXERASE
0A71    02DC                LINE (1,1)-(318,189),0,BF:       'Erase graphics tablet
0A96    02DC
0A96    02DC    NEXTEL:
0A9B    02DC                MENUNUM = 2
0AA5    02DC                GOSUB SUBMENU
0AAB    02DC
0AAB    02DC                ON ITEM + 1 GOTO ALINE, RECT, SRECT, ACIRCLE, REDRAW, B
                    ACKUP
0ACB    02DC                GOTO NEXTEL
0ACB    02DC
0ACB    02DC    BACKUP:
0AD0    02DC                GOSUB ITEMBOXERASE
0AD6    02DC                GOTO FIRST
0ADA    02DC
0ADA    02DC    ALINE:
0ADF    02DC                TEMP% = 1
0AE6    02DE                STARTMSG$ = "STARTING ENDPOINT"
0AF0    02E2                ENDMSG$ = "ENDING ENDPOINT  "
0AFA    02E6                GOTO ENTERELEMENT
0AFE    02E6
0AFE    02E6    RECT:
0B03    02E6                TEMP% = 2
0B0A    02E6                GOTO RECTMSG
0B0E    02E6
0B0E    02E6    SRECT:
0B13    02E6                TEMP% = 3
0B1A    02E6    RECTMSG:
0B1F    02E6                STARTMSG$ = "STARTING CORNER"
0B29    02E6                ENDMSG$ = "ENDING CORNER  "
0B33    02E6                GOTO ENTERELEMENT
0B37    02E6
0B37    02E6    ACIRCLE:
0B3C    02E6                TEMP% = 4
0B43    02E6                STARTMSG$ = "CENTER OF CIRCLE"
0B4D    02E6                ENDMSG$ = "POINT ON CIRCLE  "
0B57    02E6
0B57    02E6    ENTERELEMENT:
0B5C    02E6                GOSUB ITEMBOXERASE
0B62    02E6                FLAG%=0
0B69    02E8                LOCATE 25,1:PRINT SPACE$(39);
0B86    02E8                LOCATE 25,1:PRINT STARTMSG$;
0BA0    02E8                GOSUB DISPCURSOR
```

```
0BA6   02E8   FINDSTART:
0BAB   02E8        GOSUB MOUSEACT
0BB1   02E8        IF A$ = CHR$(27) THEN GOTO ABORT
0BC8   02E8        IF A$ = CHR$(13) THEN GOTO SETSTART
0BDF   02E8        GOSUB CURSORMOVE
0BE5   02E8        GOTO FINDSTART
0BEB   02E8   ABORT:
0BED   02E8        GOSUB PLACECURSOR
0BF3   02E8        GOTO NEXTEL
0BF7   02E8
0BF7   02E8   SETSTART:
0BFC   02E8        LOCATE 25,1:PRINT ENDMSG$;
0C16   02E8        FLAG% = TEMP%:X1% = X%:Y1% = Y%
0C2B   02EC        IF FLAG% = 4 THEN PSET (X%+4,Y%+4)
0C55   02EC   FINDEND:
0C5A   02EC        GOSUB MOUSEACT
0C60   02EC        IF A$ = CHR$(27) THEN GOTO CANCELEL
0C77   02EC        IF A$ = CHR$(13) THEN GOTO SAVEEL
0C8E   02EC        GOSUB CURSORMOVE
0C94   02EC        GOTO FINDEND
0C97   02EC   CANCELEL:
0C9C   02EC        GOSUB PLACECURSOR
0CA2   02EC        ON FLAG% GOSUB ER1, ER2, ER3, ER4
0CB3   02EC        FLAG% = 0
0CBA   02EC        GOTO NEXTEL
0CBE   02EC   SAVEEL:
0CC3   02EC        GOSUB PLACECURSOR
0CC9   02EC        IF FLAG% = 4 THEN CIRCLE (X1%+4,Y1%+4),SQR((X%-X1%)^2+(
               Y%-Y1%)^2),,,,1
0D32   02EC        GOSUB CORRECT
0D38   02EC        IF A$="N" THEN GOTO REDRAW
0D4B   02EC   STOREEL:
0D50   02EC        SCNDAT%(ELNUM%,0) = FLAG%
0D6A   02EC        SCNDAT%(ELNUM%,1) = X1%
0D85   02EC        SCNDAT%(ELNUM%,2) = Y1%
0DA0   02EC        SCNDAT%(ELNUM%,3) = X%
0DBB   02EC        SCNDAT%(ELNUM%,4) = Y%
0DD6   02EC        SCNDAT%(ELNUM%,5) = 0
0DEF   02EC        ELNUM% = ELNUM% + 1
0DF8   02EC        FLAG% = 0
0DFF   02EC        GOTO NEXTEL
0E03   02EC   REM $PAGE
0E03   02EC   REDRAW:
0E08   02EC        GOSUB ITEMBOXERASE
0E0E   02EC        LINE(1,1)-(318,189),0,BF
0E33   02EC        IF ELNUM% = 0 THEN GOTO NEXTEL
0E42   02EC
0E42   02EC        FOR I=0 TO ELNUM%-1
0E5B   02F0            ON SCNDAT%(I,0) GOSUB RD1, RD2, RD3, RD4
0E81   02F0        NEXT I
0E9C   02F0        GOTO NEXTEL
0EA0   02F0
0EA0   02F0   '******** Sub-routines called by main module ********
0EA0   02F0
0EA0   02F0   SUBMENU:
0EA5   02F0
0EA5   02F0        LOCATE 25,1:PRINT SPACE$(39);
```

```
0EC2   02F0           ON MENUNUM GOSUB MENU1, MENU2
0ED1   02F0
0ED1   02F0           FOR I=0 TO 6
0EDB   02F0                   READ MENU$(I)
0EF2   02F0                   LOCATE 25,(I*6)+2:PRINT MENU$(I);
0F2B   02F0           NEXT I
0F46   02F0
0F46   02F0           READ MAXITEM
0F4D   02F4           ITEM = 0
0F57   02F4
0F57   02F4   NEWITEM:
0F5C   02F4           GOSUB NEWITEMBOX
0F62   02F4
0F62   02F4   NEXTITEM:
0F67   02F4           GOSUB ITEMSEARCH
0F6D   02F4           IF A$ = CHR$(13) THEN RETURN:'  ITEM has correct value
0F84   02F4           IF LEN(A$) < 2 THEN BEEP:GOTO NEXTITEM
0F9A   02F4           IF ASC(MID$(A$,2,1)) = 75 THEN GOTO LEFTAR
0FB6   02F4           IF ASC(MID$(A$,2,1)) = 77 THEN GOTO RIGHTAR
0FD2   02F4           BEEP:GOTO NEXTITEM
0FD9   02F4
0FD9   02F4   LEFTAR:
0FDE   02F4           IF ITEM = 0 THEN GOTO NEXTITEM
0FEE   02F4           GOSUB ITEMBOXERASE
0FF4   02F4           ITEM = ITEM - 1
1003   02F4           GOTO NEWITEM
1007   02F4
1007   02F4   RIGHTAR:
100C   02F4           IF ITEM = MAXITEM THEN GOTO NEXTITEM
101F   02F4           GOSUB ITEMBOXERASE
1025   02F4           ITEM = ITEM + 1
1034   02F4           GOTO NEWITEM
1038   02F4
1038   02F4   MENU1:
103D   02F4           RESTORE MN1
1044   02F4           RETURN
1048   02F4
1048   02F4   MENU2:
104D   02F4           RESTORE MN2
1054   02F4           RETURN
1058   02F4
1058   02F4   ITEMSEARCH:
105D   02F4           A$ = INKEY$:IF A$ <> "" THEN RETURN
107A   02F4           GOTO ITEMSEARCH
107D   02F4           RETURN
1081   02F4
1081   02F4   NEWITEMBOX:
1086   02F4           XS = (ITEM*48) + 7
109C   02F8           XE = (ITEM*48) + 8 + LEN(MENU$(ITEM))*8
10D9   02FC           LINE (XS,191)-(XE,199),1,B
1101   02FC           RETURN
1105   02FC
1105   02FC   ITEMBOXERASE:
110A   02FC           LINE (XS,191)-(XE,199),0,B
1131   02FC           RETURN
1135   02FC
1135   02FC   PLACECURSOR:
```

```
113A  02FC         PUT (X%+1,Y%+1),CURSOR%
1157  02FC         RETURN
115B  02FC
115B  02FC  MOUSEACT:
1160  02FC         GOSUB ANYKEY
1166  02FC         DX% = 0 : DY% = 0
1174  0300         IF A$ = CHR$(0) + CHR$(72) THEN DY% = -1:RETURN
119D  0300         IF A$ = CHR$(0) + CHR$(80) THEN DY% =  1:RETURN
11C6  0300         IF A$ = CHR$(0) + CHR$(77) THEN DX% =  1:RETURN
11EF  0300         IF A$ = CHR$(0) + CHR$(75) THEN DX% = -1:RETURN
121B  0300         IF A$ = "8" THEN DY% = -20:RETURN
1232  0300         IF A$ = "2" THEN DY% =  20:RETURN
124C  0300         IF A$ = "4" THEN DX% = -20:RETURN
1266  0300         IF A$ = "6" THEN DX% =  20:RETURN
1280  0300         IF A$ = CHR$(27) THEN RETURN
1297  0300         IF A$ = CHR$(13) THEN RETURN
12AE  0300         GOTO MOUSEACT
12B2  0300
12B2  0300  CURSORMOVE:
12B7  0300         GOSUB PLACECURSOR
12BD  0300         ON FLAG% GOSUB ER1, ER2, ER3, ER4
12CE  0300         X% = X% + DX% : Y% = Y% + DY%
12E6  0300         IF X% < 0 THEN X% = 0
12F8  0300         IF X% > 311 THEN X% = 311
130B  0300         IF Y% < 0 THEN Y% = 0
131D  0300         IF Y% > 182 THEN Y% = 182
1330  0300         ON FLAG% GOSUB DR1, DR2, DR3, DR4
1341  0300         GOSUB DISPCURSOR
1347  0300         RETURN
134B  0300
134B  0300  CORRECT:
1350  0300         LOCATE 25,1:PRINT SPACE$(39);
136D  0300         LOCATE 25,1:PRINT "IS THIS CORRECT? (Y or N) ";
1387  0300  CORLOOP:
138C  0300         GOSUB ANYKEY
1392  0300         IF A$ = "y" OR A$ = "Y" THEN A$ = "Y":GOTO COREXIT
13C5  0300         IF A$ = "n" OR A$ = "N" THEN A$ = "N":GOTO COREXIT
13F8  0300         GOTO CORLOOP
13FB  0300  COREXIT:
1400  0300         LOCATE 25,1:PRINT SPACE$(39);
141D  0300         RETURN
1421  0300
1421  0300  DISPCURSOR:
1426  0300         GOSUB PLACECURSOR
142C  0300         LOCATE 25,27:PRINT USING "+#.###";X% * GRID;
1456  0300         PRINT ",";
1463  0300         PRINT USING "+#.###";Y% * GRID;
1480  0300         RETURN
1484  0300
1484  0300
1484  0300  RD1:
1489  0300         LINE(SCNDAT%(I,1)+4,SCNDAT%(I,2)+4)-(SCNDAT%(I,3)+4,SCN
                DAT%(I,4)+4)
1522  0300         RETURN
1526  0300
1526  0300  RD2:
```

```
152B  0300           LINE(SCNDAT%(I,1)+4,SCNDAT%(I,2)+4)-(SCNDAT%(I,3)+4,SCN
                DAT%(I,4)+4),,B
15C4  0300           RETURN
15C8  0300
15C8  0300  RD3:
15CD  0300           LINE(SCNDAT%(I,1)+4,SCNDAT%(I,2)+4)-(SCNDAT%(I,3)+4,SCN
                DAT%(I,4)+4),,BF
1667  0300           RETURN
166B  0300
166B  0300  RD4:
1670  0300           RADIUS% = SQR((SCNDAT%(I,3)-SCNDAT%(I,1))^2 + (SCNDAT%(
                I,4)-SCNDAT%(I,2))^2)
16FF  0302           CIRCLE (SCNDAT%(I,1)+4,SCNDAT%(I,2)+4),RADIUS%,,,,1
175D  0302           RETURN
1761  0302
1761  0302  DR1:
1766  0302           LINE (X1%+4,Y1%+4)-(X%+4,Y%+4)
17AF  0302           RETURN
17B3  0302
17B3  0302  DR2:
17BB  0302           LINE (X1%+4,Y1%+4)-(X%+4,Y%+4),,B
1801  0302           RETURN
1805  0302
1805  0302  DR3:
180A  0302           LINE (X1%+4,Y1%+4)-(X%+4,Y%+4),,BF
1854  0302           RETURN
185B  0302
185B  0302  DR4:
185D  0302           RETURN
1861  0302
1861  0302  ER1:
1866  0302           LINE (X1%+4,Y1%+4)-(X%+4,Y%+4),0
18AF  0302           RETURN
18B3  0302
18B3  0302  ER2:
18BB  0302           LINE (X1%+4,Y1%+4)-(X%+4,Y%+4),0,B
1901  0302           RETURN
1905  0302
1905  0302  ER3:
190A  0302           LINE (X1%+4,Y1%+4)-(X%+4,Y%+4),0,BF
1954  0302           RETURN
195B  0302
195B  0302  ER4:
195D  0302           RETURN
1961  0302
1961  0302  ANYKEY:
1966  0302           A$ = ""
1970  0302           WHILE A$ = ""
197F  0302                A$ = INKEY$
1989  0302           WEND
198C  0302           RETURN
1990  0302
1990  0302  GETNAME:     'prompt for and get filename
1995  0302           LOCATE 25,1:PRINT SPACE$(39);
19B2  0302           LOCATE 25,38:PRINT "<<";:       'boundry chevron
19CC  0302           LOCATE 25,1:PRINT "Enter Pattern Name   ";
19E6  0302           LINE INPUT; "",NAME$
```

```
19F4   0302          RETURN
19F8   0302
19F8   0302   ' Data fields used by this module
19F8   0302
19F8   0302   MN1:
19FD   0302          DATA "DIR","LOAD","SAVE","DRAW","REPT","EXIT","",5
19FF   0302
19FF   0302   MN2:
1A04   0302          DATA "LINE","RECT","SRECT","CIRCL","REDRW","MAIN","",5
1A06   0302
1A06   0302   INSTRUC:
1A0B   0302          DATA 8,16,"USE ARROWS"
1A0D   0302          DATA 10,9,"TO SELECT FROM THE MENU"
1A0F   0302          DATA 14,12,"USE THE ENTER KEY"
1A11   0302          DATA 16,10,"TO ACTIVATE SELECTION"
1A13   0302
1A13   0302   END SUB
1A1A   0302
21AF   0302
```

50426 Bytes Available
43373 Bytes Free

0 Warning Error(s)
   0 Severe  Error(s)

Reagent Jet Printer
Burr-Brown PCI-20000 custom driver

```
Offset  Data   Source Line        IBM Personal Computer BASIC Compiler V2.00

0030    0006   REM $TITLE:'Reagent Jet Printer' $SUBTITLE:'Burr-Brown PCI-2000
               0 custom driver'
0030    0006   'MODULE   - "PCI" Driver for the PCI-20000 I/O and PULSE cards
0030    0006   '
0030    0006   'AUTHOR   - M. S. Fairchild of Computing Architects Inc.
0030    0006   '                          113 Fairfield Way
0030    0006   '                          Bloomingdale, Il 60108
0030    0006   '                          312/980-6777
0030    0006   '
0030    0006   'COPYRIGHT (C) 1985 ABBOTT LABORATORIES
0030    0006   '
0030    0006   'REVISION - 1.2 12-16-85 MSF Add digital I/O initalization, and
               output routine
0030    0006   '
0030    0006   '         - 1.1 12-10-85 MSF Move counter module to position 2
0030    0006   '
0030    0006   '         - 1.0 11-22-85 MSF Creation of initial code
0030    0006   '
0030    0006   'SYSTEM   - This code can only be compiled by the BASCOM V2
0030    0006   '           COMPILER, it will not run under the INTERPRETER!!
0030    0006   '
0030    0006   'DESCRIPTION:
0030    0006   '           The PCI module is a group of routines used to a
               ccess
```

```
0030  0006   '       the BURR-Brown PCI-20000 board. The supplied software causes
0030  0006   '       the Wordstar2000 software to malfunction and will not privide
0030  0006   '       explicit on, off functions for the counters. Custom drivers
0030  0006   '       will be made to provide all of the desired functions.
0030  0006   '
0030  0006   '
0030  0006   '       Address       Register
0030  0006   '       &HC0000  Carrier I.D. / module present (R)
0030  0006   '       &HC0040  Module interrupt status (R)
0030  0006   '       &HC0080  Digital I/O port 0 (R/W)
0030  0006   '       &HC0081  Digital I/O port 1 (R/W)
0030  0006   '       &HC0082  Buffer direction and enable (R/W)
0030  0006   '       &HC0083  Control for ports 0 and 1 (W)
0030  0006   '       &HC00C0  Digital I/O port 2 (R/W)
0030  0006   '       &HC00C1  Digital I/O port 3 (R/W)
0030  0006   '       &HC00C3  Control for ports 2 and 3 (W)
0030  0006
0030  0006   '       &HC0200       Read module I.D. (1110 1010)
0030  0006   '       &HC0204       Rate generator low-order 16 bits (0)
0030  0006   '       &HC0205       Rate generator high-order 16 bits (1)
0030  0006   '       &HC0206       Counter 3 count register (2)
0030  0006   '       &HC0207       Rate generator/counter 3 control
0030  0006   '       &HC0208       Counter 0 count register (0)
0030  0006   '       &HC0209       Counter 1 count register (1)
0030  0006   '       &HC020A       Counter 2 count register (2)
0030  0006   '       &HC020B       Counter 0 - 2 control
0030  0006   '       &HC020C       Counter gate control (1 enables, 0 disables)
0030  0006   '            bit      function
0030  0006   '            0        Rate generator gate
0030  0006   '            1        Rate generator gate
0030  0006   '            2        Counter 0 gate
0030  0006   '            3        Counter 1 gate
0030  0006   '            4        Counter 2 gate
0030  0006   '            5        Counter 3 gate
0030  0006   '            6        Not used
0030  0006   '            7        Not used
0030  0006   '
0030  0006   '
0030  0006   'DATA DICTIONARY
0030  0006   '
0030  0006   '       COUNT    - Divisor to 2Mhz rate to give desired frequency or time
0030  0006   '       COUNTH%      - High order 16 bits of a 32 bit divisor
0030  0006   '       COUNTL%  - Low order 16 bits of a 32 bit divisor
0030  0006   '       LSB%     - Lower 8 bits of a 16 bit divisor
0030  0006   '       MSB%     - Upper 8 bits of a 16 bit divisor
0030  0006
0030  0006   ' Main line code
0030  0006   '       The main line code is never executed. It's sole purpose it to
0030  0006   ' declare shared the variables that will be used in the subroutines-
```

```
0030   0006         ' so that they will all be defined and hold their values.
0030   0006
0030   0006   MAIN:
0030   0006         DIM SHARED COUNT,COUNTH%,COUNTL%,LSB%,MSB%
0030   0006
0030   0006   MAINLOOP:
0030   0006         GOTO MAINLOOP
004C   0012
004C   0012   REM $PAGE
004C   0012   'SUBROUTINE    - PCI.INIT
004C   0012   '
004C   0012   'DESCRIPTION:
004C   0012   '     The PCI.INIT subroutine initalizes the PCI hardware.
004C   0012
004C   0012   SUB PCI.INIT STATIC
0053   0012
0053   0012         DEF SEG = &HC000: 'Point segment to PCI-20000 board
005A   0012
005A   0012         POKE &H020C,&H00: 'Disable all software enabled counter
                    s
0063   0012
0063   0012   ' Configure rate generator to 2 Mhz
0063   0012
0063   0012         POKE &H0207,&H34: 'Set low rate counter to mode 2
006D   0012         POKE &H0207,&H74: 'Set high rate counter to mode 2
0077   0012         POKE &H0204,&H02: 'Load low rate counter with 16 bits o
                    f 2
0081   0012         POKE &H0204,&H00
008A   0012         POKE &H0205,&H02: 'Load high rate counter with 16 bits
                    of 2
0094   0012         POKE &H0205,&H00
009D   0012         POKE &H020C,&H03: 'Enable rate counters
00A7   0012
00A7   0012   ' Configure dot rate counters (default to 5 Khz)
00A7   0012
00A7   0012         POKE &H020B,&H34: 'Set low dot counter (0) to mode 2
00B1   0012         POKE &H020B,&H74: 'Set high dot counter (1) to mode 2
00BB   0012         POKE &H0208,&H04: 'Load low rate counter with 16 bits o
                    f 4
00C5   0012         POKE &H0208,&H00
00CE   0012         POKE &H0209,&H64: 'Load high rate counter with 16 bits
                    of 100
00D8   0012         POKE &H0209,&H00
00E1   0012
00E1   0012   ' Configure dot pulse with one shot (default to 13 usec)
00E1   0012
00E1   0012         POKE &H020B,&HB2: 'Set dot pulse with oneshot (2) to mo
                    de 1
00EB   0012         POKE &H020A,&H1A: 'Load oneshot with 16 bits of 26
00F5   0012         POKE &H020A,&H00
00FE   0012
00FE   0012   ' Configure shifted strobe pulse one shot (default to .5 usec)
00FE   0012
00FE   0012         POKE &H0207,&HB2: 'Set shifted strobe onshot (3) to mod
                    e 1
0108   0012         POKE &H0206,&H01: 'Load oneshot with 16 bits of 1
```

```
0112  0012        POKE &H0206,&H00
011B  0012
011B  0012  ' Configure port 0 to output and port 1 to input
011B  0012
011B  0012        POKE &H0083,&H82: ' Set up I/O chip
0125  0012        POKE &H0082,&H34: ' Set up direction and enable buffers
012F  0012        POKE &H0080,&H00: ' Dissable print head
0136  0012        END SUB
013F  0012
013F  0012  REM $PAGEIF:12
013F  0012  'SUBROUTINE    - DOT.ON
013F  0012  '
013F  0012  'DESCRIPTION:
013F  0012  '     The DOT.ON subroutine enables the dot frequency counters.
013F  0012
013F  0012  SUB DOT.ON STATIC
0146  0012
0146  0012        POKE &H020C,&H0F: 'Enable dot counters and rate generator
0150  0012
0150  0012        END SUB
0157  0012
0157  0012  REM $PAGEIF:12
0157  0012  'SUBROUTINE    - DOT.OFF
0157  0012  '
0157  0012  'DESCRIPTION:
0157  0012  '     The DOT.OFF subroutine disables the dot counters
0157  0012
0157  0012  SUB DOT.OFF STATIC
015E  0012
015E  0012        POKE &H020C,&H03: 'Disable dot counters and enable rate generator
0168  0012
0168  0012        END SUB
016F  0012
016F  0012  REM $PAGEIF:49
016F  0012  'SUBROUTINE    - SET.DOT.RATE
016F  0012  '
016F  0012  'DESCRIPTION:
016F  0012  '     The SET.DOT.RATE subroutine loads the dot rate counters
016F  0012  ' with the desired dot frequency. Allowed range is 10,000 to 1 Hz.
016F  0012  ' The FREQ parameter is a real number in Hz.
016F  0012
016F  0012  SUB SET.DOT.RATE(FREQ) STATIC
0176  0012
0176  0012  ' Limit freqency to in range
0176  0012
0176  0012        IF FREQ < 1 THEN FREQ = 1
018F  0012        IF FREQ > 10000 THEN FREQ = 10000
01A8  0012
01A8  0012  ' Convert to count and check for 16 bit count or 32 bit count
01A8  0012
01A8  0012        COUNT = 2E6 / FREQ
01B8  0012        IF COUNT < 65536! THEN GOTO DIVIDE16 ELSE GOTO DIVIDE32
01CF  0012
```

```
01CF   0012    ' Process count of 32 bits
01CF   0012
01CF   0012    DIVIDE32:
01D0   0012            COUNTL% = INT((COUNT/32768!) + 1): 'Stage lower count
01F0   0012            COUNTH% = INT(COUNT/COUNTL%): 'Form upper count
020B   0012            GOTO SET.COUNT
020F   0012
020F   0012    ' Process count of 16 bits
020F   0012
020F   0012    DIVIDE16:
0214   0012            COUNTL% = 2
021B   0012            COUNTH% = INT(COUNT/2)
0232   0012            GOTO SET.COUNT
0236   0012
0236   0012    ' Send the derived counts out to the counters
0236   0012
0236   0012    SET.COUNT:
0237   0012            LSB% = COUNTL% MOD 256: ' Send out low 16 bits
0248   0012            MSB% = INT(COUNTL% / 256)
0263   0012            POKE &H0208,LSB%
0273   0012            POKE &H0208,MSB%
0283   0012
0283   0012            LSB% = COUNTH% MOD 256: 'Send out high 16 bits
0291   0012            MSB% = INT(COUNTH% / 256)
02AC   0012            POKE &H0209,LSB%
02BC   0012            POKE &H0209,MSB%
02CC   0012
02CC   0012            END SUB
02D3   0012
02D3   0012    REM $PAGEIF:27
02D3   0012    'SUBROUTINE    - SET.DOT.WIDTH
02D3   0012    '
02D3   0012    'DESCRIPTION:
02D3   0012    '        The SET.DOT.WIDTH subroutine loads the dot width one shot
02D3   0012    ' with the desired dot pulse width. Allowed range is .5 to 16,000 usec.
02D3   0012    ' The dwidth parameter is a real number in usec.
02D3   0012
02D3   0012    SUB SET.DOT.WIDTH(DWIDTH) STATIC
02DA   0012
02DA   0012    ' Limit width to in range
02DA   0012
02DA   0012            IF DWIDTH < .5 THEN DWIDTH = .5
02F3   0012            IF DWIDTH > 16000 THEN DWIDTH = 16000
030C   0012
030C   0012    ' Convert to count
030C   0012
030C   0012            COUNT = DWIDTH / .5
031A   0012
031A   0012    ' Send the derived count out to the counter
031A   0012
031A   0012            LSB% = INT(COUNT MOD 256): ' Send out 16 bits
0331   0012            MSB% = INT(COUNT / 256)
0348   0012            POKE &H020A,LSB%
0358   0012            POKE &H020A,MSB%
0368   0012
```

```
0368  0012           END SUB
036F  0012
036F  0012   REM $PAGEIF:27
036F  0012   'SUBROUTINE    - SET.STROBE.DELAY
036F  0012   '
036F  0012   'DESCRIPTION:
036F  0012   '     The SET.STROBE.DELAY subroutine loads the strobe delay one shot
036F  0012   ' with the desired strobe delay time. Allowed range is .5 to 16,000 usec.
036F  0012   ' The delay parameter is a real number in usec.
036F  0012
036F  0012   SUB SET.STROBE.DELAY(DELAY) STATIC
0376  0012
0376  0012   ' Limit delay to in range
0376  0012
0376  0012           IF DELAY < .5 THEN DELAY = .5
038F  0012           IF DELAY > 16000 THEN DELAY = 16000
03A8  0012
03A8  0012   ' Convert to count
03A8  0012
03A8  0012           COUNT = DELAY / .5
03B6  0012
03B6  0012   ' Send the derived count out to the counter
03B6  0012
03B6  0012           LSB% = INT(COUNT MOD 256): ' Send out 16 bits
03CD  0012           MSB% = INT(COUNT / 256)
03E4  0012           POKE &H0206,LSB%
03F4  0012           POKE &H0206,MSB%
0404  0012
0404  0012           END SUB
040B  0012
040B  0012   REM $PAGEIF:16
040B  0012   'SUBROUTINE    - DIGITAL.OUT
040B  0012   '
040B  0012   'DESCRIPTION:
040B  0012   '     The DIGITAL.OUT subroutine sends the passed integer to the output
040B  0012   '     port 0.
040B  0012
040B  0012   SUB DIGITAL.OUT(BYTE%) STATIC
0412  0012
0412  0012   ' Send the byte to the port
0412  0012
0412  0012           POKE &H0080,BYTE%
0423  0012
0423  0012           END SUB
042A  0012
057F  0012
```

50426 Bytes Available
48720 Bytes Free

0 Warning Error(s)
0 Severe Error(s)

Reagent Jet Printer
Pattern Printing

Offset  Data   Source Line                                          IBM Personal Computer BASIC Compiler V2.00

```
0030  0006   REM $TITLE:'Reagent Jet Printer' $SUBTITLE:'Pattern Printing' $LINESIZE:132
0030  0006   'MODULE   - "PATPRINT"
0030  0006   '
0030  0006   'AUTHOR   - N. A. Enevold
0030  0006   '
0030  0006   'COPYRIGHT (C) 1985 ABBOTT LABORATORIES
0030  0006   '
0030  0006   'REVISION - 2.0 07-02-86 NAE Modified for MicroFab Printhead
0030  0006   '         - 1.1 03-07-86 NAE Added notes and final touches
0030  0006   '           1.0 02-03-86 NAE Creation of initial code
0030  0006   '
0030  0006   'SYSTEM   - This code can only be compiled by the BASCOM
0030  0006   '            COMPILER, it will not run under the INTERPRETER!!
0030  0006   '
0030  0006   'DESCRIPTION:
0030  0006   '     The printing module displays a menu in 3 columns of 4 rows each.  The first
0030  0006   '     column has data from the default reagent profile.  The second column has
0030  0006   '     data from the default pattern file.  The third column has standard printing
0030  0006   '     data.  The four arrow keys allow different menu items to be highlighted and
0030  0006   '     the values can be changed with the + or - keys or by entering the new number
0030  0006   '     followed by Enter.  P will cause the pattern to be printed, S will select the
0030  0006   '     notepad, and E will exit to the main program.  On the notepad, any single line
0030  0006   '     entered here will be sent to the printer.  A null line exits the notepad.
0030  0006   '
0030  0006   'DATA DICTIONARY
0030  0006   '     MENU%         Which menu item is highlighted (0-17)
0030  0006   '     DIFF%         Where to move menu highlight in response to arrow key
0030  0006   '     TYPE%         What key has been pressed during main scan
0030  0006   '     ELNUM%        Number of elements in current pattern
0030  0006   '     SCNDAT%(50,5) Array for storing elements in current pattern
0030  0006   '     REPEAT%       Counter for repeat printing the pattern
0030  0006   '     CT%           Counter for stepping through the pattern array during printing
0030  0006   '     RADIUS%       Radius of circle during printing
0030  0006   '     X% Y%         Offsets for start row/column position
0030  0006   '     REPX% REPY%   Repeat distances for repeat printing of patterns
0030  0006   '     SX% SY%       Starting X and Y positions for solid rectangles
0030  0006   '     EX% EY%       Ending X and Y positions for solid rectangles
0030  0006   '     I% J%         Counters used for reading pattern files into the array
0030  0006   '     TEMP%         Register for misc. integers
0030  0006   '     NOTELINE%     Pointer to which line is active in the notepad
0030  0006   '     MENU$(17,1)   Array of strings used to display menu items
0030  0006   '     A$            Single keystroke input destination
0030  0006   '     NOTE$         String entered in notepad and sent to printer
0030  0006   '     KEYBUF$       String entered from main scan and assigned to number of string field
0030  0006   '     REANAME$      Name of default reagent
0030  0006   '     PATNAME$      Name of default pattern
0030  0006   '     FILE$         Name of reagent data file and then pattern data file
0030  0006   '     MENU(11,4)    Array of values used in displaying menu item numbers
0030  0006   '     TEMP          Register for the temporary storage of real numbers
0030  0006   REM $PAGE
0030  0006   SUB PATPRINT STATIC
0047  0006
0047  0006        DIM SCNDAT%(50,5),MENU$(17,1),MENU(17,4)
0048  0462
0048  0462        GOSUB INITIALIZE:       'read init. values and set screen
004E  0462
004E  0462        WHILE TYPE% <> 1
0059  0464
0059  0464           TYPE% = 0
0060  0464           A$ = ""
006A  0468
006A  0468           WHILE A$ = ""
0079  0468              A$ = INKEY$
0083  0468           WEND
```

```
0086   0468
0086   0468         IF A$ = "E" OR A$ = "e" THEN TYPE% = 1:      'exit sub
00B2   0468         IF A$ = "P" OR A$ = "p" THEN TYPE% = 2:      'print pattern
00DE   0468         IF A$ = "+" THEN TYPE% = 3:                  'increment variable
00F4   0468         IF A$ = "-" THEN TYPE% = 4:                  'decrement variable
010A   0468         IF A$ = CHR$(0) + CHR$(72) THEN TYPE% = 5:   'up arrow key
012F   0468         IF A$ = CHR$(0) + CHR$(80) THEN TYPE% = 6:   'down arrow key
0154   0468         IF A$ = CHR$(0) + CHR$(75) THEN TYPE% = 7:   'left arrow key
0179   0468         IF A$ = CHR$(0) + CHR$(77) THEN TYPE% = 8:   'right arrow key
019E   0468         IF A$ > CHR$(47) AND A$ < CHR$(58) THEN TYPE% = 9:' number 0-9
01D6   0468         IF A$ = "S" OR A$ = "s" THEN TYPE% = 10:     'enter scratchpad
0202   0468
0202   0468         ON TYPE% GOSUB T1, T2, T3, T4, T5, T6, T7, T8, T9, T10
021F   0468
021F   0468         WEND
0223   0468         TYPE% = 0
022A   0468
022A   0468         EXIT SUB
022E   0468
022E   0468   '*********** SUBROUTINES FOR THIS MODULE ***********
022E   0468   T10:  'scratch pad
0233   0468         SCREEN 0,0,2,2:COLOR 7,0
0256   0468         LOCATE NOTELINE%,1
0264   046A   NOTELOOP:
0269   046A         LINE INPUT NOTE$
0277   046E         IF NOTE$ = "" THEN SCREEN 0,0,0,0:RETURN
029F   046E         LPRINT NOTE$
02AC   046E         IF NOTELINE% < 24 THEN NOTELINE% = NOTELINE% + 1
02C0   046E         GOTO NOTELOOP
02C3   046E
02C3   046E
02C3   046E   T1:
02C8   046E         RETURN:              'exit to print menu, no action
02CC   046E
02CC   046E   T3:         'process "+" key
02D1   046E         IF MENU(MENU%,0) >= MENU(MENU%,1) THEN MENU(MENU%,0) = MENU(MENU%,1):RETURN:   'check max value
033C   0470         MENU(MENU%,0) = MENU(MENU%,0) + MENU(MENU%,3):  'add increment
0372   0470         COLOR 0,7:GOSUB DISPMENU:RETURN:                'show new value
0388   0470
0388   0470   T4:         'process "-" key
038D   0470         IF MENU(MENU%,0) <= MENU(MENU%,2) THEN MENU(MENU%,0) = MENU(MENU%,2):RETURN:   'check min value
03F8   0470         MENU(MENU%,0) = MENU(MENU%,0) - MENU(MENU%,3):  'sub increment
042E   0470         COLOR 0,7:GOSUB DISPMENU:RETURN:                'show new value
0444   0470
0444   0470   T5:         'process up arrow key
0449   0470         IF MENU% MOD 6 = 0 THEN RETURN:          'in top row already
045E   0470         DIFF% = -1:GOSUB NEWMENU:RETURN:         'move pointer up one
046F   0472
046F   0472   T6:         'process down arrow key
0474   0472         IF MENU% MOD 6 = 5 THEN RETURN:          'in bottom row already
048A   0472         DIFF% = 1:GOSUB NEWMENU:RETURN:          'move pointer down one
049B   0472
049B   0472   T7:         'process left arrow key
04A0   0472         IF INT(MENU% / 6) = 0 THEN RETURN        'in left column already
04C0   0472         DIFF% = -6:GOSUB NEWMENU:RETURN:         'move pointer one left
04D1   0472
04D1   0472   T8:         'process right arrow key
04D6   0472         IF INT(MENU% / 6) = 2 THEN RETURN        'in right column already
04F9   0472         DIFF% = 6:GOSUB NEWMENU:RETURN:          'move pointer one right
050A   0472
050A   0472   T9:         'input keys into KEYBUF$ until <cr> is entered
050F   0472         LOCATE 25,30:COLOR 31,0:PRINT "ENTER NEW VALUE";:COLOR 15,0
0541   0472         KEYBUF$ = A$
054B   0476         WHILE A$ <> CHR$(13)
055E   0476             LOCATE 25,47:PRINT SPACE$(20);
057B   0476             LOCATE 25,47:PRINT KEYBUF$;
0595   0476             A$ = ""
059F   0476             WHILE A$ = ""
05AE   0476                 A$ = INKEY$
```

```
05BB  0476           WEND
05BB  0476           IF A$ = CHR$(8) AND LEN(KEYBUF$) > 0 THEN KEYBUF$ = LEFT$(KEYBUF$,LEN(KEYBUF$)-1)
05FD  0476           IF A$ > CHR$(31) THEN KEYBUF$ = KEYBUF$ + A$
061E  0476       WEND
0622  0476       TEMP = VAL(KEYBUF$)       'temp has value of keys input
0632  047A
0632  047A       'round off temp according to step size in menu array
0632  047A       TEMP = INT(TEMP / (MENU(MENU%,3)) + .5) * MENU(MENU%,3)
066B  047A
066B  047A       'test TEMP for maximum and minimum values in menu array
066B  047A       IF TEMP > MENU(MENU%,1) THEN TEMP = MENU(MENU%,1)
06AA  047A       IF TEMP < MENU(MENU%,2) THEN TEMP = MENU(MENU%,2)
06E9  047A
06E9  047A       'insert new value into menu array and update screen
06E9  047A       MENU(MENU%,0) = TEMP
0705  047A       LOCATE 25,30:PRINT SPACE$(40);
0722  047A       COLOR 0,7:GOSUB DISPMENU
0734  047A       RETURN
0738  047A
0738  047A  T2:  'set Burr-Brown board then print desired pattern
073D  047A
073D  047A       BEEP:COLOR 15,0:LOCATE 25,1
075A  047A       PRINT "Set Potentiometers on Printer....then Press any Key";
0767  047A       A$ = ""
0771  047A       WHILE A$ = ""
0780  047A           A$ = INKEY$
078A  047A       WEND
078D  047A       LOCATE 25,1:PRINT SPACE$(79);
07AA  047A
07AA  047A       'enter drop parameters into burr-brown board
07AA  047A       TEMP = MENU(0,0):CALL SET.DOT.RATE(TEMP)
07D3  047A       TEMP = 5:CALL SET.DOT.WIDTH(TEMP)
07ED  047A       TEMP = MENU(2,0):CALL SET.STROBE.DELAY(TEMP)
0819  047A       CALL DOT.ON
0825  047A
0825  047A       TEMP% = 4
082C  047C       CALL DIGITAL.OUT(TEMP%)
083C  047C       TEMP% = 0:                'pulse RESET line
0843  047C       CALL DIGITAL.OUT(TEMP%)
0853  047C       TEMP% = 4
085A  047C       CALL DIGITAL.OUT(TEMP%)
086A  047C
086A  047C       J% = CINT(MENU(1,0) * 255 / 150): 'set pulse amplitude by pulsing HIGHER signal J% number of times
0893  047E       FOR I% = 1 TO J%
08A0  0480           TEMP% = 6:            'set HIGHER true
08A7  0480.          CALL DIGITAL.OUT(TEMP%)
08B7  0480           TEMP% = 4:            'set HIGHER false
08BE  0480           CALL DIGITAL.OUT(TEMP%)
08CE  0480       NEXT I%
08E0  0482
08E0  0482       'establish COM1: and initialize plotter
08E0  0482       OPEN "COM1:2400,N,8,2,CS 65535" AS #1
08F2  0482       PRINT #1,";:UEC5,EFV1,H";
0902  0482
0902  0482       'move nozzle offset and establish new origin
0902  0482       PRINT #1,"AO";
0912  0482
0912  0482       'calculate row/column location, move there, and set new origin
0912  0482       X% = (MENU(12,0)-1) * (MENU(14,0) / 0.005)
0954  0484       Y% = (MENU(13,0)-1) * (MENU(15,0) / 0.005)
0996  0486       PRINT #1,X%;Y%;"O";
09B4  0486
09B4  0486       'print the pattern using repeat count
09B4  0486       REPY% = MENU(8,0) / 0.005
09D7  0488       REPX% = MENU(9,0) / 0.005
09FA  048A
09FA  048A       FOR REPEAT% = 0 TO MENU(7,0)
0A1C  048C
0A1C  048C           'print the pattern
```

```
0A1C   048C                FOR CT% = 0 TO ELNUM% - 1
0A2A   0490                    ON SCNDAT%(CT%,0) GOSUB PLINE, PRECT, PSRECT, PCIRCL
0A4C   0492                NEXT CT%
0A5E   0492
0A5E   0492                PRINT #1,"A,0,0,";:      'return to origin
0A6E   0492                PRINT #1,REPX%;REPY%;"0";:  'move to next pattern
0A8C   0492            NEXT REPEAT%
0AA1   0494
0AA1   0494            PRINT #1,"H";:   'return plotter to original HOME
0AB1   0494
0AB1   0494            CLOSE #1:        'disable com1:
0AB8   0494
0AB8   0494            RETURN
0ABC   0494
0ABC   0494   PLINE:
0AC1   0494            PRINT #1,SCNDAT%(CT%,2);SCNDAT%(CT%,1);"D";
0B03   0494            PRINT #1,SCNDAT%(CT%,4);SCNDAT%(CT%,3);"U";
0B45   0494            RETURN
0B49   0494
0B49   0494   PRECT:
0B4E   0494            PRINT #1,SCNDAT%(CT%,2);SCNDAT%(CT%,1);"D";
0B90   0494            PRINT #1,SCNDAT%(CT%,4);SCNDAT%(CT%,1);
0BCC   0494            PRINT #1,SCNDAT%(CT%,4);SCNDAT%(CT%,3);
0C08   0494            PRINT #1,SCNDAT%(CT%,2);SCNDAT%(CT%,3);
0C44   0494            PRINT #1,SCNDAT%(CT%,2);SCNDAT%(CT%,1);"U";
0CB6   0494            RETURN
0CBA   0494
0CBA   0494   PCIRCL:
0CBF   0494            RADIUS% = SQR((SCNDAT%(CT%,3)-SCNDAT%(CT%,1))^2 + (SCNDAT%(CT%,4)-SCNDAT%(CT%,2))^2)
0D1A   0496            PRINT #1,"CC ";SCNDAT%(CT%,2);SCNDAT%(CT%,1);RADIUS%;
0D63   0496            RETURN
0D67   0496
0D67   0496   PSRECT:
0D6C   0496            SX% = SCNDAT%(CT%,4):EX% = SCNDAT%(CT%,2)
0DA0   049A            SY% = SCNDAT%(CT%,3):EY% = SCNDAT%(CT%,1)
0DD4   049E            IF EX% <= SX% THEN SX% = SCNDAT%(CT%,2):EX% = SCNDAT%(CT%,4)
0E15   049E            IF EY% <= SY% THEN SY% = SCNDAT%(CT%,1):EY% = SCNDAT%(CT%,3)
0E56   049E
0E56   049E            PRINT #1,SX%;SY%;"D";
0E74   049E
0E74   049E            IF EX% - SX% >= EY% - SY% THEN GOSUB STEPY ELSE GOSUB STEPX
0E9D   049E
0E9D   049E            PRINT #1,"U";
0EAD   049E            RETURN
0EB1   049E
0EB1   049E   STEPY:
0EB6   049E            PRINT #1,EX%;SY%;
0ECE   049E            SY% = SY% + 1
0ED7   049E            IF SY% > EY% THEN RETURN
0EE8   049E            PRINT #1,EX%;SY%;SX%;SY%;
0F0E   049E            SY% = SY% + 1
0F17   049E            IF SY% > EY% THEN RETURN
0F28   049E            PRINT #1,SX%;SY%;
0F40   049E            GOTO STEPY
0F44   049E
0F44   049E   STEPX:
0F49   049E            PRINT #1,SX%;EY%;
0F61   049E            SX% = SX% + 1
0F6A   049E            IF SX% > EX% THEN RETURN
0F7B   049E            PRINT #1,SX%;EY%;SX%;SY%;
0FA1   049E            SX% = SX% + 1
0FAA   049E            IF SX% > EX% THEN RETURN
0FBB   049E            PRINT #1,SX%;SY%;
0FD3   049E            GOTO STEPX
0FD7   049E
0FD7   049E   NEWMENU: 'write old item in yellow, point to and highlight new item
0FDC   049E            COLOR 14,0:GOSUB DISPMENU
0FEE   049E            MENU% = MENU% + DIFF%
0FFA   049E            IF MENU% = 10 THEN MENU% = 9
```

```
100C  049E          IF MENU% = 11 THEN MENU% = 9
101E  049E          IF MENU% > 15 THEN MENU% = 15
1030  049E          COLOR 0,7:GOSUB DISPMENU:RETURN
1046  049E
1046  049E  INITIALIZE:
104B  049E          'change to screen 0 and display messages
104B  049E          SCREEN 0,0,1,1:COLOR 7,0:CLS:LOCATE 10,17:PRINT "Loading selected Reagent and Pattern Data Files";
108F  049E          LOCATE 12,33:PRINT "Please Wait..."
10A9  049E
10A9  049E          'initialize notepad on screen 2
10A9  049E          SCREEN 0,0,2,1:CLS:COLOR 15
10CE  049E          PRINT"Digital Notepad - - -All information typed here is sent to the printer"
10DB  049E          NOTELINE% = 3
10E2  049E
10E2  049E          'initialize menu arrays
10E2  049E          RESTORE ARRDATA
10E9  049E          FOR I%=0 TO 17
10EF  049E                  READ MENU$(I%,0),MENU$(I%,1):
111F  049E                  READ MENU(I%,1),MENU(I%,2),MENU(I%,3),MENU(I%,4)
1180  049E          NEXT I%
1193  049E
1193  049E          'get default reagent file and read values
1193  049E
1193  049E          OPEN "READEF.RJP" FOR INPUT AS #1
11A4  049E          INPUT #1,FILE$
11B6  04A2          INPUT #1,REANAME$
11C8  04A6          CLOSE #1
11CF  04A6
11CF  04A6          OPEN FILE$ FOR INPUT AS #1:       'get reagent data
11E0  04A6          INPUT #1,MENU(0,0):               'frequency
1200  04A6          INPUT #1,MENU(1,0):               'amplitude
1223  04A6          INPUT #1,MENU(2,0):               'strobe delay
1246  04A6          INPUT #1,MENU(3,0):               'pulse width
1269  04A6          INPUT #1,MENU(4,0):               'rise time
128C  04A6          INPUT #1,MENU(5,0):               'fall time
12B1  04A6          CLOSE #1
12B8  04A6
12B8  04A6          'get default pattern file and read values
12B8  04A6
12B8  04A6          OPEN "PATDEF.RJP" FOR INPUT AS #1
12C9  04A6          INPUT #1,FILE$
12DB  04A6          INPUT #1,PATNAME$
12ED  04AA          CLOSE #1
12F4  04AA
12F4  04AA          OPEN FILE$ FOR INPUT AS #1:       'get pattern data
1305  04AA          INPUT #1,ELNUM%
1317  04AA          INPUT #1,MENU(6,0):               'grid
133A  04AA          INPUT #1,MENU(7,0):               'repeat count
135D  04AA          INPUT #1,MENU(8,0):               'x offset
1380  04AA          INPUT #1,MENU(9,0):               'y offset
13A3  04AA          FOR I% = 0 TO ELNUM%-1
13B1  04AC                  FOR J% = 0 TO 5
13B7  04AC                          INPUT #1,SCNDAT%(I%,J%)
13DB  04AC                  NEXT J%
13EB  04AC          NEXT I%
13FD  04AC          CLOSE #1
1404  04AC
1404  04AC          'set remaining parameters in menu array
1404  04AC
1404  04AC          MENU(12,0) = 1:                   'row 1
1420  04AC          MENU(13,0) = 1:                   'column 1
143C  04AC          MENU(14,0) = 0:                   'row spacing
1458  04AC          MENU(15,0) = 0:                   'column spacing
1474  04AC
1474  04AC          'change active displayed screen to screen 0 to draw and display parameters
1474  04AC
1474  04AC          SCREEN 0,0,0,1:CLS
1491  04AC
1491  04AC          COLOR 13:LOCATE 1,32:PRINT "REAGENT PRINTING";
```

```
14B2    04AC            COLOR 9
14B9    04AC            FOR I=2 TO 79
14C3    04AC                    LOCATE 3,I:PRINT CHR$(196);:LOCATE 5,I:PRINT CHR$(205);:LOCATE 18,I:PRINT CHR$(196);
1523    04B0            NEXT I
153E    04B0            FOR I=4 TO 17
1548    04B0                    LOCATE I,1:PRINT CHR$(179);:LOCATE I,28:PRINT CHR$(186);:LOCATE I,54:PRINT CHR$(186);:LOCATE I,80:P
                RINT CHR$(179);
15C8    04B0            NEXT I
15E6    04B0            RESTORE TABLE
15ED    04B0            FOR I=1 TO 12
15F7    04B0                    READ R%,C%,N%:LOCATE R%,C%:PRINT CHR$(N%);
162A    04B6            NEXT I
1645    04B6
1645    04B6            'display 16 menu choices in yellow
1645    04B6
1645    04B6            COLOR 14,0
1651    04B6            FOR MENU% = 0 TO 15
1657    04B6                    GOSUB DISPMENU
165D    04B6            NEXT MENU%
166D    04B6
166D    04B6            'set for first menu entry and highlight it
166D    04B6            MENU% = 0:COLOR 0,7
1680    04B6            GOSUB DISPMENU
1686    04B6
1686    04B6            'print three headings and instructions
1686    04B6            COLOR 10,0
1692    04B6            LOCATE 4,14.5-LEN(REANAME$)/2:PRINT REANAME$;
16C1    04B6            LOCATE 4,41-LEN(PATNAME$)/2:PRINT PATNAME$;
16F0    04B6            LOCATE 4,60:PRINT "PRINT LOCATION";
170A    04B6
170A    04B6            COLOR 7:LOCATE 19,20:PRINT "Use ";:COLOR 15:PRINT CHR$(27);CHR$(32);CHR$(26);
1754    04B6            PRINT CHR$(32);CHR$(24);CHR$(32);CHR$(25);:COLOR 7:PRINT " to position highlighted cursor";
1793    04B6            LOCATE 20,18:PRINT "Use ";:COLOR 15:PRINT "+";:COLOR 7:PRINT " or ";:COLOR 15:PRINT "-";
17E9    04B6            COLOR 7:PRINT" to scroll current value up or down";
17FD    04B6            LOCATE 21,6:PRINT "Use ";:COLOR 15:PRINT "P";:COLOR 7:PRINT " to print pattern or ";
183F    04B6            COLOR 15:PRINT "E";:COLOR 7:PRINT " to exit to print menu";
1867    04B6            PRINT " or ";:COLOR 15:PRINT "S";:COLOR 7:PRINT " to use notepad";
189C    04B6
189C    04B6            'set screen to view menu just created and exit
189C    04B6
189C    04B6            SCREEN 0,0,0,0
18B1    04B6            RETURN
18B5    04B6
18B5    04B6    DISPMENU:
18BA    04B6            IF MENU% = 10 OR MENU% = 11 THEN RETURN
18DE    04B6            LOCATE (MENU% MOD 6)*2+7,(INT(MENU%/6)*28+2)-2*INT(MENU%/12)
193B    04B6            PRINT MENU$(MENU%,0)
195E    04B6            LOCATE (MENU% MOD 6)*2+7,MENU(MENU%,4)
19BB    04B6            PRINT USING MENU$(MENU%,1);MENU(MENU%,0);
19B6    04B6            RETURN
19BF    04B6    REM $PAGE
19BF    04B6    '************ DATA USED BY THIS MODULE ************
19BF    04B6
19BF    04B6    ARRDATA:
19C4    04B6            DATA "Dot Frequency        Hz","##,###",10000,1,1,16
19C6    04B6            DATA "Amplitude            V ","###",150,0,1,19
19C8    04B6            DATA "Strobe Delay         uS","##,###.#",15999.5,.5,.5,16
19CA    04B6            DATA "Pulse Width          ","###",999,0,1,19
19CC    04B6            DATA "Rise Time            ","###",999,0,1,19
19CE    04B6            DATA "Fall Time            ","###",999,0,1,19
19D0    04B6            DATA "Grid Size          in","#.###",.005,.005,.005,45
19D2    04B6            DATA "Repeat Count         ","##",99,0,1,47
19D4    04B6            DATA "X Axis Offset      in","#.###",2,0,.005,45
19D6    04B6            DATA "Y Axis Offset      in","#.###",2,0,.005,45
19D8    04B6            DATA "","",0,0,0,0
19DA    04B6            DATA "","",0,0,0,0
19DC    04B6            DATA "Row to Print         ","##",99,1,1,74
19DE    04B6            DATA "Column to Print      ","##",99,1,1,74
19E0    04B6            DATA "Row Spacing        in","#.###",3,0,.005,72
```

| | | | |
|---|---|---|---|
| 19E2 | 04B6 | DATA "Column Spacing | in","#.###",3,0,.005,72 |
| 19E4 | 04B6 | DATA "","",0,0,0,0 | |
| 19E6 | 04B6 | DATA "","",0,0,0,0 | |
| 19E8 | 04B6 | | |
| 19E8 | 04B6 | TABLE: | |
| 19ED | 04B6 | DATA 3,1,218 | |
| 19EF | 04B6 | DATA 3,28,210 | |
| 19F1 | 04B6 | DATA 3,54,210 | |
| 19F3 | 04B6 | DATA 3,80,191 | |
| 19F5 | 04B6 | DATA 5,1,198 | |
| 19F7 | 04B6 | DATA 5,28,206 | |
| 19F9 | 04B6 | DATA 5,54,206 | |
| 19FB | 04B6 | DATA 5,80,181 | |
| 19FD | 04B6 | DATA 18,1,192 | |
| 19FF | 04B6 | DATA 18,28,208 | |
| 1A01 | 04B6 | DATA 18,54,208 | |
| 1A03 | 04B6 | DATA 18,80,217 | |
| 1A05 | 04B6 | | |
| 1A05 | 04B6 | END SUB | |
| 1A0C | 04B6 | | |
| 1A0C | 04B6 | | |
| 2069 | 04B6 | | |

50426 Bytes Available
44716 Bytes Free

0 Warning Error(s)
   0 Severe Error(s)

Reagent Jet Printer
Reagent Filing

Offset  Data    Source Line       IBM Personal Computer BASIC Compiler V2.00

```
0030   0006   REM $TITLE:'Reagent Jet Printer' $SUBTITLE:'Reagent Filing'
0030   0006   'MODULE   - "REAFILE" File Handling for reagents
0030   0006   '
0030   0006   'AUTHOR   - N. A. Enevold
0030   0006   '
0030   0006   'COPYRIGHT (C) 1985 ABBOTT LABORATORIES
0030   0006   '
0030   0006   'REVISION - 1.1 03-07-86 NAE Added notes and description
0030   0006   '           1.0 02-14-86 NAE Creation of initial code
0030   0006   '
0030   0006   'SYSTEM   - This code can only be compiled by the BASCOM
0030   0006   '           COMPILER, it will not run under the INTERPRETER!!
0030   0006   '
0030   0006   'DESCRIPTION:
0030   0006   '     This module allow file handling for reagents. When invoked, it displays
0030   0006   '     the current contents of the reagent directory in 4 columns of 20 entries
0030   0006   '     each. The reagent which is currently selected for printing is marked by
0030   0006   '     an asterisk to the left of the reagent name. After the directory is listed
0030   0006   '     the user is presented with 5 menu choices. The left and right arrows are
0030   0006   '     used to highlight menu items and the enter key is used to invoke action.
0030   0006   '     The menu choices and their actions are:
```

```
0030   0006   '
0030   0006   '              DELETE - Remove a reagent file from the directo
ry
0030   0006   '              COPY -   Copy a reagent file to a new reagent n
ame, saving the old reagent
0030   0006   '              RENAME - Change the name of the reagent without
changing the reagent itself
0030   0006   '              SELECT - Selct a reagent for printing
0030   0006   '              EXIT -   Return to the main menu
0030   0006   '
0030   0006   'DATA DICTIONARY
0030   0006   '      TYPE%     Which type of valid key was pushed
0030   0006   '      MENU%     Which menu item is being pointer to (0-4)
0030   0006   '      DIFF%     Distance to move MENU% at left or right arro
w
0030   0006   '      FLAG%     Error type 0-4
0030   0006   '      POINTER%  Position of REANAME$ in directory list
0030   0006   '      REANUM%           Number of reagent names in directory
list
0030   0006   '      TEMP%     Storage for integers during reagent copy
0030   0006   '      A$        Misc. input string
0030   0006   '      FUNCT$    Printed at bottom of screen during prompt fo
r reagent name
0030   0006   '      REANAME$  Reagent name currently being worked on
0030   0006   '      SELNAME$  Reagent name currently selected for printing
0030   0006   '      FILE$     Filename of reagent data file
0030   0006   '      SFILE$    Filename for source reagent data file used d
uring copy
0030   0006   '      DFILE$    Filename for destination reagent data file u
sed during copy
0030   0006   '      NEWNAME$  New reagent name for COPY and RENAME
0030   0006   '      TEMP$     Reagent names are held here as the directory
is being re-written
0030   0006   '      NEWFILE$  Destination filename used while copying reag
ent data files
0030   0006   '      MESSAGE$  A message printed at the bottom of the scree
n
0030   0006   '      MENU$(4,1) Array of strings containing the short and lo
ng menu names
0030   0006   '      ERRMSG$   Message printed when any error occurs
0030   0006   '      ERR$      Appended to ERRMSG$ to indicate nature of er
ror
0030   0006   REM $PAGE
0030   0006   SUB REAGENT.FILE STATIC
0047   0006
0047   0006        GOSUB INITIALIZE
004D   0006        TYPE% = 0
0054   0008
0054   0008        WHILE TYPE% <> 3
005F   0008              A$ = ""
0069   000C              WHILE A$ = ""
0078   000C                    A$ = INKEY$
0082   000C              WEND
0085   000C              IF A$ = CHR$(0) + CHR$(75) THEN TYPE% = 1:
       'left arrow
00AA   000C              IF A$ = CHR$(0) + CHR$(77) THEN TYPE% = 2:
       'right arrow
```

```
00CF    000C                    IF A$ = CHR$(13) THEN TYPE% = 3:
            '<cr> to execute selection
00E9    000C
00E9    000C                    ON TYPE% GOSUB T1, T2, T3
00F8    000C            WEND
00FC    000C
00FC    000C            EXIT SUB
0100    000C
0100    000C    REM $PAGE
0100    000C    '******** SUB-ROUTINES FOR THIS MODULE ********
0100    000C
0100    000C    T1:             'left arrow
0105    000C            TYPE% = 0
010C    000C            IF MENU% = 0 THEN RETURN
011B    000E            DIFF% = -1
0122    0010            GOSUB NEW.MENU
0128    0010            RETURN
012C    0010
012C    0010    T2:             'right arrow
0131    0010            TYPE% = 0
0138    0010            IF MENU% = 4 THEN RETURN
0147    0010            DIFF% = 1
014E    0010            GOSUB NEW.MENU
0154    0010            RETURN
0158    0010
0158    0010    T3:             '<cr> (execute selected menu item)
015D    0010            LOCATE 25,1:PRINT SPACE$(79);
017A    0010            ON MENU% + 1 GOSUB T3A, T3B, T3C, T3D, T3E
018F    0010            GOSUB MENU.ON
0195    0010            RETURN
0199    0010
0199    0010    REM $PAGE
0199    0010    T3A:            'delete reagent
019E    0010            TYPE% = 0
01A5    0010            FUNCT$ = "Delete"
01AF    0014            GOSUB GET.SOURCE
01B5    0014            IF LEN(REANAME$) = 0 THEN RETURN
01C7    0018            IF REANAME$ = SELNAME$ THEN FLAG% = 4:GOSUB SHOW.ERROR:
            RETURN
01E7    001E            GOSUB SEARCH
01ED    001E            IF POINTER% = 0 THEN FLAG% = 1:GOSUB SHOW.ERROR:RETURN
0209    0020
0209    0020            MESSAGE$ = "Deleting " + REANAME$ + "    Please Wait..
            ."
0220    0024            GOSUB MESSAGE.ON
0226    0024
0226    0024                    'rewrite directory deleting REANAME$ as indicat
            ed by POINTER%
0226    0024            KILL "READIR.OLD"
022D    0024            NAME "READIR.RJP" AS "READIR.OLD"
0237    0024            OPEN "READIR.OLD" FOR INPUT AS #1
0248    0024            OPEN "READIR.RJP" FOR OUTPUT AS #2
025A    0024
025A    0024            INPUT #1, REANUM%
026C    0026            REANUM% = REANUM% - 1
0275    0026            WRITE #2,REANUM%
0286    0026
```

```
0286  0026            IF REANUM% = 0 THEN GOTO DIR.DONE
0295  0026            FOR I% = 1 TO REANUM% + 1
02A4  0028                  INPUT #1,REANAME$
02B6  0028                  IF I% <> POINTER% THEN PRINT #2,REANAME$
02D3  002A            NEXT I%
02E5  002A
02E5  002A  DIR.DONE:
02EA  002A            CLOSE #1:CLOSE #2
02FB  002A
02FB  002A                  'remove data file
02FB  002A            FILE$ = RIGHT$(STR$(POINTER%),LEN(STR$(POINTER%))-1) +
              "REA.RJP"
031C  002E            KILL FILE$
0323  002E
0323  002E                  'rename remaining data files to maintain linked
              list to directory
0323  002E            WHILE (REANUM% + 1) > POINTER%
0333  002E                  SFILE$ = RIGHT$(STR$(POINTER%+1),LEN(STR$(POINT
              ER%+1))-1) + "REA.RJP"
0359  0032                  DFILE$ = RIGHT$(STR$(POINTER%),LEN(STR$(POINTER
              %))-1) + "REA.RJP"
037D  0036                  NAME SFILE$ AS DFILE$
0387  0036                  POINTER% = POINTER% + 1
0390  0036            WEND
0393  0036
0393  0036            GOSUB MESSAGE.OFF
0399  0036            REANAME$ = SELNAME$
03A3  0036            GOSUB T3DA
03A9  0036            GOSUB DISP.DIR
03AF  0036            RETURN
03B3  0036
03B3  0036  REM $PAGE
03B3  0036  T3B:      'copy reagent
03B8  0036            TYPE% = 0
03BF  0036            IF REANUM% = 60 THEN FLAG% = 3:GOSUB SHOW.ERROR:RETURN
03DB  0036            FUNCT$ = "Copy"
03E5  0036            GOSUB GET.SOURCE
03EB  0036            IF LEN(REANAME$) = 0 THEN RETURN
03FD  0036            GOSUB SEARCH
0403  0036            IF POINTER% = 0 THEN FLAG% = 1:GOSUB SHOW.ERROR:RETURN
041F  0036
041F  0036            GOSUB GET.NEW.NAME
0425  0036            IF LEN(NEWNAME$) = 0 THEN RETURN
0437  003A            IF LEN(NEWNAME$) > 15 THEN FLAG% = 2:GOSUB SHOW.ERROR:R
              ETURN
0457  003A
0457  003A            MESSAGE$ = "Copying " + REANAME$ + " to " + NEWNAME$ +
              "   Please wait.."
047C  003A            GOSUB MESSAGE.ON
0482  003A
0482  003A                  'add new name at end of directory
0482  003A            KILL "READIR.OLD"
0489  003A            NAME "READIR.RJP" AS "READIR.OLD"
0493  003A            OPEN "READIR.OLD" FOR INPUT AS #1
04A4  003A            OPEN "READIR.RJP" FOR OUTPUT AS #2
04B6  003A
04B6  003A            INPUT #1, REANUM%
```

```
04C8   003A           REANUM% = REANUM% + 1
04D1   003A           WRITE #2,REANUM%
04E2   003A
04E2   003A           FOR I% = 1 TO REANUM% - 1
04F1   003C                   INPUT #1,TEMP$
0503   0040                   PRINT #2,TEMP$
0513   0040           NEXT I%
0525   0040           PRINT #2,NEWNAME$
0535   0040
0535   0040           CLOSE #1:CLOSE #2
0543   0040
0543   0040                   'create copy of data file
0543   0040           FILE$ = RIGHT$(STR$(POINTER%),LEN(STR$(POINTER%))-1) +
               "REA.RJP"
0567   0040           NEWFILE$ = RIGHT$(STR$(REANUM%),LEN(STR$(REANUM%))-1) +
               "REA.RJP"
058B   0044
058B   0044           OPEN FILE$ FOR INPUT AS #1
059C   0044           OPEN NEWFILE$ FOR OUTPUT AS #2
05AE   0044
05AE   0044           INPUT #1,TEMP
05C0   0048           WRITE #2,TEMP:     'frequency
05D0   0048           INPUT #1,TEMP
05E2   0048           WRITE #2,TEMP:     'pulse width
05F2   0048           INPUT #1,TEMP
0604   0048           WRITE #2,TEMP:     'strobe delay
0614   0048           INPUT #1,TEMP
0626   0048           WRITE #2,TEMP:     'nozzle
0636   0048
0636   0048           INPUT #1,TEMP$
0648   0048           PRINT #2,TEMP$:              'concentration
0658   0048           INPUT #1,TEMP$
066A   0048           PRINT #2,TEMP$:              'density
067A   0048           INPUT #1,TEMP$
068C   0048           PRINT #2,TEMP$:              'viscosity
069C   0048
069C   0048           CLOSE #1:CLOSE #2
06AA   0048
06AA   0048           GOSUB MESSAGE.OFF
06B0   0048           GOSUB DISP.DIR
06B6   0048           RETURN
06BA   0048
06BA   0048   REM $PAGE
06BA   0048   T3C:    'rename reagent
06BF   0048           TYPE% = 0
06C6   0048           FUNCT$ = "Rename"
06D0   0048           GOSUB GET.SOURCE
06D6   0048           IF LEN(REANAME$) = 0 THEN RETURN
06E8   0048           GOSUB SEARCH
06EE   0048           IF POINTER% = 0 THEN FLAG% = 1:GOSUB SHOW.ERROR:RETURN
070A   0048
070A   0048           GOSUB GET.NEW.NAME
0710   0048           IF LEN(NEWNAME$) = 0 THEN RETURN
0722   0048           IF LEN(NEWNAME$) > 15 THEN FLAG% = 2:GOSUB SHOW.ERROR:R
               ETURN
0742   0048           IF NEWNAME$ = REANAME$ THEN RETURN
0755   0048           MESSAGE$ = "Renaming " + REANAME$ + " to " + NEWNAME$ +
```

```
077A    004B            " Please wait.."
                        GOSUB MESSAGE.ON
0780    004B
0780    004B                    'renaming reagent name in directory
0780    004B            KILL "READIR.OLD"
0787    004B            NAME "READIR.RJP" AS "READIR.OLD"
0791    004B            OPEN "READIR.OLD" FOR INPUT AS #1
07A2    004B            OPEN "READIR.RJP" FOR OUTPUT AS #2
07B4    004B
07B4    004B            INPUT #1, REANUM%
07C6    004B            WRITE #2,REANUM%
07D7    004B
07D7    004B            FOR I% = 1 TO REANUM%
07E4    004A                    INPUT #1,TEMP$
07F6    004A                    IF I% <> POINTER% THEN PRINT #2,TEMP$
0813    004A                    IF I% = POINTER% THEN PRINT #2,NEWNAME$
0830    004A            NEXT I%
0842    004A
0842    004A            CLOSE #1:CLOSE #2
0850    004A
0850    004A            GOSUB MESSAGE.OFF
0856    004A            IF REANAME$ = SELNAME$ THEN REANAME$ = NEWNAME$:GOSUB T
                3DA
0875    004A            GOSUB DISP.DIR
087B    004A            RETURN
087F    004A
087F    004A    REM $PAGE
087F    004A    T3D:    'select reagent for printing
0884    004A            TYPE% = 0
088B    004A            FUNCT$ = "Select"
0895    004A            GOSUB GET.SOURCE
089B    004A            IF LEN(REANAME$) = 0 THEN RETURN
08AD    004A            IF REANAME$ = SELNAME$ THEN RETURN
08C0    004A            GOSUB T3DA
08C6    004A            GOSUB DISP.DIR
08CC    004A            RETURN
08D0    004A
08D0    004A    T3DA:
08D5    004A            GOSUB SEARCH
08DB    004A            IF POINTER% = 0 THEN FLAG% = 1:GOSUB SHOW.ERROR:RETURN
08F7    004A
08F7    004A            MESSAGE$ = "Selecting " + REANAME$ + "     Please Wait.
                .."
090E    004A            GOSUB MESSAGE.ON
0914    004A
0914    004A                    'change entrys in reagent default file READEF.R
                JP
0914    004A            OPEN "READEF.RJP" FOR OUTPUT AS #1
0926    004A            FILE$ = RIGHT$(STR$(POINTER%),LEN(STR$(POINTER%))-1) +
                "REA.RJP"
094A    004A
094A    004A            PRINT #1,FILE$
095A    004A            PRINT #1,REANAME$
096A    004A
096A    004A            CLOSE #1
0971    004A            GOSUB MESSAGE.OFF
0977    004A            RETURN
```

```
097B    004A
097E    004A    T3E:    'exit reagent filing
0980    004A            RETURN
0984    004A
0984    004A    REM $PAGE
0984    004A    SEARCH:
0989    004A            POINTER% = 0
0990    004A            OPEN "READIR.RJP" FOR INPUT AS #1
09A1    004A            INPUT #1,REANUM%:'      get number of reagents in directory
09B3    004A            IF REANUM% = 0 THEN CLOSE #1:RETURN
09C9    004A            TEMP$ = ""
09D3    004A            WHILE (POINTER% < REANUM%) AND (REANAME$ <> TEMP$)
09FB    004A                    LINE INPUT #1,TEMP$
0A08    004A                    POINTER% = POINTER% + 1
0A11    004A            WEND
0A14    004A            IF REANAME$ <> TEMP$ THEN POINTER% = 0
0A2A    004A            CLOSE #1
0A31    004A            RETURN
0A35    004A
0A35    004A    GET.SOURCE:
0A3A    004A            LOCATE 25,1:COLOR 15,0:PRINT "Enter Reagent Name to "FUNCT$" ";
0A6C    004A            LINE INPUT;"",REANAME$
0A7A    004A            LOCATE 25,1:PRINT SPACE$(79);
0A97    004A            RETURN
0A9B    004A
0A9B    004A    GET.NEW.NAME:
0AA0    004A            LOCATE 25,1:COLOR 15,0:PRINT "Enter New Reagent Name ";
0AC6    004A            LINE INPUT;"",NEWNAME$
0AD4    004A            LOCATE 25,1:PRINT SPACE$(79);
0AF1    004A            RETURN
0AF5    004A
0AF5    004A    DISP.DIR:       'display reagent directory in 4 columns of 20 rows
0AFA    004A                    'read selected reagent into SELNAME$
0AFA    004A            OPEN "READEF.RJP" FOR INPUT AS #1
0B0B    004A            INPUT #1,SELNAME$:      'read and discard data file name
0B1D    004A            INPUT #1,SELNAME$:      'read and save reagent name
0B2F    004A            CLOSE #1
0B36    004A
0B36    004A            OPEN "READIR.RJP" FOR INPUT AS #1
0B47    004A            INPUT #1,REANUM%:'      read number of reagents
0B59    004A            MESSAGE$ = "Reading Reagent Directory   Please Wait"
0B63    004A            GOSUB MESSAGE.ON
0B69    004A            FLAG% = 0
0B70    004A            TEMP% = REANUM% - 1:IF REANUM% < 80 THEN TEMP% = REANUM%
0B8B    004C            FOR I% = 0 TO TEMP%
0B97    004E                    LOCATE (I% MOD 20)+1,(INT(I%/20)*20)+1
0BCA    004E                    PRINT SPACE$(18);
0BDA    004E            NEXT I%
0BEC    004E
0BEC    004E            FOR I% = 0 TO REANUM% - 1
0BFA    0050                    INPUT #1,REANAME$
0C0C    0050                    LOCATE (I% MOD 20)+1,(INT(I%/20)*20)+3
```

```
0C3F  0050                PRINT REANAME$;
0C4C  0050                IF REANAME$ = SELNAME$ THEN LOCATE (I% MOD 20)+
               1,(INT(I%/20)*20)+1:PRINT "*";
0C9B  0050            NEXT I%
0CB0  0050            CLOSE #1
0CB7  0050            GOSUB MESSAGE.OFF
0CBD  0050            RETURN
0CC1  0050
0CC1  0050    INITIALIZE:
0CC6  0050            DIM MENU$(4,1)
0CC7  0078            MENU$(0,0) = "Delete"
0CDF  0078            MENU$(0,1) = "Remove a reagent file from the directory"
0CFA  0078            MENU$(1,0) = "Copy"
0D15  0078            MENU$(1,1) = "Copy a reagent file to a new reagent name
               "
0D2E  0078            MENU$(2,0) = "Rename"
0D4B  0078            MENU$(2,1) = "Rename a reagent file in the directory"
0D69  0078            MENU$(3,0) = "Select"
0D84  0078            MENU$(3,1) = "Select a reagent file to be printed"
0DA0  0078            MENU$(4,0) = "Exit"
0DBB  0078            MENU$(4,1) = "Return to the main menu"
0DD7  0078
0DD7  0078            COLOR 9,0:CLS
0DEA  0078            LOCATE 21,1
0DF7  0078            FOR I% = 1 TO 80
0DFE  0078                PRINT "D";
0E0B  0078            NEXT I%
0E1B  0078
0E1B  0078            FOR MENU% = 0 TO 4
0E21  0078                GOSUB MENU.OFF
0E27  0078            NEXT MENU%
0E37  0078
0E37  0078            GOSUB DISP.DIR
0E3D  0078            IF FLAG% > 0 THEN GOSUB SHOW.ERROR
0E4E  0078            MENU% = 4
0E55  0078            GOSUB MENU.ON
0E5B  0078
0E5B  0078            RETURN
0E5F  0078
0E5F  0078    NEW.MENU:
0E64  0078            GOSUB MENU.OFF
0E6A  0078            MENU% = MENU% + DIFF%
0E76  0078            GOSUB MENU.ON
0E7C  0078            RETURN
0E80  0078
0E80  0078    MENU.ON:
0E85  0078            LOCATE 22,(MENU%*10)+18
0E9C  0078            COLOR 0,7
0EA8  0078            PRINT MENU$(MENU%,0);
0EC6  0078            LOCATE 25,40-LEN(MENU$(MENU%,1))/2
0EFA  0078            COLOR 7,0
0F06  0078            PRINT MENU$(MENU%,1);
0F25  0078            RETURN
0F29  0078
0F29  0078    MENU.OFF:
0F2E  0078            LOCATE 22,(MENU%*10)+18
```

```
0F45   0078            COLOR 14,0
0F51   0078            PRINT MENU$(MENU%,0);
0F6F   0078            LOCATE 25,40-LEN(MENU$(MENU%,1))/2
0FA3   0078            PRINT SPACE$(LEN(MENU$(MENU%,1)));
0FC8   0078            RETURN
0FCC   0078
0FCC   0078   SHOW.ERROR:
0FD1   0078            ON FLAG% GOSUB ER1, ER2, ER3, ER4
0FE2   0078            ERRMSG$ = ERR$ + "    Strike any key.."
0FF2   0080            LOCATE 24,40-LEN(ERRMSG$)/2
1014   0080            COLOR 13,0
1020   0080            PRINT ERRMSG$;
102D   0080            A$ = ""
1037   0080            WHILE A$ = ""
1046   0080                    A$ = INKEY$
1050   0080            WEND
1053   0080            GOSUB MESSAGE.OFF
1059   0080            RETURN
105D   0080
105D   0080   ER1:
1062   0080            ERR$ = REANAME$ + " Not Found in the Directory"
1072   0080            RETURN
1076   0080
1076   0080   ER2:
107B   0080            ERR$ = "Reagent Name is too Long (15 characters max.)"
1085   0080            RETURN
1089   0080
1089   0080   ER3:
108E   0080            ERR$ = "Directory is Full (80 reagents max.)"
1098   0080            RETURN
109C   0080
109C   0080   ER4:
10A1   0080            ERR$ = "Cannot Modify SELECTd reagent Name"
10AB   0080            RETURN
10AF   0080
10AF   0080   MESSAGE.ON:
10B4   0080            LOCATE 24,38 - LEN(MESSAGE$) / 2:COLOR 11,0:PRINT MESSA
               GE$;
10EF   0080            RETURN
10F3   0080
10F3   0080
10F3   0080   MESSAGE.OFF:
10FB   0080            LOCATE 24,1:COLOR 15,0:PRINT SPACE$(79);
1121   0080            RETURN
1125   0080
1125   0080   END SUB
112C   0080
16C9   0080

50426 Bytes Available
45718 Bytes Free

0 Warning Error(s)
    0 Severe  Error(s)
```

Reagent Jet Printer
Pattern Filing

| Offset | Data | Source Line | IBM Personal Computer BASIC Compiler V2.00 |
|---|---|---|---|
| 0030 | 0006 | REM $TITLE:'Reagent Jet Printer' $SUBTITLE:'Pattern Filing' | |
| 0030 | 0006 | 'MODULE   - "PATFILE" File Handling for patterns | |
| 0030 | 0006 | ' | |
| 0030 | 0006 | 'AUTHOR   - N. A. Enevold | |
| 0030 | 0006 | ' | |
| 0030 | 0006 | 'COPYRIGHT (C) 1985 ABBOTT LABORATORIES | |
| 0030 | 0006 | ' | |
| 0030 | 0006 | 'REVISION - 1.0 02-12-86 NAE Creation of initial code | |
| 0030 | 0006 | ' | |
| 0030 | 0006 | 'SYSTEM   - This code can only be compiled by the BASCOM | |
| 0030 | 0006 | '            COMPILER, it will not run under the INTERPRETER!! | |
| 0030 | 0006 | ' | |
| 0030 | 0006 | 'DESCRIPTION: | |
| 0030 | 0006 | '      This module allow file handling for patterns.  When invoked, it displays | |
| 0030 | 0006 | '      the current contents of the pattern directory in 4 columns of 20 entries | |
| 0030 | 0006 | '      each. The pattern which is currently selected for printing is marked by | |
| 0030 | 0006 | '      an asterisk to the left of the pattern name. After the directory is listed | |
| 0030 | 0006 | '      the user is presented with 5 menu choices.  The left and right arrows are | |
| 0030 | 0006 | '      used to highlight menu items and the enter key is used to invoke action. | |
| 0030 | 0006 | '      The menu choices and their actions are: | |
| 0030 | 0006 | ' | |
| 0030 | 0006 | '            DELETE - Remove a pattern file from the directory | |
| 0030 | 0006 | '            COPY -   Copy a pattern file to a new pattern name, saving the old pattern | |
| 0030 | 0006 | '            RENAME - Change the name of the pattern without changing the pattern itself | |
| 0030 | 0006 | '            SELECT - Selct a pattern for printing | |
| 0030 | 0006 | '            EXIT -   Return to the main menu | |
| 0030 | 0006 | ' | |
| 0030 | 0006 | 'DATA DICTIONARY | |
| 0030 | 0006 | '     TYPE%      Which type of valid key was pushed | |
| 0030 | 0006 | '     MENU%      Which menu item is being pointer to (0-4) | |
| 0030 | 0006 | '     DIFF%      Distance to move MENU% at left or right arrow | |
| 0030 | 0006 | '     FLAG%      Error type 0-4 | |
| 0030 | 0006 | '     POINTER%   Position of PATNAME$ in directory list | |
| 0030 | 0006 | '     PATNUM%            Number of pattern names in directory list | |
| 0030 | 0006 | '     ELNUM%     Number of elements in a pattern file | |
| 0030 | 0006 | '     TEMP%      Storage for integers during pattern copy | |
| 0030 | 0006 | '     I%         Counter used during pattern copy | |
| 0030 | 0006 | '     J%         Counter used during pattern copy | |
| 0030 | 0006 | '     A$         Misc. input string | |
| 0030 | 0006 | '     FUNCT$     Printed at bottom of screen during prompt for pattern name | |

```
0030  0006           PATNAME$   Pattern name currently being worked on
0030  0006           SELNAME$   Pattern name currently selected for printing
0030  0006           FILE$      Filename of pattern data file
0030  0006           SFILE$     Filename for source pattern data file used d
                  uring copy
0030  0006           DFILE$     Filename for destination pattern data file u
                  sed during copy
0030  0006           NEWNAME$   New pattern name for COPY and RENAME
0030  0006           TEMP$      Pattern names are held here as the directory
                   is being re-written
0030  0006           NEWFILE$   Destination filename used while copying patt
                  ern data files
0030  0006           MESSAGE$   A message printed at the bottom of the scree
                  n
0030  0006           MENU$(4,1) Array of strings containing the short and lo
                  ng menu names
0030  0006           ERRMSG$    Message printed when any error occurs
0030  0006           ERR$       Appended to ERRMSG$ to indicate nature of er
                  ror
0030  0006           TEMP       Storage of real variables while copying patt
                  ern data files
0030  0006   REM $PAGE
0030  0006   SUB PATTERN.FILE STATIC
0047  0006
0047  0006           GOSUB INITIALIZE
004D  0006           TYPE% = 0
0054  0008
0054  0008           WHILE TYPE% <> 3
005F  0008                   A$ = ""
0069  000C                   WHILE A$ = ""
007B  000C                           A$ = INKEY$
0082  000C                   WEND
0085  000C                   IF A$ = CHR$(0) + CHR$(75) THEN TYPE% = 1:
             'left arrow
00AA  000C                   IF A$ = CHR$(0) + CHR$(77) THEN TYPE% = 2:
             'right arrow
00CF  000C                   IF A$ = CHR$(13) THEN TYPE% = 3:
             '<cr> to execute selection
00E9  000C
00E9  000C                   ON TYPE% GOSUB T1, T2, T3
00FB  000C           WEND
00FC  000C
00FC  000C           EXIT SUB
0100  000C
0100  000C   REM $PAGE
0100  000C   '******** SUB-ROUTINES FOR THIS MODULE ********
0100  000C
0100  000C   T1:             'left arrow
0105  000C           TYPE% = 0
010C  000C           IF MENU% = 0 THEN RETURN
011B  000E           DIFF% = -1
0122  0010           GOSUB NEW.MENU
0128  0010           RETURN
012C  0010
012C  0010   T2:             'right arrow
0131  0010           TYPE% = 0
0138  0010           IF MENU% = 4 THEN RETURN
```

```
0147  0010            DIFF% = 1
014E  0010            GOSUB NEW.MENU
0154  0010            RETURN
0158  0010
0158  0010    T3:             '<cr> (execute selected menu item)
015D  0010            LOCATE 25,1:PRINT SPACE$(79);
017A  0010            ON MENU% + 1 GOSUB T3A, T3B, T3C, T3D, T3E
018F  0010            GOSUB MENU.ON
0195  0010            RETURN
0199  0010
0199  0010    REM $PAGE
0199  0010    T3A:            'delete pattern
019E  0010            TYPE% = 0
01A5  0010            FUNCT$ = "Delete"
01AF  0014            GOSUB GET.SOURCE
01B5  0014            IF LEN(PATNAME$) = 0 THEN RETURN
01C7  0018            IF PATNAME$ = SELNAME$ THEN FLAG% = 4:GOSUB SHOW.ERROR:
              RETURN
01E7  001E            GOSUB SEARCH
01ED  001E            IF POINTER% = 0 THEN FLAG% = 1:GOSUB SHOW.ERROR:RETURN
0209  0020
0209  0020            MESSAGE$ = "Deleting " + PATNAME$ + "    Please Wait..
              ."
0220  0024            GOSUB MESSAGE.ON
0226  0024
0226  0024                    'rewrite directory deleting PATNAME$ as indicat
              ed by POINTER%
0226  0024            KILL "PATDIR.OLD"
022D  0024            NAME "PATDIR.RJP" AS "PATDIR.OLD"
0237  0024            OPEN "PATDIR.OLD" FOR INPUT AS #1
0248  0024            OPEN "PATDIR.RJP" FOR OUTPUT AS #2
025A  0024
025A  0024            INPUT #1, PATNUM%
026C  0026            PATNUM% = PATNUM% - 1
0275  0026            WRITE #2,PATNUM%
0286  0026
0286  0026            IF PATNUM% = 0 THEN GOTO DIR.DONE
0295  0026            FOR I% = 1 TO PATNUM% + 1
02A4  0028                    INPUT #1,PATNAME$
02B6  0028                    IF I% <> POINTER% THEN PRINT #2,PATNAME$
02D3  002A            NEXT I%
02E5  002A
02E5  002A    DIR.DONE:
02EA  002A            CLOSE #1:CLOSE #2
02F8  002A
02F8  002A                    'remove data file
02F8  002A            FILE$ = RIGHT$(STR$(POINTER%),LEN(STR$(POINTER%))-1) +
              "PAT.RJP"
031C  002E            KILL FILE$
0323  002E
0323  002E                    'rename remaining data files to maintain linked
               list with directory
0323  002E            WHILE (PATNUM% + 1) > POINTER%
0333  002E                    SFILE$ = RIGHT$(STR$(POINTER%+1),LEN(STR$(POINT
              ER%+1))-1) + "PAT.RJP"
0359  0032                    DFILE$ = RIGHT$(STR$(POINTER%),LEN(STR$(POINTER
              %))-1) + "PAT.RJP"
```

```
037D  0036                    NAME SFILE$ AS DFILE$
0387  0036                    POINTER% = POINTER% + 1
0390  0036            WEND
0393  0036
0393  0036            GOSUB MESSAGE.OFF
0399  0036            PATNAME$ = SELNAME$
03A3  0036            GOSUB T3DA
03A9  0036            GOSUB DISP.DIR
03AF  0036            RETURN
03B3  0036
03B3  0036    REM $PAGE
03B3  0036    T3B:    'copy pattern
03B8  0036            TYPE% = 0
03BF  0036            IF PATNUM% = 80 THEN FLAG% = 3:GOSUB SHOW.ERROR:RETURN
03DB  0036            FUNCT$ = "Copy"
03E5  0036            GOSUB GET.SOURCE
03EB  0036            IF LEN(PATNAME$) = 0 THEN RETURN
03FD  0036            GOSUB SEARCH
0403  0036            IF POINTER% = 0 THEN FLAG% = 1:GOSUB SHOW.ERROR:RETURN
041F  0036
041F  0036            GOSUB GET.NEW.NAME
0425  0036            IF LEN(NEWNAME$) = 0 THEN RETURN
0437  003A            IF LEN(NEWNAME$) > 15 THEN FLAG% = 2:GOSUB SHOW.ERROR:R
              ETURN
0457  003A
0457  003A            MESSAGE$ = "Copying " + PATNAME$ + " to " + NEWNAME$ +
              "  Please wait.."
047C  003A            GOSUB MESSAGE.ON
0482  003A
0482  003A                    'add NEWNAME$ at end of directory
0482  003A            KILL "PATDIR.OLD"
0489  003A            NAME "PATDIR.RJP" AS "PATDIR.OLD"
0493  003A            OPEN "PATDIR.OLD" FOR INPUT AS #1
04A4  003A            OPEN "PATDIR.RJP" FOR OUTPUT AS #2
04B6  003A
04B6  003A            INPUT #1, PATNUM%
04CB  003A            PATNUM% = PATNUM% + 1
04D1  003A            WRITE #2,PATNUM%
04E2  003A
04E2  003A            FOR I% = 1 TO PATNUM% - 1
04F1  003C                    INPUT #1,TEMP$
0503  0040                    PRINT #2,TEMP$
0513  0040            NEXT I%
0525  0040            PRINT #2,NEWNAME$
0535  0040
0535  0040            CLOSE #1:CLOSE #2
0543  0040
0543  0040                    'create copy of pattern data file
0543  0040            FILE$ = RIGHT$(STR$(POINTER%),LEN(STR$(POINTER%))-1) +
              "PAT.RJP"
0567  0040            NEWFILE$ = RIGHT$(STR$(PATNUM%),LEN(STR$(PATNUM%))-1) +
              "PAT.RJP"
058B  0044
058B  0044            OPEN FILE$ FOR INPUT AS #1
059C  0044            OPEN NEWFILE$ FOR OUTPUT AS #2
05AE  0044
```

```
05AE  0044          INPUT #1,ELNUM%
05C0  0046          WRITE #2,ELNUM%
05D1  0046
05D1  0046          FOR I% = 1 TO 4
05D8  0046                  INPUT #1,TEMP
05EA  004A                  WRITE #2,TEMP
05FA  004A          NEXT I%
060A  004A
060A  004A          FOR I% = 1 TO ELNUM%
0617  004C                  FOR J% = 1 TO 6
061E  004C                          INPUT #1,TEMP%
0630  004E                          WRITE #2,TEMP%
0641  004E                  NEXT J%
0651  0050          NEXT I%
0663  0050
0663  0050          CLOSE #1:CLOSE #2
0671  0050
0671  0050          GOSUB MESSAGE.OFF
0677  0050          GOSUB DISP.DIR
067D  0050          RETURN
0681  0050
0681  0050  T3C:            'rename pattern
0686  0050          TYPE% = 0
068D  0050          FUNCT$ = "Rename"
0697  0050          GOSUB GET.SOURCE
069D  0050          IF LEN(PATNAME$) = 0 THEN RETURN
06AF  0050          GOSUB SEARCH
06B5  0050          IF POINTER% = 0 THEN FLAG% = 1:GOSUB SHOW.ERROR:RETURN
06D1  0050
06D1  0050          GOSUB GET.NEW.NAME
06D7  0050          IF LEN(NEWNAME$) = 0 THEN RETURN
06E9  0050          IF LEN(NEWNAME$) > 15 THEN FLAG% = 2:GOSUB SHOW.ERROR:R
            ETURN
0709  0050          IF NEWNAME$ = PATNAME$ THEN RETURN
071C  0050
071C  0050          MESSAGE$ = "Renaming " + PATNAME$ + " to " + NEWNAME$ +
            "   Please wait.."
0741  0050          GOSUB MESSAGE.ON
0747  0050
0747  0050                  'change pattern name in directory replacing PAT
            NAME$ with NEWNAME$
0747  0050          KILL "PATDIR.OLD"
074E  0050          NAME "PATDIR.RJP" AS "PATDIR.OLD"
0756  0050          OPEN "PATDIR.OLD" FOR INPUT AS #1
0769  0050          OPEN "PATDIR.RJP" FOR OUTPUT AS #2
077B  0050
077B  0050          INPUT #1, PATNUM%
078D  0050          WRITE #2,PATNUM%
079E  0050
079E  0050          FOR I% = 1 TO PATNUM%
07AB  0052                  INPUT #1,TEMP$
07BD  0052                  IF I% <> POINTER% THEN PRINT #2,TEMP$
07DA  0052                  IF I% = POINTER% THEN PRINT #2,NEWNAME$
07F7  0052          NEXT I%
0809  0052
0809  0052          CLOSE #1:CLOSE #2
0817  0052
```

```
0817  0052          GOSUB MESSAGE.OFF
081D  0052
081D  0052                'select new pattern name if necessary
081D  0052          IF PATNAME$ = SELNAME$ THEN PATNAME$ = NEWNAME$:GOSUB T
               3DA
083C  0052          GOSUB DISP.DIR
0842  0052          RETURN
0846  0052
0846  0052  REM $PAGE
0846  0052  T3D:         'select pattern for printing
084B  0052          TYPE% = 0
0852  0052          FUNCT$ = "Select"
085C  0052          GOSUB GET.SOURCE
0862  0052          IF LEN(PATNAME$) = 0 THEN RETURN
0874  0052          IF PATNAME$ = SELNAME$ THEN RETURN
0887  0052          GOSUB T3DA
088D  0052          GOSUB DISP.DIR
0893  0052          RETURN
0897  0052
0897  0052  T3DA:
089C  0052          GOSUB SEARCH
08A2  0052          IF POINTER% = 0 THEN FLAG% = 1:GOSUB SHOW.ERROR:RETURN
08BE  0052
08BE  0052          MESSAGE$ = "Selecting " + PATNAME$ + "    Please Wait.
               .."
08D5  0052          GOSUB MESSAGE.ON
08DB  0052
08DB  0052                'change entrys in pattern default file PATDEF.R
               JP
08DB  0052          OPEN "PATDEF.RJP" FOR OUTPUT AS #1
08ED  0052          FILE$ = RIGHT$(STR$(POINTER%),LEN(STR$(POINTER%))-1) +
               "PAT.RJP"
0911  0052
0911  0052          PRINT #1,FILE$
0921  0052          PRINT #1,PATNAME$
0931  0052
0931  0052          CLOSE #1
093B  0052          GOSUB MESSAGE.OFF
093E  0052          RETURN
0942  0052
0942  0052  T3E:    'exit pattern filing
0947  0052          RETURN
094B  0052
094B  0052  REM $PAGE
094B  0052  SEARCH:
0950  0052          POINTER% = 0
0957  0052          OPEN "PATDIR.RJP" FOR INPUT AS #1
0968  0052          INPUT #1,PATNUM%:'     get number of patterns in direc
               tory
097A  0052          IF PATNUM% = 0 THEN CLOSE #1:RETURN
0990  0052          TEMP$ = ""
099A  0052          WHILE (POINTER% < PATNUM%) AND (PATNAME$ <> TEMP$)
09C2  0052              LINE INPUT #1,TEMP$
09CF  0052              POINTER% = POINTER% + 1
09DB  0052          WEND
09DB  0052          IF PATNAME$ <> TEMP$ THEN POINTER% = 0
09F1  0052          CLOSE #1
```

```
09FB    0052            RETURN
09FC    0052
09FC    0052    GET.SOURCE:
0A01    0052            LOCATE 25,1:COLOR 15,0:PRINT "Enter Pattern Name to "FU
                NCT$" ";
0A33    0052            LINE INPUT;"",PATNAME$
0A41    0052            LOCATE 25,1:PRINT SPACE$(79);
0A5E    0052            RETURN
0A62    0052
0A62    0052    GET.NEW.NAME:
0A67    0052            LOCATE 25,1:COLOR 15,0:PRINT "Enter New Pattern Name ";
0A8D    0052            LINE INPUT;"",NEWNAME$
0A9B    0052            LOCATE 25,1:PRINT SPACE$(79);
0ABB    0052            RETURN
0ABC    0052
0ABC    0052    DISP.DIR:       'display directory in 4 columns, 20 rows
0AC1    0052                    'read default pattern name into SELNAME$
0AC1    0052            OPEN "PATDEF.RJP" FOR INPUT AS #1
0AD2    0052            INPUT #1,SELNAME$:      'discard data file name
0AE4    0052            INPUT #1,SELNAME$
0AF6    0052            CLOSE #1
0AFD    0052
0AFD    0052            OPEN "PATDIR.RJP" FOR INPUT AS #1
0B0E    0052            INPUT #1,PATNUM%:'      read number of patterns
0B20    0052
0B20    0052            MESSAGE$ = "Reading Pattern Directory   Please Wait"
0B2A    0052            GOSUB MESSAGE.ON
0B30    0052            FLAG% = 0
0B37    0052            TEMP% = PATNUM% - 1:IF PATNUM% < 80 THEN TEMP% = PATNUM
                %
0B52    0052            FOR I% = 0 TO TEMP%
0B5E    0054                    LOCATE (I% MOD 20)+1,(INT(I%/20)*20)+1
0B91    0054                    PRINT SPACE$(18);
0BA1    0054            NEXT I%
0BB3    0054
0BB3    0054            FOR I% = 0 TO PATNUM% - 1
0BC1    0056                    INPUT #1,PATNAME$
0BD3    0056                    LOCATE (I% MOD 20)+1,(INT(I%/20)*20)+3
0C06    0056                    PRINT PATNAME$;
0C13    0056                    IF PATNAME$ = SELNAME$ THEN LOCATE (I% MOD 20)+
                1,(INT(I%/20)*20)+1:PRINT "*";
0C62    0056            NEXT I%
0C77    0056            CLOSE #1
0C7E    0056            GOSUB MESSAGE.OFF
0CB4    0056            RETURN
0CBB    0056
0CBB    0056    INITIALIZE:
0CBD    0056            DIM MENU$(4,1)
0CBE    007E            MENU$(0,0) = "Delete"
0CA6    007E            MENU$(0,1) = "Remove a pattern file from the directory"
0CC1    007E            MENU$(1,0) = "Copy"
0CDC    007E            MENU$(1,1) = "Copy a pattern file to a new pattern name
                "
0CF5    007E            MENU$(2,0) = "Rename"
0D12    007E            MENU$(2,1) = "Rename a pattern file in the directory"
0D30    007E            MENU$(3,0) = "Select"
0D4B    007E            MENU$(3,1) = "Select a pattern file to be printed"
```

```
0D67   007E            MENU$(4,0) = "Exit"
0D82   007E            MENU$(4,1) = "Return to the main menu"
0D9E   007E
0D9E   007E            COLOR 9,0:CLS
0DB1   007E            LOCATE 21,1
0DBE   007E            FOR I% = 1 TO 80
0DC5   007E                    PRINT "D";
0DD2   007E            NEXT I%
0DE2   007E
0DE2   007E            FOR MENU% = 0 TO 4
0DE8   007E                    GOSUB MENU.OFF
0DEE   007E            NEXT MENU%
0DFE   007E
0DFE   007E            GOSUB DISP.DIR
0E04   007E            IF FLAG% > 0 THEN GOSUB SHOW.ERROR
0E15   007E            MENU% = 4
0E1C   007E            GOSUB MENU.ON
0E22   007E
0E22   007E            RETURN
0E26   007E
0E26   007E    NEW.MENU:
0E2B   007E            GOSUB MENU.OFF
0E31   007E            MENU% = MENU% + DIFF%
0E3D   007E            GOSUB MENU.ON
0E43   007E            RETURN
0E47   007E
0E47   007E    MENU.ON:
0E4C   007E            LOCATE 22,(MENU%*10)+18
0E63   007E            COLOR 0,7
0E6F   007E            PRINT MENU$(MENU%,0);
0E8D   007E            LOCATE 25,40-LEN(MENU$(MENU%,1))/2
0EC1   007E            COLOR 7,0
0ECD   007E            PRINT MENU$(MENU%,1);
0EEC   007E            RETURN
0EF0   007E
0EF0   007E    MENU.OFF:
0EF5   007E            LOCATE 22,(MENU%*10)+18
0F0C   007E            COLOR 14,0
0F18   007E            PRINT MENU$(MENU%,0);
0F36   007E            LOCATE 25,40-LEN(MENU$(MENU%,1))/2
0F6A   007E            PRINT SPACE$(LEN(MENU$(MENU%,1)));
0F8F   007E            RETURN
0F93   007E
0F93   007E    SHOW.ERROR:
0F98   007E            ON FLAG% GOSUB ER1, ER2, ER3, ER4
0FA9   007E            ERRMSG$ = ERR$ + "    Strike any key.."
0FB9   0086            LOCATE 24,40-LEN(ERRMSG$)/2
0FDB   0086            COLOR 13,0
0FE7   0086            PRINT ERRMSG$;
0FF4   0086            A$ = ""
0FFE   0086            WHILE A$ = ""
100D   0086                    A$ = INKEY$
1017   0086            WEND
101A   0086            GOSUB MESSAGE.OFF
1020   0086            RETURN
1024   0086
1024   0086    ER1:
```

```
1029  0086            ERR$ = PATNAME$ + " Not Found in the Directory"
1039  0086            RETURN
103D  0086
103D  0086    ER2:
1042  0086            ERR$ = "Pattern Name is too Long (15 characters max.)"
104C  0086            RETURN
1050  0086
1050  0086    ER3:
1055  0086            ERR$ = "Directory is Full (80 patterns max.)"
105F  0086            RETURN
1063  0086
1063  0086    ER4:
1068  0086            ERR$ = "Cannot Modify SELECTd pattern Name"
1072  0086            RETURN
1076  0086
1076  0086    MESSAGE.ON:
107B  0086            LOCATE 24,38 - LEN(MESSAGE$) / 2:COLOR 11,0:PRINT MESSA
              GE$;
10B6  0086            RETURN
10BA  0086
10BA  0086
10BA  0086    MESSAGE.OFF:
10BF  0086            LOCATE 24,1:COLOR 15,0:PRINT SPACE$(79);
10E8  0086            RETURN
10EC  0086
10EC  0086    END SUB
10F3  0086
16BB  0086

50426 Bytes Available
45670 Bytes Free

0 Warning Error(s)
    0 Severe  Error(s)

Reagent Jet Printer
Main Line Code

Offset  Data   Source Line        IBM Personal Computer BASIC Compiler V2.00

0030    0006   REM $TITLE:'Reagent Jet Printer' $SUBTITLE:'Main Line Code'
0030    0006
0030    0006   'MODULE   - "MAIN"
0030    0006
0030    0006   'AUTHOR   - N. A. Enevold
0030    0006
0030    0006   'COPYRIGHT (C) 1986 ABBOTT LABORATORIES
0030    0006
0030    0006   'REVISION - 1.1 02-19-86 NAE Add notes and revise TYPE% resetin
               g
0030    0006            - 1.0 02-14-86 NAE Creation of initial code
0030    0006
0030    0006   'SYSTEM   - This code can only be compiled by the BASCOM
0030    0006              COMPILER, it will not run under the INTERPRETER!!
0030    0006
0030    0006   'DESCRIPTION
```

```
0030  0006    '       This is the main controlling module for the Reagent Jet
              Printer.
0030  0006    '       It displays a menu in table form that allows 6 function
              s to be
0030  0006    '       selected.  PATTERN DEFINITION allows the user to define
              patterns
0030  0006    '       to be printed.  PATTERN FILING lets the user delete, co
              py, rename
0030  0006    '       and select patterns for printing.  REAGENT CALIBRATION
              permits setting
0030  0006    '       of operation parameters for different reagents.  REAGEN
              T FILING is
0030  0006    '       the same as pattern filing.  PRINTING PRINT prints the
              selected
0030  0006    '       pattern with the selected reagent.  SYSTEM EXIT TO DOS
              ends the session.
0030  0006    '       Using up and down arrow keys let the user move through
              the menu and
0030  0006    '       the Enter <cr> key activates the selection.
0030  0006
0030  0006    'DATA DICTIONARY
0030  0006    '       MENU%           This value represents the current menu
              item (0-5)
0030  0006    '       MENU$(5,1)      String array for displaying menu items.
              6 rows by 2 columns
0030  0006    '                       Each row corresponds to a menu item (0-
              5)
0030  0006    '                       First column is short menu name in high
              lighted area
0030  0006    '                       Second column is long description displ
              ayed at menu bottom
0030  0006    '       MROW%(5)        This array stores to row in which the s
              hort menu name will be displayed
0030  0006    '       DIFF%           This value is used it change MENU% in r
              esponse to arrow keys
0030  0006    '       TYPE%           This value is set based on which valid
              key is pressed
0030  0006    '                       0 = No valid key.  1 = Up Arrow.  2 = D
              own Arrow.  3 = <cr>.
0030  0006    '       TEMP%           Used to store MENU% while screen is ref
              reshed
0030  0006    '       A$              Used to store single input keystrokes
0030  0006    '       C$              Used to store special graphics characte
              rs used in drawing the menu table
0030  0006    '       I%              Counter used to refresh display
0030  0006    '       R%              Row in which special graphics character
              is displayed
0030  0006    '       C%              Column in which special graphics charac
              ter is displayed
0030  0006    REM $PAGE
0030  0006
0030  0006    'Main-line code for RJP Reagent Jet Printer
0030  0006
0030  0006    MAIN.LINE.CODE:
0030  0006
0030  0006            GOSUB INITIALIZE
```

```
004B   0006
004B   0006           WHILE TYPE% <> 3
0056   0008
0056   0008                   TYPE% = 0
005D   0008                   A$ = ""
0067   000C                   WHILE A$ = ""
0076   000C                           A$ = INKEY$
0080   000C                   WEND
0083   000C
0083   000C                   IF A$ = CHR$(0) + CHR$(72) THEN TYPE% = 1:'
               up arrow
00A8   000C                   IF A$ = CHR$(0) + CHR$(80) THEN TYPE% = 2:'
               down arrow
00CD   000C                   IF A$ = CHR$(13) THEN TYPE% = 3:'
               <cr> execute command
00E7   000C
00E7   000C                   ON TYPE% GOSUB T1, T2, T3
00F6   000C
00F6   000C           WEND
00FA   000C
00FA   000C           CLS
0101   000C           COLOR 7,0,0
0112   000C           SYSTEM
0116   000C
0116   000C   REM $PAGE
0116   000C   '******** SUB-ROUTINES FOR MAIN PROGRAM
0116   000C   T1:     'up arrow
011B   000C           IF MENU% = 0 THEN RETURN
012A   000E           DIFF% = -1
0131   0010           GOSUB NEW.MENU
0137   0010           RETURN
013B   0010
013B   0010   T2:     'down arrow
0140   0010           IF MENU% = 5 THEN RETURN
014F   0010           DIFF% = 1
0156   0010           GOSUB NEW.MENU
015C   0010           RETURN
0160   0010
0160   0010   T3:
0165   0010           ON MENU% + 1 GOSUB T31, T32, T33, T34, T35, T36
017C   0010           IF MENU% < 5 THEN TYPE% = 0:'   reset TYPE% so program
               won't end
018E   0010           SCREEN 0,0,3,3
01A5   0010           RETURN
01A9   0010
01A9   0010   T31:    'pattern definition
01AE   0010           CALL PATENTRY:          'in module PATENT
01BA   0010           GOSUB REFRESH
01C0   0010           RETURN
01C4   0010
01C4   0010   T32:    'pattern filing
01C9   0010           SCREEN 0,0,0,0:CLS
01E5   0010           CALL PATTERN.FILE:      'in module PATFILE
01F1   0010           RETURN
01F5   0010
01F5   0010   T33:    'reagent calibration
01FA   0010           CALL REAGENT.CALIBRATE:'in module REACAL
```

```
0206  0010          RETURN
020A  0010
020A  0010  T34:    'reagent filing menu
020F  0010          SCREEN 0,0,0,0:CLS
022B  0010          CALL REAGENT.FILE:      'in module REAFILE
0237  0010          RETURN
023B  0010
023B  0010  T35:    'print pattern
0240  0010          CALL PATPRINT:          'in module PATPRINT
024C  0010          RETURN
0250  0010
0250  0010  T36:    'exit system, don't reset TYPE%
0255  0010          RETURN
0259  0010
0259  0010  REM $PAGE
0259  0010  NEW.MENU:
025E  0010          GOSUB MENU.OFF
0264  0010          MENU% = MENU% + DIFF%
0270  0010          GOSUB MENU.ON
0276  0010          RETURN
027A  0010
027A  0010  INITIALIZE:
027F  0010          CALL PCI.INIT
028B  0010
028B  0010  '       define and initialize arrays
028B  0010          DIM MROW%(5)
028C  001C          MROW%(0) = 4
029E  001C          MROW%(1) = 6
02B1  001C          MROW%(2) = 10
02C4  001C          MROW%(3) = 12
02D7  001C          MROW%(4) = 16
02EA  001C          MROW%(5) = 20
02FD  001C
02FD  001C          DIM MENU$(5,1)
02FE  004C          RESTORE MENU.STRING.DATA
0305  004C          FOR I% = 0 TO 5
030B  004C                  READ MENU$(I%,0),MENU$(I%,1)
033B  004E          NEXT I%
034B  004E
034B  004E  '       set initial values into variables
034B  004E          TYPE% = 0
0352  004E          MENU% = 0
0359  004E
0359  004E  REFRESH:'redraw screen and highlight current menu selection
035E  004E
035E  004E          SCREEN 0,0,0,0:CLS:COLOR 7,0,0
038B  004E          LOCATE 10,32:PRINT "Loading Menu....."
03A5  004E          SCREEN 0,0,3,0:CLS
03C2  004E
03C2  004E
03C2  004E          COLOR 13,0
03CE  004E          LOCATE 1,31
03DB  004E          PRINT "REAGENT JET PRINTER";
03E8  004E          COLOR 10,0
03F4  004E          LOCATE 5,26
0401  004E          PRINT "PATTERN"
040E  004E          LOCATE 11,26
```

```
041B   004E          PRINT "REAGENT"
042B   004E          LOCATE 16,26
0435   004E          PRINT "PRINTING"
0442   004E          LOCATE 20,27
044F   004E          PRINT "SYSTEM"
045C   004E
045C   004E    '     draw the menu table in special graphics characters
045C   004E          COLOR 9,0
0468   004E          FOR I% = 18 TO 63
046F   004E                 LOCATE 2,I%:PRINT "D";
048A   004E                 LOCATE 8,I%:PRINT "D";
04A5   004E                 LOCATE 14,I%:PRINT "D";
04C0   004E                 LOCATE 18,I%:PRINT "D";
04DB   004E                 LOCATE 22,I%:PRINT "D";
04F6   004E                 LOCATE 24,I%:PRINT "D";
0511   004E          NEXT I%
0524   004E          FOR I% = 3 TO 23
052B   004E                 LOCATE I%,17:PRINT "J";
0546   004E                 LOCATE I%,64:PRINT "J";
0561   004E          NEXT I%
0571   004E          RESTORE TABLE
0578   004E          FOR I% = 1 TO 12
057F   004E                 READ R%,C%,C$
0592   0056                 LOCATE R%,C%:PRINT C$;
05AE   0056          NEXT I%
05BE   0056
05BE   0056    '     print the instructions
05BE   0056          COLOR 7,0
05CA   0056          LOCATE 25,6
05D7   0056          PRINT "Use    or    to highlight menu items. Use     to
                activate selection.";
05E4   0056
05E4   0056          COLOR 15,0
";
060A   0056          LOCATE 25,15:PRINT "";
0624   0056          LOCATE 25,47:PRINT "DY";
063E   0056
063E   0056    '     display the 6 menu choices
063E   0056          TEMP% = MENU%
0645   0058          FOR MENU% = 0 TO 5
064B   0058                 GOSUB MENU.OFF
0651   0058          NEXT MENU%
0661   0058          MENU% = TEMP%
0668   0058
0668   0058    '     highlight the currently active menu item
0668   0058          GOSUB MENU.ON
066E   0058
066E   0058          SCREEN 0,0,3,3
0685   0058          RETURN
0689   0058
0689   0058    MENU.ON:'highlight the menu MENU% and display its long descript
                ion
068E   0058          COLOR 0,7
069A   0058          LOCATE MROW%(MENU%),52-LEN(MENU$(MENU%,0))/2
06DA   0058          PRINT MENU$(MENU%,0);
06F8   0058          COLOR 7,0
0704   0058          LOCATE 23,40.5-LEN(MENU$(MENU%,1))/2
```

```
0738  0058          PRINT MENU$(MENU%,1);
0757  0058          RETURN
075B  0058
075B  0058  MENU.OFF:'un-highlight menu MENU% and erase long description
0760  0058          COLOR 14,0
076C  0058          LOCATE MROW%(MENU%),52-LEN(MENU$(MENU%,0))/2
07AC  0058          PRINT MENU$(MENU%,0);
07CA  0058          COLOR 7,0
07D6  0058          LOCATE 23,40.5-LEN(MENU$(MENU%,1))/2
080A  0058          PRINT SPACE$(LEN(MENU$(MENU%,1)));
082F  0058          RETURN
0833  0058
0833  0058  REM $PAGE
0833  0058  '######## DATA FIELDS USED BY THE MAIN PROGRAM ########
0833  0058
0833  0058  MENU.STRING.DATA:     'first entry is menu name, second is lo
            ng description
083B  0058
083B  0058          DATA "DEFINITION", "Create and Modify Patterns"
083A  0058          DATA "FILING",     "Delete, Copy, Rename, and Select Pa
            tterns"
083C  0058          DATA "CALIBRATION","Calibrate and Modify Reagent Profil
            es"
083E  0058          DATA "FILING",     "Delete, Copy, Rename, and Select Re
            agents"
0840  0058          DATA "PRINT",      "Print Selected Pattern with Selecte
            d Reagent"
0842  0058          DATA "EXIT TO DOS","Leave Program and Return to DOS"
0844  0058
0844  0058  TABLE:  'first entry is row, second is column, third is special
            graphics character
0849  0058
0849  0058          DATA 2,17,"Z"
084B  0058          DATA 2,64,"?"
084D  0058          DATA 8,17,"C"
084F  0058          DATA 8,64,"4"
0851  0058          DATA 14,17,"C"
0853  0058          DATA 14,64,"4"
0855  0058          DATA 18,17,"C"
0857  0058          DATA 18,64,"4"
0859  0058          DATA 22,17,"C"
085B  0058          DATA 22,64,"4"
085D  0058          DATA 24,17,"@"
085F  0058          DATA 24,64,"Y"
0861  0058
0861  0058          END
0865  0058
0B42  0058
```

50426 Bytes Available
47680 Bytes Free

0 Warning Error(s)
    0 Severe  Error(s)

We claim:
1. A diagnostic analyzing system comprising:
    means for positioning and containing at least one of (1) a diagnostic reagent fluid and (2) a sample; and means for precisely metering and dispensing the other one of the (1) diagnostic reagent fluid and (2) sample to interact with the positioned one of the (1) diagnostic reagent fluid and (2) sample, the metering and dispensing means comprising:

a jetting chamber defining a volume and comprising a first and second aperture, the first aperture adapted to receive the other one of the (1) diagnostic reagent fluid and (2) sample, the second aperture defining an orifice;

a transducer in mechanical communication with the jetting chamber, the transducer operative to alternately expand and de-expand the volume of the jetting chamber in response to a selected electrical pulse and thereby cause the jetting chamber to propel a reproducibly sized droplet of the other one of the (1) diagnostic reagent fluid and (2) sample from the orifice;

means for generating a number of electrical pulses sufficient to cause a precise quantity of the other one of the (1) diagnostic reagent fluid and (2) sample to be dispensed; and means for detecting reaction results produced by the interaction of the diagnostic reagent fluid and sample.

2. The invention of claim 1 wherein the fluid is an analytic reagent.

3. The invention of claim 1 wherein the system further comprises means for incubating at least one of the fluid and sample at a predetermined temperature for a predetermined time period.

4. The invention of claim 1 wherein at least one of the fluid and sample is a biologically active reagent.

5. The invention of claim 1 wherein the means for generating the electrical pulse comprises means for adjusting the electrical characteristics of the pulse in accordance with selected variable macroscopic properties of the other one of the (1) diagnostic reagent fluid and (2) sample.

6. The invention of claim 1 wherein the transducer is one of (1) a piezo-electric transducer; (2) a magnetostrictive transducer; (3) an electro-strictive transducer; and (4) an electro-mechanical transducer.

7. The invention of claim 1 wherein the orifice comprises an end face and the end face is coated with a hydrophobic material.

8. A method of assaying for an analyte comprising the steps of:
(1) dispensing precise quantities of at least one diagnostic reagent fluid and at least one fluid sample by:
  (a) generating at least one electrical pulse of selected predefined characteristics;
  (b) altering the volume of a chamber containing the fluid by electro-mechanical means in response to the electrical pulse such that at least one droplet of fluid of a selected predetermined and reproducible volume is jetted from the chamber; and
  (c) repeating steps (a) and (b) until a desired quantity of fluid has been dispensed; and
(2) detecting a reaction result produced by the fluid mixture.

9. The invention of claim 8 wherein the method further comprises the step of incubating at least one of the fluids at a predetermined temperature for a predetermined time period.

10. A method of manufacturing a diagnostic test device, the test device of the type including a chemically treated test medium, the method comprising the steps of:
(a) positioning a test device medium relative to a jetting chamber;
(b) generating at least one electrical pulse of selected predetermined characteristics;
(c) altering the volume of a chamber containing a reagent fluid by electro-mechanical means in response to the selected electrical pulse such that reagent fluid jetted from the chamber is in the form of a predetermined and reproducibly sized droplet and impacts the test device medium; and
(d) repeating steps (a) through (c) until a desired pattern of reagent fluid has been formed on the test device medium.

11. A diagnostic test device manufactured in accordance with the method of claim 10.

12. A diagnostic test device manufactured in accordance with the method of claim 10 and wherein the pattern corresponds to at least one alphanumeric character.

13. A diagnostic fluid dispensing apparatus comprising:
a jetting chamber comprising an orifice and a fluid intake aperture;
a collapsible fluid reservoir containing at least one diagnostic reagent fluid connected to the intake aperture of the jetting chamber; and
a transducer adapted to alternately expand and de-expand the jetting chamber to expel fluid droplets;
the jetting chamber, reservoir and transducer cooperating such that capillary action at the orifice produces a pressure differential between the interior and exterior of the fluid reservoir upon emittance of fluid from the jetting chamber.

14. A method of manufacturing a diagnostic test device comprising the steps of:
(a) positioning a test device medium relative to a jetting chamber;
(b) applying pressurized diagnostic reagent fluid to a jetting chamber with an orifice such that fluid is expelled through the orifice;
(c) altering the volume of the chamber by electro-mechanical means such that the expelled fluid is in the form of a stream of distinct uniformly sized droplets; and
(d) directing at least one of the (1) expelled fluid and (2) the test device medium such that the fluid impacts the medium in a desired manner.

15. The invention of claim 1 wherein the sample is a fluid.

16. The invention of claim 1 wherein the system further comprises means for pressurizing the other one of the (1) diagnostic reagent fluid and (2) sample, the means for pressurizing and the transducer cooperating to produce a stream of distinct reproducibly sized droplets.

17. The invention of claim 10 wherein the system further comprises means for pressurizing the fluid, the means for pressurizing and the transducer cooperating to produce a stream of distinct reproducibly sized droplets.

18. The invention of claim 13 wherein the diagnostic reagent fluid is a biologically active reagent.

* * * * *